(12) United States Patent
Matray et al.

(10) Patent No.: US 9,851,359 B2
(45) Date of Patent: Dec. 26, 2017

(54) ULTRA BRIGHT DIMERIC OR POLYMERIC DYES WITH SPACING LINKER GROUPS

(71) Applicants: SONY CORPORATION OF AMERICA, New York, NY (US); SONY CORPORATION, Tokyo (JP)

(72) Inventors: Tracy Matray, Snohomish, WA (US); Sharat Singh, Rancho Santa Fe, CA (US)

(73) Assignees: SONY CORPORATION OF AMERICA, New York, NY (US); SONY CORPORATION, Tokyo (JP)

(*) Notice: Subject to any disclaimer, the term of this patent is extended or adjusted under 35 U.S.C. 154(b) by 0 days.

(21) Appl. No.: 15/481,378

(22) Filed: Apr. 6, 2017

(65) Prior Publication Data
US 2017/0292957 A1    Oct. 12, 2017

Related U.S. Application Data

(60) Provisional application No. 62/318,935, filed on Apr. 6, 2016.

(51) Int. Cl.
| | | |
|---|---|---|
| C07F 9/09 | (2006.01) | |
| G01N 33/53 | (2006.01) | |
| G01N 33/58 | (2006.01) | |
| C09B 69/10 | (2006.01) | |
| C09B 3/14 | (2006.01) | |
| C09B 11/26 | (2006.01) | |
| C07F 9/576 | (2006.01) | |

(52) U.S. Cl.
CPC ........... *G01N 33/582* (2013.01); *C09B 3/14* (2013.01); *C09B 11/26* (2013.01); *C09B 69/101* (2013.01); *C09B 69/102* (2013.01); *C09B 69/109* (2013.01); *C07F 9/09* (2013.01); *C07F 9/094* (2013.01); *C07F 9/098* (2013.01); *C07F 9/5765* (2013.01)

(58) Field of Classification Search
CPC ........ C07F 9/65522; C07F 9/09; C07F 9/098; C07F 9/5765; C07F 9/094; C07H 21/04; G01N 33/53; G01N 33/582; G01N 33/583; C09B 69/101; C09B 69/102; C09B 69/109; C09B 3/14; C09B 11/26; C09B 1/00

See application file for complete search history.

(56) References Cited

U.S. PATENT DOCUMENTS

| | | | |
|---|---|---|---|
| 5,268,486 A | 12/1993 | Waggoner et al. | |
| 5,318,894 A | 6/1994 | Pugia | |
| 6,140,480 A | 10/2000 | Kool | |
| 6,171,859 B1 | 1/2001 | Herrnstadt et al. | |
| 6,218,108 B1 | 4/2001 | Kool | |
| 6,479,650 B1 | 11/2002 | Kool | |
| 6,670,193 B2 | 12/2003 | Kool | |
| 7,172,907 B2 | 2/2007 | Chen et al. | |
| 7,423,133 B2 | 9/2008 | Kool et al. | |
| 8,217,389 B2 | 7/2012 | Nakano et al. | |
| 2003/0207208 A1 | 11/2003 | Uenishi | |
| 2004/0014981 A1 | 1/2004 | Lugade et al. | |
| 2004/0138467 A1 | 7/2004 | French et al. | |
| 2004/0224372 A1 | 11/2004 | Li et al. | |
| 2005/0123935 A1 | 6/2005 | Haugland et al. | |
| 2007/0042398 A1 | 2/2007 | Peng et al. | |
| 2007/0077549 A1 | 4/2007 | Buller et al. | |
| 2008/0227939 A1 | 9/2008 | Mizoshita et al. | |
| 2009/0299070 A1 | 12/2009 | Berens et al. | |
| 2010/0039684 A1 | 2/2010 | Kolb et al. | |
| 2012/0116079 A1 | 5/2012 | Lukhtanov et al. | |
| 2012/0126175 A1 | 5/2012 | Ueno et al. | |
| 2013/0102021 A1 | 4/2013 | Beacham et al. | |
| 2013/0119363 A1 | 5/2013 | Sasaki et al. | |
| 2013/0244891 A1 | 9/2013 | Waggoner et al. | |
| 2016/0208100 A1 | 7/2016 | Matray et al. | |
| 2016/0341736 A1 | 11/2016 | Matray et al. | |
| 2016/0347907 A1 | 12/2016 | Dose | |

FOREIGN PATENT DOCUMENTS

| | | |
|---|---|---|
| WO | 01/69254 A2 | 9/2001 |
| WO | 02/36832 A2 | 5/2002 |
| WO | 2006/099050 A2 | 9/2006 |
| WO | 2010/026957 A1 | 3/2010 |
| WO | 2014/147642 A1 | 9/2014 |
| WO | 2015/027176 A1 | 2/2015 |

OTHER PUBLICATIONS

PubChem, "US20100012929A1-20100121-C00010_4," SID No. 140452858, retrieved Mar. 29, 2016 from URL https://pubchem.ncbi.nlm.nih.gov/substance/140452858, 6 pages.
Wang et al., "Cruciforms: Assembling Single Crystal Micro- and Nanostructures from One to Three Dimensions and Their Applications in Organic Field-Effect Transistors," *Chem. Mater.* 21:2840-2845, 2009.
Arian et al., "1,9-Dialkoxyanthracene as a $^1O_2$-Sensitive Linker," *J. Am. Chem. Soc.* 133:3972-3980, 2011.
Lee et al., "Monitoring the Hydrophobic Interactions of Internally Pyrene-Labeled Poly(ethylene oxide)s in Water by Fluorescence Spectroscopy," *Macromolecules* 31:9193-9200, 1998.

*Primary Examiner* — Shafiqul Haq
(74) *Attorney, Agent, or Firm* — Seed IP Law Group LLP

(57) ABSTRACT

Compounds useful as fluorescent or colored dyes are disclosed. The compounds have the following structure (I):

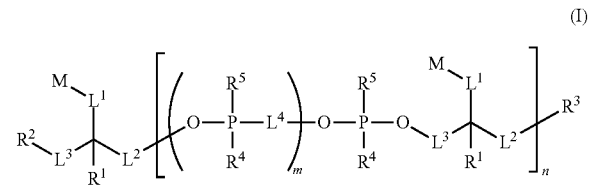

or a stereoisomer, tautomer or salt thereof, wherein $R^1$, $R^2$, $R^3$, $R^4$, $R^5$, $L^1$, $L^2$, $L^3$, $L^4$, M, m and n are as defined herein. Methods associated with preparation and use of such compounds are also provided.

27 Claims, 26 Drawing Sheets

0% Glycine 2.5% Glycine

ULTRA BRIGHT DIMERIC OR POLYMERIC DYES WITH SPACING LINKER GROUPS

BACKGROUND

Field

The present invention is generally directed to dimeric and polymeric fluorescent or colored dyes having rigid spacing groups, and methods for their preparation and use in various analytical methods.

Description of the Related Art

Fluorescent and/or colored dyes are known to be particularly suitable for applications in which a highly sensitive detection reagent is desirable. Dyes that are able to preferentially label a specific ingredient or component in a sample enable the researcher to determine the presence, quantity and/or location of that specific ingredient or component. In addition, specific systems can be monitored with respect to their spatial and temporal distribution in diverse environments.

Fluorescence and colorimetric methods are extremely widespread in chemistry and biology. These methods give useful information on the presence, structure, distance, orientation, complexation and/or location for biomolecules. In addition, time-resolved methods are increasingly used in measurements of dynamics and kinetics. As a result, many strategies for fluorescence or color labeling of biomolecules, such as nucleic acids and protein, have been developed. Since analysis of biomolecules typically occurs in an aqueous environment, the focus has been on development and use of water soluble dyes.

Highly fluorescent or colored dyes are desirable since use of such dyes increases the signal to noise ratio and provides other related benefits. Accordingly, attempts have been made to increase the signal from known fluorescent and/or colored moieties. For example, dimeric and polymeric compounds comprising two or more fluorescent and/or colored moieties have been prepared in anticipation that such compounds would result in brighter dyes. However, as a result of intramolecular fluorescence quenching, the known dimeric and polymeric dyes have not achieved the desired increase in brightness.

There is thus a need in the art for water soluble dyes having an increased molar brightness. Ideally, such dyes and biomarkers should be intensely colored or fluorescent and should be available in a variety of colors and fluorescent wavelengths. The present invention fulfills this need and provides further related advantages.

BRIEF SUMMARY

In brief, embodiments of the present invention are generally directed to compounds useful as water soluble, fluorescent and/or colored dyes and/or probes that enable visual detection of analyte molecules, such as biomolecules, as well as reagents for their preparation. Methods for visually detecting analyte molecules using the dyes are also described.

Embodiments of the presently disclosed dyes include two or more fluorescent and/or colored moieties covalently linked by a linker ("$L^4$"). In contrast to previous reports of dimeric and/or polymeric dyes, the present dyes are significantly brighter than the corresponding monomeric dye compound. While, not wishing to be bound by theory, it is believed that the linker moiety provides sufficient spatial separation between the fluorescent and/or colored moieties such that intramolecular fluorescence quenching is reduced and/or eliminated.

The water soluble, fluorescent or colored dyes of embodiments of the invention are intensely colored and/or fluorescent and can be readily observed by visual inspection or other means. In some embodiments the compounds may be observed without prior illumination or chemical or enzymatic activation. By appropriate selection of the dye, as described herein, visually detectable analyte molecules of a variety of colors may be obtained.

In one embodiment, compounds having the following structure (I) are provided:

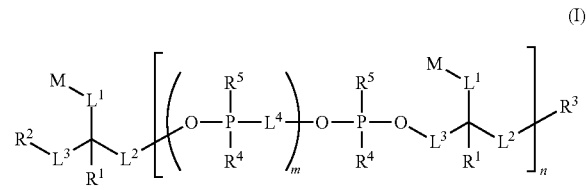

or a stereoisomer, tautomer or salt thereof, wherein $R^1$, $R^2$, $R^3$, $R^4$, $R^5$, $L^1$, $L^2$, $L^3$, $L^4$, M, m and n are as defined herein. Compounds of structure (I) find utility in a number of applications, including use as fluorescent and/or colored dyes in various analytical methods.

In another embodiment, a method for staining a sample is provided, the method comprises adding to said sample a compound of structure (I) in an amount sufficient to produce an optical response when said sample is illuminated at an appropriate wavelength.

In still other embodiments, the present disclosure provides a method for visually detecting an analyte molecule, comprising:

(a) providing a compound of (I); and (b) detecting the compound by its visible properties.

Other disclosed methods include a method for visually detecting a biomolecule, the method comprising:

(a) admixing a compound of structure (I) with one or more biomolecules; and (b) detecting the compound by its visible properties.

Other embodiments provide a method for visually detecting an analyte, the method comprising:

(a) providing a compound as disclosed herein, wherein $R^2$ or $R^3$ comprises a linker comprising a covalent bond to a targeting moiety having specificity for the analyte;

(b) admixing the compound and the analyte, thereby associating the targeting moiety and the analyte; and (c) detecting the compound by its visible properties.

Other embodiments are directed to a composition comprising a compound of structure (I) and one or more analyte molecule, such as a biomolecule. Use of such compositions in analytical methods for detection of the one or more biomolecules is also provided.

In some other different embodiments is provided a compound of structure

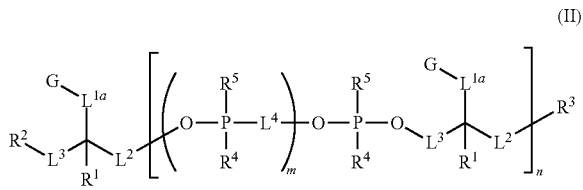

(II)

or a stereoisomer, salt or tautomer thereof, wherein $R^1$, $R^2$, $R^3$, $R^4$, $R^5$, $L^{1a}$, $L^2$, $L^3$, $L^4$, G, m and n are as defined herein. Compounds of structure (II) find utility in a number of applications, including use as intermediates for preparation of fluorescent and/or colored dyes of structure (I).

In yet other embodiments a method for labeling an analyte molecule is provided, the method comprising:

(a) admixing a compound of structure (II), wherein $R^2$ or $R^3$ is Q or a linker comprising a covalent bond to Q, with the analyte molecule;

(b) forming a conjugate of the compound and the analyte molecule; and (c) reacting the conjugate with a compound of formula $M-L^{1b}-G'$, thereby forming at least one covalent bond by reaction of G and G', wherein $R^2$, $R^3$, Q, G and $M-L^{1b}-G'$ are as defined herein.

In some different embodiments another method for labeling an analyte molecule is provided, the method comprising:

(a) admixing a compound of structure (II), wherein $R^2$ or $R^3$ is Q or a linker comprising a covalent bond to Q, with a compound of formula $M-L^{1b}-G'$, thereby forming at least one covalent bond by reaction of G and G; and (b) reacting the product of step (A) with the analyte molecule, thereby forming a conjugate of the product of step (A) and the analyte molecule wherein $R^2$, $R^3$, Q, G and $M-L^{1b}-G'$ are as defined herein.

In more different embodiments, a method for preparing a compound of structure (I) is provided, the method comprising admixing a compound of structure (II) with a compound of formula $M-L^{1b}-G'$, thereby forming at least one covalent bond by reaction of G and G', wherein G and $M-L^{1b}-G'$ are as defined herein.

Still more embodiments are directed to a fluorescent compound comprising Y fluorescent moieties M, wherein the fluorescent compound has a peak fluorescence emission upon excitation with a predetermined wavelength of ultraviolet light of at least 85% of Y times greater than the peak fluorescence emission of a single M moiety upon excitation with the same wavelength of ultraviolet light, and wherein Y is an integer of 2 or more.

These and other aspects of the invention will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

FIG. 26A shows data resulting from the addition of 0% glycine, and FIG. 26B shows data resulting from the addition of 2.5% glycine.

DETAILED DESCRIPTION

Figure 1:
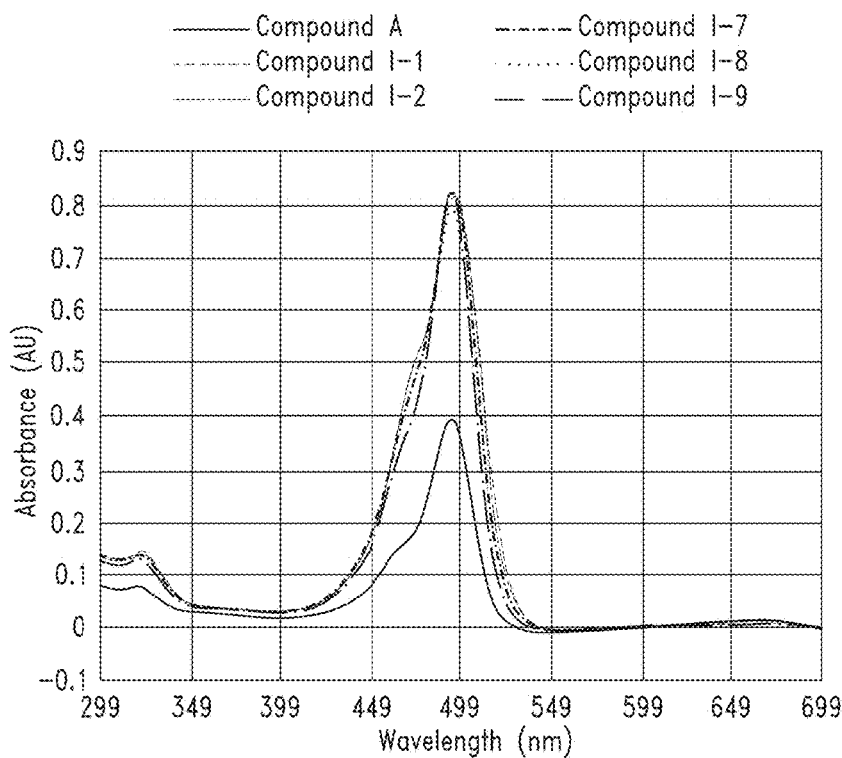
FIG. 1 provides UV absorbance spectra for representative compounds comprising a triethylene glycol spacer and a comparative compound at 5 μm and pH 9.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ group.
"Carboxy" refers to the —$CO_2H$ group.
"Cyano" refers to the —CN group.
"Formyl" refers to the —C(=O)H group.
"Hydroxy" or "hydroxyl" refers to the —OH group.
"Imino" refers to the =NH group.
"Nitro" refers to the —$NO_2$ group.
"Oxo" refers to the =O substituent group.
"Sulfhydryl" refers to the —SH group.
"Thioxo" refers to the =S group.

"Alkyl" refers to a straight or branched hydrocarbon chain group consisting solely of carbon and hydrogen atoms, containing no unsaturation, having from one to twelve carbon atoms ($C_1$-$C_{12}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, alkyl groups are optionally substituted.

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Alkenylene" or "alkenylene chain" refers to a straight or branched divalent hydrocarbon chain linking the rest of the molecule to a radical group, consisting solely of carbon and hydrogen, containing at least one carbon-carbon double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, alkenylene is optionally substituted.

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms, e.g., ethenylene, propenylene, n-butenylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, alkynylene is optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group is optionally substituted. For example, in some embodiments an alkylether is substituted with an alcohol or —OP(=$R_a$)($R_b$)$R_c$, wherein each of $R_a$, $R_b$ and $R_c$ is as defined for compounds of structure (I).

"Alkoxy" refers to a group of the formula —$OR_a$ where $R_a$ is an alkyl group as defined above containing one to twelve carbon atoms. Unless stated otherwise specifically in the specification, an alkoxy group is optionally substituted.

"Alkoxyalkylether" refers to a group of the formula —$OR_aR_b$ where $R_a$ is an alkylene group as defined above containing one to twelve carbon atoms, and Rb is an alkylether group as defined herein. Unless stated otherwise specifically in the specification, an alkoxyalkylether group is optionally substituted, for example substituted with an alcohol or —OP(=$R_a$)($R_b$)$R_c$, wherein each of $R_a$, $R_b$ and $R_c$ is as defined for compounds of structure (I).

"Heteroalkyl" refers to an alkyl group, as defined above, comprising at least one heteroatom (e.g., N, O, P or S) within the alkyl group or at a terminus of the alkyl group. In some embodiments, the heteroatom is within the alkyl group (i.e., the heteroalkyl comprises at least one carbon-[heteroatom]$_x$-carbon bond, where x is 1, 2 or 3). In other embodiments, the heteroatom is at a terminus of the alkyl group and thus serves to join the alkyl group to the remainder of the molecule (e.g., M1-H-A), where M1 is a portion of the molecule, H is a heteroatom and A is an alkyl group). Unless stated otherwise specifically in the specification, a heteroalkyl group is optionally substituted. Exemplary heteroalkyl groups include ethylene oxide (e.g., polyethylene oxide), optionally including phosphorous-oxygen bonds, such as phosphodiester bonds.

"Heteroalkoxy" refers to a group of the formula —$OR_a$ where $R_a$ is a heteroalkyl group as defined above containing one to twelve carbon atoms. Unless stated otherwise specifically in the specification, a heteroalkoxy group is optionally substituted.

"Heteroalkylene" refers to an alkylene group, as defined above, comprising at least one heteroatom (e.g., N, O, P or S) within the alkylene chain or at a terminus of the alkylene chain. In some embodiments, the heteroatom is within the alkylene chain (i.e., the heteroalkylene comprises at least one carbon-[heteroatom]-carbon bond, where x is 1, 2 or 3). In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). Unless stated otherwise specifically in the specification, a heteroalkylene group is optionally substituted. Exemplary heteroalkylene groups include ethylene oxide (e.g., polyethylene oxide) and the "C" linking group illustrated below:

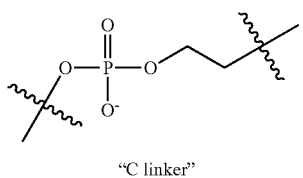 [SMILES: *CCOP(=O)([O-])O*]

"C linker"

Multimers of the above C-linker are included in various embodiments of heteroalkylene linkers.

"Heteroalkenylene" is a heteroalkylene, as defined above, comprising at least one carbon-carbon double bond. Unless stated otherwise specifically in the specification, a heteroalkenylene group is optionally substituted.

"Heteroalkynylene" is a heteroalkylene comprising at least one carbon-carbon triple bond. Unless stated otherwise specifically in the specification, a heteroalkynylene group is optionally substituted.

"Heteroatomic" in reference to a "heteroatomic linker" refers to a linker group consisting of one or more heteroatoms. Exemplary heteroatomic linkers include single atoms selected from the group consisting of O, N, P and S, and multiple heteroatoms for example a linker having the formula —P(O⁻)(=O)O— or —OP(O⁻)(=O)O— and multimers and combinations thereof.

"Phosphate" refers to the —OP(=O)(R$_a$)R$_b$ group, wherein R$_a$ is OH, O⁻ or OR$_c$; and R$_b$ is OH, O⁻, OR$_c$, a thiophosphate group or a further phosphate group, wherein R$_c$ is a counter ion (e.g., Na+ and the like).

"Phosphoalkyl" refers to the —OP(=O)(R$_a$)R$_b$ group, wherein R$_a$ is OH, O⁻ or OR$_c$; and R$_b$ is —Oalkyl, wherein R$_c$ is a counter ion (e.g., Na+ and the like). Unless stated otherwise specifically in the specification, a phosphoalkyl group is optionally substituted. For example, in certain embodiments, the —Oalkyl moiety in a phosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for compounds of structure (I).

"Phosphoalkylether" refers to the —OP(=O)(R$_a$)R$_b$ group, wherein R$_a$ is OH, O⁻ or OR$_c$; and R$_b$ is —Oalkylether, wherein R$_c$ is a counter ion (e.g., Na+ and the like). Unless stated otherwise specifically in the specification, a phosphoalkylether group is optionally substituted. For example, in certain embodiments, the —Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for compounds of structure (I).

"Thiophosphate" refers to the —OP(=R$_a$)(R$_b$)R$_c$ group, wherein R$_a$ is O or S, R$_b$ is OH, O⁻, S⁻, OR$_d$ or SR$_d$; and R$_c$ is OH, SH, O⁻, S⁻, OR$_d$, SR$_d$, a phosphate group or a further thiophosphate group, wherein R$_d$ is a counter ion (e.g., Na+ and the like) and provided that: i) R$_a$ is S; ii) R$_b$ is S⁻ or SR$_d$; iii) R$_c$ is SH, S⁻ or SR$_d$; or iv) a combination of i), ii) and/or iii).

"Thiophosphoalkyl" refers to the —OP(=R$_a$)(R$_b$)R$_c$ group, wherein R$_a$ is O or S, R$_b$ is OH, O⁻, S⁻, OR$_d$ or SR$_d$; and R$_c$ is —Oalkyl, wherein R$_d$ is a counter ion (e.g., Na+ and the like) and provided that: i) R$_a$ is S; ii) R$_b$ is S⁻ or SR$_d$; or is S and R$_b$ is S⁻ or SR$_d$. Unless stated otherwise specifically in the specification, a thiophosphoalkyl group is optionally substituted. For example, in certain embodiments, the —Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for compounds of structure (I).

"Thiophosphoalkylether" refers to the —OP(=R$_a$)(R$_b$)R$_c$ group, wherein R$_a$ is O or S, R$_b$ is OH, O⁻, S⁻, OR$_d$ or SR$_d$; and R$_c$ is —Oalkylether, wherein R$_d$ is a counter ion (e.g., Na+ and the like) and provided that: i) R$_a$ is S; ii) R$_b$ is S⁻ or SR$_d$; or iii)R$_a$ is S and R$_b$ is S⁻ or SR$_d$. Unless stated otherwise specifically in the specification, a thiophosphoalkylether group is optionally substituted. For example, in certain embodiments, the —Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for compounds of structure (I).

"Carbocyclic" refers to a stable 3- to 18-membered aromatic or non-aromatic ring comprising 3 to 18 carbon atoms. Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl. Unless stated otherwise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cyclocalkyls include, for example, cyclopropyl, cyclobutyl, cyclopentyl, cyclohexyl, cycloheptly, and cyclooctyl. Polycyclic cycloalkyls include, for example, adamantyl, norbornyl, decalinyl, 7,7-dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl comprises from 6 to 18 carbon atoms. The aryl ring may be a monocyclic, bicyclic, tricyclic or tetracyclic ring system, which may include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3- to 18-membered aromatic or non-aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclic group is optionally substituted.

"Heteroaryl" refers to a 5- to 14-membered ring system comprising one to thirteen carbon atoms, one to six heteroatoms selected from the group consisting of nitrogen, oxygen and sulfur, and at least one aromatic ring. For purposes of certain embodiments of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group is optionally substituted.

"Fused" refers to a ring system comprising at least two rings, wherein the two rings share at least one common ring atom, for example two common ring atoms. When the fused ring is a heterocyclyl ring or a heteroaryl ring, the common ring atom(s) may be carbon or nitrogen. Fused rings include bicyclic, tricyclic, tertracyclic, and the like.

The term "substituted" used herein means any of the above groups (e.g., alkyl, alkylene, alkenylene, alkynylene, heteroalkylene, heteroalkenylene, heteroalkynylene, alkoxy, alkylether, alkoxyalkylether, heteroalkyl, heteroalkoxy, phosphoalkyl, phosphoalkylether, thiophosphoalkyl, thiophosphoalkylether, carbocyclic, cycloalkyl, aryl, heterocyclic and/or heteroaryl) wherein at least one hydrogen atom (e.g., 1, 2, 3 or all hydrogen atoms) is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In some embodiments, the optional substituent is —OP(=RO(R$_b$)R$_c$, wherein each of R$_a$, R$_b$ and R$^c$ is as defined for compounds of structure (I). In addition, each of the foregoing substituents may also be optionally substituted with one or more of the above substituents.

"Conjugation" refers to the overlap of one p-orbital with another p-orbital across an intervening sigma bond. Conjugation may occur in cyclic or acyclic compounds. A "degree of conjugation" refers to the overlap of at least one p-orbital with another p-orbital across an intervening sigma bond. For example, 1,3-butadiene has one degree of conjugation, while benzene and other aromatic compounds typically have multiple degrees of conjugation. Fluorescent and colored compounds typically comprise at least one degree of conjugation.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

The term "biomolecule" refers to any of a variety of biological materials, including nucleic acids, carbohydrates, amino acids, polypeptides, glycoproteins, hormones, aptamers and mixtures thereof. More specifically, the term is intended to include, without limitation, RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. The visually detectable biomolecules of the invention (e.g., compounds of structure (I) having a biomolecule linked thereto) are prepared, as further described herein, by contacting a biomolecule with a compound having a reactive group that enables attachment of the biomolecule to the compound via any available atom or functional group, such as an amino, hydroxy, carboxyl, or sulfhydryl group on the biomolecule.

A "reactive group" is a moiety capable of reacting with a second reactive groups (e.g., a "complementary reactive group") to form one or more covalent bonds, for example by a displacement, oxidation, reduction, addition or cycloaddition reaction. Exemplary reactive groups are provided in Table 1, and include for example, nucleophiles, electrophiles, dienes, dienophiles, aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin, thiirane and the like.

The terms "visible" and "visually detectable" are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000 $M^{-1}cm^{-1}$. The compounds of the invention may be detected by observation with the naked eye, or with the aid of an optically based detection device, including, without limitation, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of embodiments of the invention, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Nonlimiting examples of photostable visible dyes suitable for use in the compounds and methods of the invention include azo dyes, thioindigo dyes, quinacridone pigments, dioxazine, phthalocyanine, perinone, diketopyrrolopyrrole, quinophthalone, and truarycarbonium.

As used herein, the term "perylene derivative" is intended to include any substituted perylene that is visually detectable. However, the term is not intended to include perylene itself. The terms "anthracene derivative", "naphthalene derivative", and "pyrene derivative" are used analogously. In some preferred embodiments, a derivative (e.g., perylene, pyrene, anthracene or naphthalene derivative) is an imide, bisimide or hydrazamimide derivative of perylene, anthracene, naphthalene, or pyrene.

The visually detectable molecules of various embodiments of the invention are useful for a wide variety of analytical applications, such as biochemical and biomedical applications, in which there is a need to determine the presence, location, or quantity of a particular analyte (e.g., biomolecule). In another aspect, therefore, the invention provides a method for visually detecting a biomolecule, comprising: (a) providing a biological system with a visually detectable biomolecule comprising the compound of structure (I) linked to a biomolecule; and (b) detecting the biomolecule by its visible properties. For purposes of the invention, the phrase "detecting the biomolecule by its visible properties" means that the biomolecule, without illumination or chemical or enzymatic activation, is observed with the naked eye, or with the aid of a optically based detection device, including, without limitation, absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Nonlimiting examples of such biological systems include cells, cell extracts, tissue samples, electrophoretic gels, assay mixtures, and hybridization reaction mixtures.

"Solid support" refers to any solid substrate known in the art for solid-phase support of molecules, for example a "microparticle" refers to any of a number of small particles useful for attachment to compounds of the invention, including, but not limited to, glass beads, magnetic beads, polymeric beads, nonpolymeric beads, and the like. In certain embodiments, a microparticle comprises polystyrene beads.

A "solid support reside" refers to the functional group remaining attached to a molecule when the molecule is cleaved from the solid support. Solid support residues are known in the art and can be easily derived based on the structure of the solid support and the group linking the molecule thereto.

A "targeting moiety" is a moiety that selectively binds or associates with a particular target, such as an analyte molecule. "Selectively" binding or associating means a targeting moiety preferentially associates or binds with the desired target relative to other targets. In some embodiments the compounds disclosed herein include linkages to targeting moieties for the purpose of selectively binding or associating the compound with an analyte of interest (i.e., the target of the targeting moiety), thus allowing detection of the analyte. Exemplary targeting moieties include, but are not limited to, antibodies, antigens, nucleic acid sequences, enzymes, proteins, cell surface receptor antagonists, and the like. In some embodiments, the targeting moiety is a moiety, such as an antibody, that selectively binds or associates with a target feature on or in a cell, for example a target feature on a cell membrane or other cellular structure, thus allowing for detection of cells of interest. Small molecules that selectively bind or associate with a desired analyte are also contemplated as targeting moieties in certain embodiments. One of skill in the art will understand other analytes, and the corresponding targeting moiety, that will be useful in various embodiments.

"Base pairing moiety" refers to a heterocyclic moiety capable of hybridizing with a complementary heterocyclic moiety via hydrogen bonds (e.g., Watson-Crick base pairing). Base pairing moieties include natural and unnatural bases. Non-limiting examples of base pairing moieties are RNA and DNA bases such adenosine, guanosine, thymidine, cytosine and uridine and analogues thereof.

Embodiments of the invention disclosed herein are also meant to encompass all compounds of structure (I) or (II) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively.

Isotopically-labeled compounds of structure (I) or (II) can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution.

"Salt" includes both acid and base addition salts.

"Acid addition salt" refers to those salts which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Crystallizations may produce a solvate of the compounds described herein. Embodiments of the present invention include all solvates of the described compounds. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases the compounds of the invention may merely retain adventitious water or another solvent or be a mixture of water plus some adventitious solvent.

Embodiments of the compounds of the invention (e.g., compounds of structure I or II), or their salts, tautomers or solvates may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. Embodiments of the present invention are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds. Various tautomeric forms of the compounds are easily derivable by those of ordinary skill in the art.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

As noted above, in one embodiment of the present invention, compounds useful as fluorescent and/or colored dyes in various analytical methods are provided. In other embodiments, compounds useful as synthetic intermediates for preparation of compounds useful as fluorescent and/or colored dyes are provided. In general terms, embodiments of the present invention are directed to dimers and higher polymers of fluorescent and/or colored moieties. The fluorescent and or colored moieties are linked by a linking moiety. Without wishing to be bound by theory, it is believed the linker helps to maintain sufficient spatial distance between the fluorescent and/or colored moieties such that intramolecular quenching is reduced or eliminated, thus resulting in a dye compound having a high molar "brightness" (e.g., high fluorescence emission).

Accordingly, in some embodiments the compounds have the following structure (A):

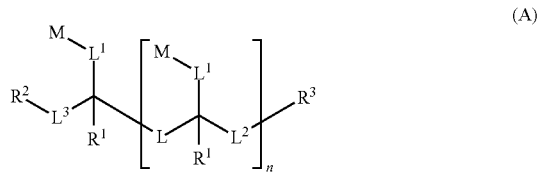

wherein L is a linker sufficient to maintain spatial separation between one or more (e.g., each) M group so that intramolecular quenching is reduced or eliminated, and $R^1$, $R^2$, $R^3$, $L^1$, $L^2$, $L^3$ and n are as defined for structure (I). In some embodiments of structure (A), L is a linker comprising one or more ethylene glycol or polyethylene glycol moieties.

In other embodiments is provided a compound having the following structure (I):

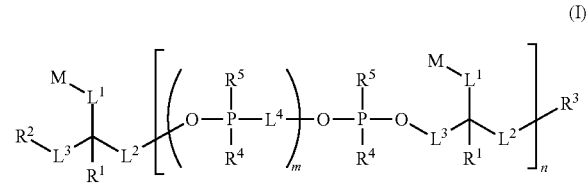

or a stereoisomer, salt or tautomer thereof, wherein:

M is, at each occurrence, independently a moiety comprising two or more carbon-carbon double bonds and at least one degree of conjugation;

$L^1$ is at each occurrence, independently either: i) an optional alkylene, alkenylene, alkynylene, heteroalkylene, heteroalkenylene, heteroalkynylene or heteroatomic linker; or ii) a linker comprising a functional group capable of formation by reaction of two complementary reactive groups;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently a heteroalkylene, heteroalkenylene or heteroalkynylene linker of greater than three atoms in length, wherein the heteroatoms in the heteroalkylene, heteroalkenylene and heteroalkynylene linker are selected from O, N and S;

$R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q or L';

$R^4$ is, at each occurrence, independently OH, SH, O⁻, S⁻, O$R_d$ or S$R_d$;

$R^5$ is, at each occurrence, independently oxo, thioxo or absent;

$R_a$ is O or S;

$R_b$ is OH, SH, O⁻, S⁻, O$R_d$ or S$R_d$;

$R_c$ is OH, SH, O⁻, S⁻, O$R_d$, OL', S$R_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected analogue thereof, capable of forming a covalent bond with an analyte molecule, a targeting moiety, a solid support or a complementary reactive group Q;

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, independently an integer of zero or greater, provided that at least one occurrence of m is an integer of one or greater; and n is an integer of one or greater.

In different embodiments of the compound of structure (I):

M is, at each occurrence, independently a moiety comprising two or more carbon-carbon double bonds and at least one degree of conjugation;

$L^1$ is at each occurrence, independently either: i) an optional alkylene, alkenylene, alkynylene, heteroalkylene, heteroalkenylene, heteroalkynylene or heteroatomic linker; or ii) a linker comprising a functional group capable of formation by reaction of two complementary reactive groups;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently a heteroalkylene, heteroalkenylene or heteroalkynylene linker of greater than three atoms in length, wherein the heteroatoms in the heteroalkylene, heteroalkenylene and heteroalkynylene linker are selected from O, N and S;

$R^1$ is, at each occurrence, independently H, alkyl or alkoxy;

$R^2$ and $R^3$ are each independently H, OH, SH, alkyl, alkoxy, alkylether, —OP(=$R_a$)($R_b$)$R_c$, Q, a linker comprising a covalent bond to Q, a linker comprising a covalent bond to an analyte molecule, a linker comprising a covalent bond to a solid support or a linker comprising a covalent bond to a further compound of structure (I), wherein: $R_a$ is O or S; $R_b$ is OH, SH, O⁻, S⁻, $OR_d$ or $SR_d$; $R_c$ is OH, SH, O⁻, S⁻, $OR_d$, $SR_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;

$R^4$ is, at each occurrence, independently OH, SH, O⁻, S⁻, $OR_d$ or $SR_d$;

$R^5$ is, at each occurrence, independently oxo, thioxo or absent;

Q is, at each occurrence, independently a moiety comprising a reactive group capable of forming a covalent bond with an analyte molecule, a solid support or a complementary reactive group Q';

m is, at each occurrence, independently an integer of zero or greater, provided that at least one occurrence of m is an integer of one or greater; and n is an integer of one or greater.

The various linkers and substituents (e.g., M, Q, $R^1$, $R^2$, $R^3$, $R^c$ $L^1$, $L^2$, $L^3$ and $L^4$) in the compound of structure (I) are optionally substituted with one more substituent. For example, in some embodiments the optional substituent is selected to optimize the water solubility or other property of the compound of structure (I). In certain embodiments, each alkyl, alkoxy, alkylether, alkoxyalkylether, phosphoalkyl, thiophosphoalkyl, phosphoalkylether and thiophosphoalkylether in the compound of structure (I) is optionally substituted with one more substituent selected from the group consisting of hydroxyl, alkoxy, alkylether, alkoxyalkylether, sulfhydryl, amino, alkylamino, carboxyl, phosphate, thiophosphate, phosphoalkyl, thiophosphoalkyl, phosphoalkylether and thiophosphoalkylether. In certain embodiments the optional substituent is —OP(=$R_a$)($R_b$)$R_c$, where $R_a$, $R_b$ and $R_c$ are as defined for the compound of structure (I).

In some embodiments, $L^1$ is at each occurrence, independently an optional alkylene, alkenylene, alkynylene, heteroalkylene, heteroalkenylene, heteroalkynylene or heteroatomic linker. In other embodiments, $L^1$ is at each occurrence, independently a linker comprising a functional group capable of formation by reaction of two complementary reactive groups, for example a Q group.

In some embodiments, $L^4$ is at each occurrence, independently a heteroalkylene linker. In other more specific embodiments, $L^4$ is at each occurrence, independently an alkylene oxide linker. For example, in some embodiments $L^4$ is polyethylene oxide, and the compound has the following structure (IA):

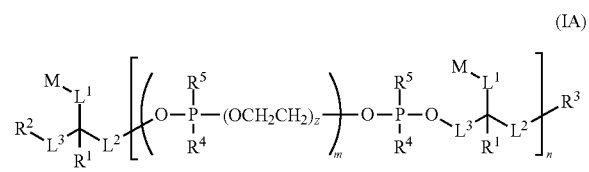

(IA)

wherein z is an integer from 2 to 100. In some embodiments of (IA), z is an integer from 2-30, for example from about 20 to 25, or about 23. In some embodiments, z is an integer from 2 to 10, for example from 3 to 6. In some embodiments, z is 3. In some embodiments, z is 4. In some embodiments, z is 5. In some embodiments, z is 6.

The optional linker $L^1$ can be used as a point of attachment of the M moiety to the remainder of the compound. For example, in some embodiments a synthetic precursor to the compound of structure (I) is prepared, and the M moiety is attached to the synthetic precursor using any number of facile methods known in the art, for example methods referred to as "click chemistry." For this purpose any reaction which is rapid and substantially irreversible can be used to attach M to the synthetic precursor to form a compound of structure (I). Exemplary reactions include the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse-demand Diels-Alder, alkene and tetrazole photoreaction and various displacement reactions, such as displacement of a leaving group by nucleophilic attack on an electrophilic atom. Exemplary displacement reactions include reaction of an amine with: an activated ester; an N-hydroxysuccinimide ester; an isocyanate; an isothiocyanate or the like. In some embodiments the reaction to form $L^1$ may be performed in an aqueous environment.

Accordingly, in some embodiments $L^1$ is at each occurrence a linker comprising a functional group capable of formation by reaction of two complementary reactive groups, for example a functional group which is the product of one of the foregoing "click" reactions. In various embodiments, for at least one occurrence of $L^1$, the functional group can be formed by reaction of an aldehyde, oxime, hydrazone, alkyne, amine, azide, acylazide, acylhalide, nitrile, nitrone, sulfhydryl, disulfide, sulfonyl halide, isothiocyanate, imidoester, activated ester (e.g., N-hydroxysuccinimide ester), ketone, α,β-unsaturated carbonyl, alkene, maleimide, α-haloimide, epoxide, aziridine, tetrazine, tetrazole, phosphine, biotin or thiirane functional group with a complementary reactive group. For example, reaction of an amine with an N-hydroxysuccinimide ester or isothiocyanate.

In other embodiments, for at least one occurrence of $L^1$, the functional group can be formed by reaction of an alkyne and an azide. In other embodiments, for at least one occurrence of $L^1$, the functional group can be formed by reaction of an amine (e.g., primary amine) and an N-hydroxysuccinimide ester or isothiocyanate.

In more embodiments, for at least one occurrence of $L^1$, the functional group comprises an alkene, ester, amide, thioester, disulfide, carbocyclic, heterocyclic or heteroaryl group. In more embodiments, for at least one occurrence of $L^1$, the functional group comprises an alkene, ester, amide, thioester, thiourea, disulfide, carbocyclic, heterocyclic or heteroaryl group. In other embodiments, the functional group comprises an amide or thiourea. In some more specific embodiments, for at least one occurrence of $L^1$, $L^1$ is a linker comprising a triazolyl functional group. While in other embodiments, for at least one occurrence of $L^1$, $L^1$ is a linker comprising an amide or thiourea functional group.

In still other embodiments, for at least one occurrence of $L^1$, $L^1$-M has the following structure:

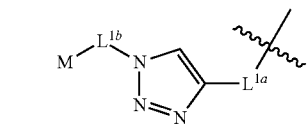

wherein $L^{1a}$ and $L^{1b}$ are each independently optional linkers.

In different embodiments, for at least one occurrence of $L^1$, $L^1$-M has the following structure:

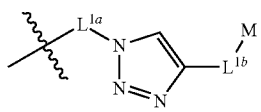

wherein $L^{1a}$ and $L^{1b}$ are each independently optional linkers.

In various embodiments of the foregoing, $L^{1a}$ or $L^{1b}$, or both, is absent. In other embodiments, $L^{1a}$ or $L^{1b}$, or both, is present.

In some embodiments $L^{1a}$ and $L^{1b}$, when present, are each independently alkylene or heteroalkylene. For example, in some embodiments $L^{1a}$ and $L^{1b}$, when present, independently have one of the following structures:

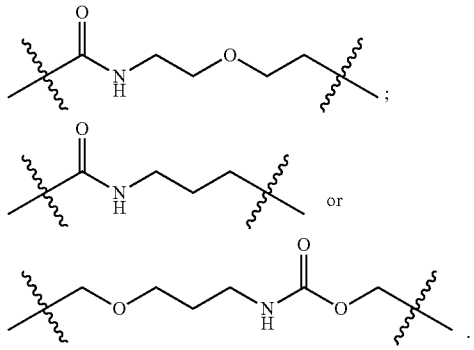

In still other different embodiments of structure (I), $L^1$ is at each occurrence, independently an optional alkylene or heteroalkylene linker. In certain embodiments, $L^1$ has one of the following structures:

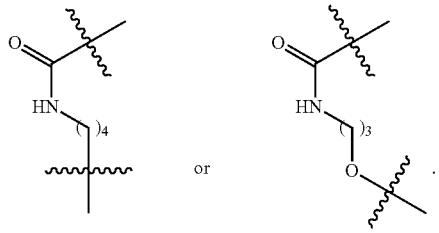

In more embodiments, $L^2$ and $L^3$ are, at each occurrence, independently $C_1$-$C_6$ alkylene, $C_2$-$C_6$ alkenylene or $C_2$-$C_6$ alkynylene. For example, in some embodiments the compound has the following structure (IB):

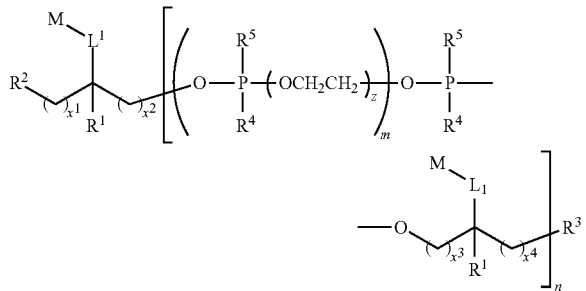

wherein:

$x^1$, $x^2$, $x^3$ and $x^4$ are, at each occurrence, independently an integer from 0 to 6; and z is an integer from 2 to 100, for example from 3 to 6.

In certain embodiments of the compound of structure (TB), at least one occurrence of $x^1$, $x^2$, $x^3$ or $x^4$ is 1. In other embodiments, $x^1$, $x^2$, $x^3$ and $x^4$ are each 1 at each occurrence. In other embodiments, $x^1$ and $x^3$ are each 0 at each occurrence. In some embodiments, $x^2$ and $x^4$ are each 1 at each occurrence. In still other embodiments, $x^1$ and $x^3$ are each 0 at each occurrence, and $x^2$ and $x^4$ are each 1 at each occurrence.

In some more specific embodiments of the compound of structure (TB), $L^1$, at each occurrence, independently comprises a triazolyl functional group. In some other specific embodiments of the compound of structure (IB), $L^1$, at each occurrence, independently comprises an amide or thiourea functional group. In other embodiments of the compound of structure (IB), $L^1$, at each occurrence, independently an optional alkylene or heteroalkylene linker.

In still other embodiments of any of the compounds of structure (I), $R^4$ is, at each occurrence, independently OH, O⁻ or $OR_d$. It is understood that "$OR_d$" and "$SR_d$" are intended to refer to O⁻ and S⁻ associated with a cation. For example, the disodium salt of a phosphate group may be represented as:

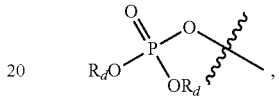

where $R_d$ is sodium (Na⁺).

In other embodiments of any of the compounds of structure (I), $R^5$ is, at each occurrence, oxo.

In some different embodiments of any of the foregoing compounds, $R^1$ is H.

In other various embodiments, $R^2$ and $R^3$ are each independently OH or —OP(=$R_a$)($R_b$)$R_c$. In some different embodiments, $R^2$ or $R^3$ is OH or —OP(=$R_a$)($R_b$)$R_c$, and the other of $R^2$ or $R^3$ is Q or a linker comprising a covalent bond to Q.

In still more different embodiments of any of the foregoing compounds of structure (I), $R^2$ and $R^3$ are each independently —OP(=$R_a$)($R_b$)$R_c$. In some of these embodiments, $R_c$ is OL'.

In other embodiments, $R^2$ and $R^3$ are each independently —OP(=$R_a$)($R_b$)OL', and L' is an alkylene or heteroalkylene linker to: Q, a targeting moiety, an analyte (e.g., analyte molecule), a solid support, a solid support residue, a nucleoside or a further compound of structure (I).

The linker L' can be any linker suitable for attaching Q, a targeting moiety, an analyte (e.g., analyte molecule), a solid support, a solid support residue, a nucleoside or a further compound of structure (I) to the compound of structure (I). Advantageously certain embodiments include use of L' moieties selected to increase or optimize water solubility of the compound. In certain embodiments, L' is a heteroalkylene moiety. In some other certain embodiments, L' comprises an alkylene oxide or phosphodiester moiety, or combinations thereof.

In certain embodiments, L' has the following structure:

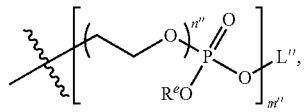

wherein:

m" and n" are independently an integer from 1 to 10;

$R^e$ is H, an electron pair or a counter ion;

L" is $R^e$ or a direct bond or linkage to: Q, a targeting moiety, an analyte (e.g., analyte molecule), a solid support, a solid support residue, a nucleoside or a further compound of structure (I).

In some embodiments, m" is an integer from 4 to 10, for example 4, 6 or 10. In other embodiments n" is an integer from 3 to 6, for example 3, 4, 5 or 6.

In some other embodiments, L″ is an alkylene or heteroalkylene moiety. In some other certain embodiments, L″ comprises an alkylene oxide, phosphodiester moiety, sulfhydryl, disulfide or maleimide moiety or combinations thereof.

In certain of the foregoing embodiments, the targeting moiety is an antibody or cell surface receptor antagonist.

In other more specific embodiments of any of the foregoing compounds of structure (I), $R^2$ or $R^3$ has one of the following structures:

Certain embodiments of compounds of structure (I) can be prepared according to solid-phase synthetic methods analogous to those known in the art for preparation of oligonucleotides. Accordingly, in some embodiments, L′ is a linkage to a solid support, a solid support residue or a nucleoside. Solid supports comprising an activated deoxythymidine (dT) group are readily available, and in some embodiments can be employed as starting material for preparation of compounds of structure (I). Accordingly, in some embodiments $R^2$ or $R^3$ has the following structure:

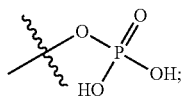

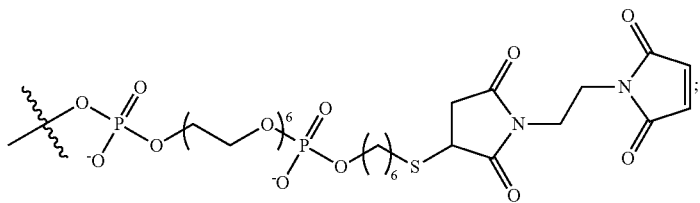

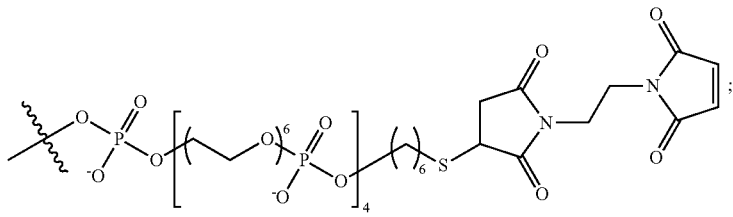

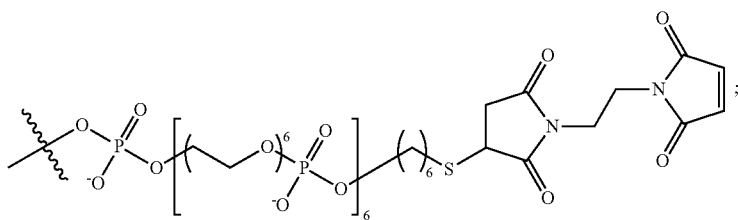

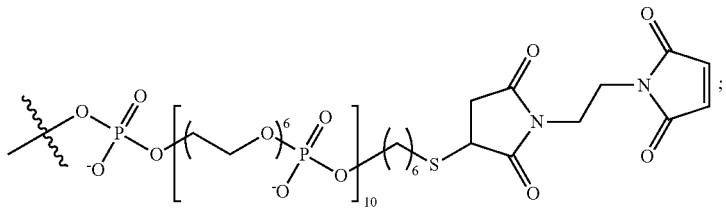

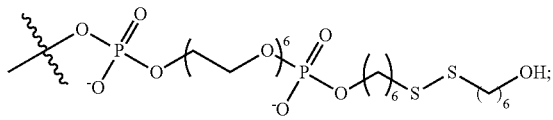

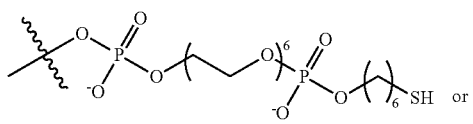

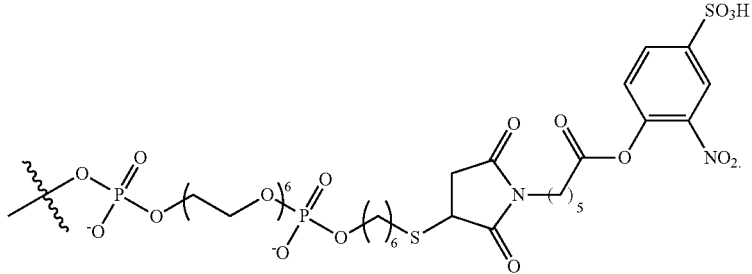

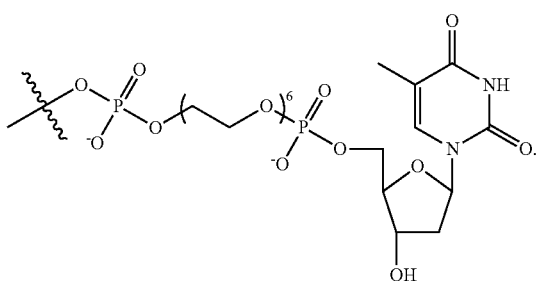

One of skill in the art will understand that the dT group depicted above is included for ease of synthesis and economic efficiencies only, and is not required. Other solid supports can be used and would result in a different nucleoside or solid support residue being present on L', or the nucleoside or solid support residue can be removed or modified post synthesis.

In still other embodiments, Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'. For example, in some embodiments, Q' is present on a further compound of structure (I) (e.g., in the $R^2$ or $R^3$ position), and Q and Q' comprise complementary reactive groups such that reaction of the compound of structure (I) and the further compound of structure (I) results in covalently bound dimer of the compound of structure (I). Multimer compounds of structure (I) can also be prepared in an analogous manner and are included within the scope of embodiments of the invention.

The type of Q group and connectivity of the Q group to the remainder of the compound of structure (I) is not limited, provided that Q comprises a moiety having appropriate reactivity for forming the desired bond.

In certain embodiments, Q is a moiety which is not susceptible to hydrolysis under aqueous conditions, but is sufficiently reactive to form a bond with a corresponding group on an analyte molecule or solid support (e.g., an amine, azide or alkyne).

Certain embodiments of compounds of structure (I) comprise Q groups commonly employed in the field of bioconjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group. In some embodiments, the activated ester is an N-succinimide ester, imidoester or polyflourophenyl ester. In other embodiments, the alkyne is an alkyl azide or acyl azide.

The Q groups can be conveniently provided in protected form to increase storage stability or other desired properties, and then the protecting group removed at the appropriate time for conjugation with, for example, a targeting moiety or analyte. Accordingly, Q groups include "protected forms" of a reactive group, including any of the reactive groups described above and in the Table 1 below. A "protected form" of Q refers to a moiety having lower reactivity under predetermined reaction conditions relative to Q, but which can be converted to Q under conditions, which preferably do not degrade or react with other portions of the compound of structure (I). One of skill in the art can derive appropriate protected forms of Q based on the particular Q and desired end use and storage conditions. For example, when Q is SH, a protected form of Q includes a disulfide, which can be reduce to reveal the SH moiety using commonly known techniques and reagents.

Exemplary Q moieties are provided in Table I below.

TABLE 1

Exemplary Q Moieties

| Structure | Class |
|---|---|
| —SH | Sulfhydryl |
| —N=C=S | Isothiocyanate |
| imidoester structure | Imidoester |
| acyl azide structure | Acyl Azide |
| tetrafluorophenyl ester | Activated Ester |
| pentafluorophenyl ester | Activated Ester |
| sulfo-nitrophenyl ester | Activated Ester |
| sulfo-SMCC type ester | Activated Ester |

TABLE 1-continued

Exemplary Q Moieties

| Structure | Class |
|---|---|
| (activated ester with NHS) | Activated Ester |
| (sulfo-NHS activated ester) | Activated Ester |
| —S(O)₂—X, X = halo | Sulfonyl halide |
| (maleimide) | Maleimide |
| (thiol-maleimide with ethylene-maleimide) | Maleimide |
| (cyclohexane amide maleimide, SMCC-type) | Maleimide |
| —NHC(O)CH₂—X, X = halo | α-haloimide |
| (pyridyl disulfide) | Disulfide |
| (phosphine ester, Staudinger) | Phosphine |
| —N₃ | Azide |
| (alkyne) | Alkyne |
| (biotin) | Biotin |
| (diene) | Diene |
| (alkene) | Alkene/ dienophile |
| (alkene-EWG) | Alkene/ dienophile |
| —NH₂ | Amino |

EWG = electron withdrawing group

It should be noted that in some embodiments, wherein Q is SH, the SH moiety will tend to form disulfide bonds with another sulfhydryl group, for example on another compound of structure (I). Accordingly, some embodiments include compounds of structure (I), which are in the form of disulfide dimers, the disulfide bond being derived from SH Q groups.

Also included within the scope of certain embodiments are compounds of structure (I), wherein one, or both, of $R^2$ and $R^3$ comprises a linkage to a further compound of structure (I). For example, wherein one or both of $R^2$ and $R^3$ are —OP(=$R_a$)($R_b$)$R_c$, and Rc is OL', and L' is a linker comprising a covalent bond to a further compound of structure (I). Such compounds can be prepared by preparing a first compound of structure (I) having for example about 10 "M" moieties (i.e., n=9) and having an appropriate "Q" for reaction with a complementary Q' group on a second compound of structure (I). In this manner, compounds of structure (I), having any number of "M" moieties, for example 100 or more, can be prepared without the need for sequentially coupling each monomer. Exemplary embodiments of such compounds of structure (I) have the following structure (I')

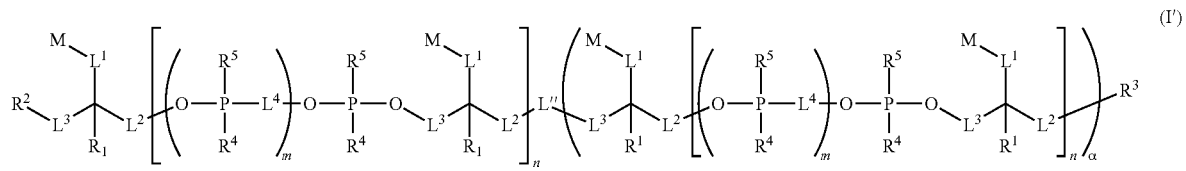

(I')

wherein:

each occurrence of $R^1$, $R^2$, $R^3$, $R^4$, $R^5$, $L^1$, $L^2$, $L^3$, $L^4$, M, m and n are independently as defined for a compound of structure (I);

L" is a linker comprising a functional group resulting from reaction of a Q moiety with a corresponding Q' moiety; and α is an integer greater than 1, for example from 1 to 100, or 1 to 10.

An exemplary compound of structure (I') is provided in Example 5. Other compounds of structure (I') are derivable by those of ordinary skill in the art, for example by dimerizing or polymerizing compounds of structure (I) provided herein.

In other embodiments, the Q moiety is conveniently masked (e.g., protected) as a disulfide moiety, which can later be reduced to provide an activated Q moiety for binding to a desired analyte molecule or targeting moiety. For example, the Q moiety may be masked as a disulfide having the following structure:

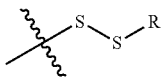

wherein R is an optionally substituted alkyl group. For example, in some embodiments, Q is provided as a disulfide moiety having the following structure:

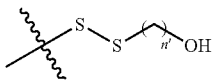

where n is an integer from 1 to 10, for example 6.

In some other embodiments, one of $R^2$ or $R^3$ is OH or $-OP(=R_a)(R_b)R_c$, and the other of $R^2$ or $R^3$ is a linker comprising a covalent bond to an analyte molecule or a linker comprising a covalent bond to a solid support. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In still different embodiments, the solid support is a polymeric bead or nonpolymeric bead.

The value for m is another variable that can be selected based on the desired fluorescence and/or color intensity. In some embodiments, m is, at each occurrence, independently an integer from 1 to 10. In other embodiments, m is, at each occurrence, independently an integer from 1 to 5, for example 1, 2, 3, 4 or 5.

In other embodiments, m is, at each occurrence, independently an integer greater than 2, and z is an integer from 3 to 10, for example in some embodiment m is, at each occurrence, independently an integer greater than 2, such as 3, 4, 5 or 6, and z is an integer from 3 to 6.

The fluorescence intensity can also be tuned by selection of different values of n. In certain embodiments, n is an integer from 1 to 100. In other embodiments, n is an integer from 1 to 10. In some embodiments n is 1. In some embodiments n is 2. In some embodiments n is 3. In some embodiments n is 4. In some embodiments n is 5. In some embodiments n is 6. In some embodiments n is 7. In some embodiments n is 8. In some embodiments n is 9. In some embodiments n is 10.

M is selected based on the desired optical properties, for example based on a desired color and/or fluorescence emission wavelength. In some embodiments, M is the same at each occurrence; however, it is important to note that each occurrence of M need not be an identical M, and certain embodiments include compounds wherein M is not the same at each occurrence. For example, in some embodiments each M is not the same and the different M moieties are selected to have absorbance and/or emissions for use in fluorescence resonance energy transfer (FRET) methods. For example, in such embodiments the different M moieties are selected such that absorbance of radiation at one wavelength causes emission of radiation at a different wavelength by a FRET mechanism. Exemplary M moieties can be appropriately selected by one of ordinary skill in the art based on the desired end use. Exemplary M moieties for FRET methods include fluorescein and 5-TAMRA (5-carboxytetramethylrhodamine, succinimidyl ester) dyes.

M may be attached to the remainder of the molecule from any position (i.e., atom) on M. One of skill in the art will recognize means for attaching M to the remainder of molecule. Exemplary methods include the "click" reactions described herein.

In some embodiments, M is a fluorescent or colored moiety. Any fluorescent and/or colored moiety may be used, for examples those known in the art and typically employed in colorimetric, UV, and/or fluorescent assays may be used. Examples of M moieties which are useful in various embodiments of the invention include, but are not limited to: Xanthene derivatives (e.g., fluorescein, rhodamine, Oregon green, eosin or Texas red); Cyanine derivatives (e.g., cyanine, indocarbocyanine, oxacarbocyanine, thiacarbocyanine or merocyanine); Squaraine derivatives and ring-substituted squaraines, including Seta, SeTau, and Square dyes; Naphthalene derivatives (e.g., dansyl and prodan derivatives); Coumarin derivatives; oxadiazole derivatives (e.g., pyridyloxazole, nitrobenzoxadiazole or benzoxadiazole); Anthracene derivatives (e.g., anthraquinones, including DRAQ5, DRAQ7 and CyTRAK Orange); Pyrene derivatives such as cascade blue; Oxazine derivatives (e.g., Nile red, Nile blue, cresyl violet, oxazine 170); Acridine derivatives (e.g., proflavin, acridine orange, acridine yellow); Arylmethine derivatives: auramine, crystal violet, malachite green; and Tetrapyrrole derivatives (e.g., porphin, phthalocyanine or bilirubin). Other exemplary M moieties include: Cyanine dyes, xanthate dyes (e.g., Hex, Vic, Nedd, Joe or Tet); Yakima yellow; Redmond red; tamra; texas red and Alexa Fluor® dyes.

In still other embodiments of any of the foregoing, M comprises three or more aryl or heteroaryl rings, or combinations thereof, for example four or more aryl or heteroaryl rings, or combinations thereof, or even five or more aryl or heteroaryl rings, or combinations thereof. In some embodiments, M comprises six aryl or heteroaryl rings, or combinations thereof. In further embodiments, the rings are fused. For example in some embodiments, M comprises three or more fused rings, four or more fused rings, five or more fused rings, or even six or more fused rings.

In some embodiments, M is cyclic. For example, in some embodiments M is carbocyclic. In other embodiment, M is heterocyclic. In still other embodiments of the foregoing, M, at each occurrence, independently comprises an aryl moiety. In some of these embodiments, the aryl moiety is multicyclic. In other more specific examples, the aryl moiety is a fused-multicyclic aryl moiety, for example which may comprise at least 3, at least 4, or even more than 4 aryl rings.

In other embodiments of any of the foregoing compounds of structure (I), (IA), (IB) or (I'), M, at each occurrence, independently comprises at least one heteroatom. For example, in some embodiments, the heteroatom is nitrogen, oxygen or sulfur.

In still more embodiments of any of the foregoing, M, at each occurrence, independently comprises at least one substituent. For example, in some embodiments the substituent is a fluoro, chloro, bromo, iodo, amino, alkylamino, arylamino, hydroxy, sulfhydryl, alkoxy, aryloxy, phenyl, aryl, methyl, ethyl, propyl, butyl, isopropyl, t-butyl, carboxy, sulfonate, amide, or formyl group.

In some even more specific embodiments of the foregoing, M, at each occurrence, independently is a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9, 10-ethynylanthracene or ter-naphthyl moiety. In other embodiments, M is, at each occurrence, independently p-terphenyl, perylene, azobenzene, phenazine, phenanthroline, acridine, thioxanthrene, chrysene, rubrene, coronene, cyanine, perylene imide, or perylene amide or a derivative thereof. In still more embodiments, M is, at each occurrence, independently a coumarin dye, resorufin dye, dipyrromethenoboron difluoride dye, ruthenium bipyridyl dye, energy transfer dye, thiazole orange dye, polymethine or N-aryl-1,8-naphthalimide dye.

In still more embodiments of any of the foregoing, M at each occurrence is the same. In other embodiments, each M is different. In still more embodiments, one or more M is the same and one or more M is different.

In some embodiments, M is pyrene, perylene, perylene monoimide or 6-FAM or a derivative thereof. In some other embodiments, M has one of the following structures:

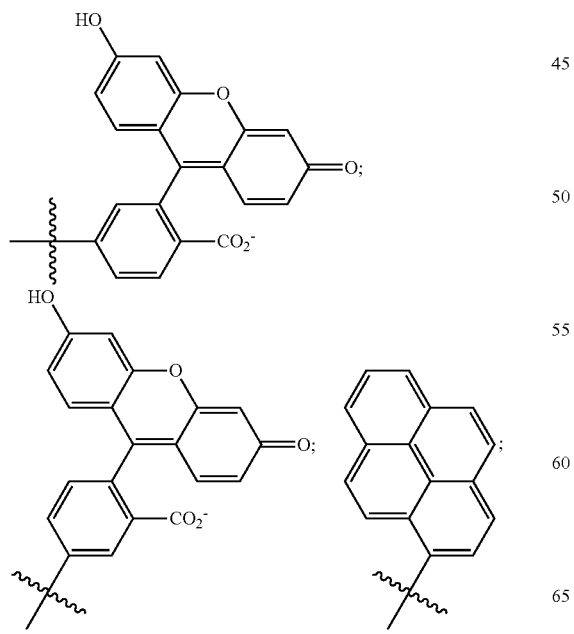

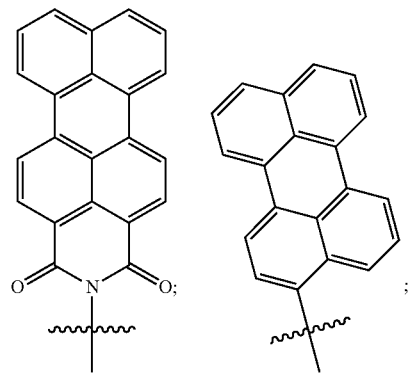

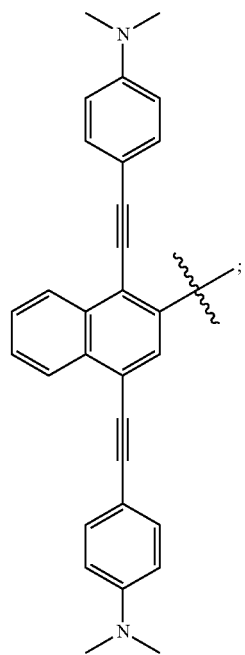

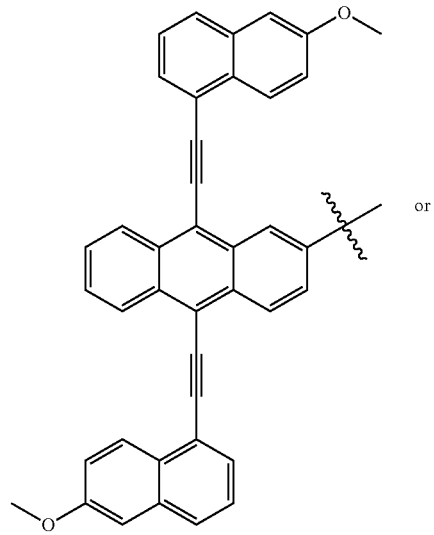

-continued

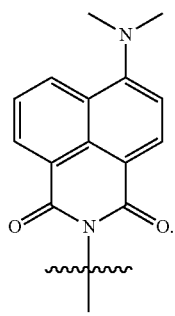

Although M moieties comprising carboxylic acid groups are depicted in the anionic form ($CO_2^-$) above, one of skill in the art will understand that this will vary depending on pH, and the protonated form ($CO_2H$) is included in various embodiments.

In some specific embodiments, the compound is a compound selected from Table 2. The compounds in Table 2 were prepared according to the procedures set forth in the Examples and their identity confirmed by mass spectrometry.

TABLE 2

Exemplary Compounds of Structure I

| No. | MW. Found Calc. | Structure |
|---|---|---|
| I-1 | 1364.6 1365.2 | 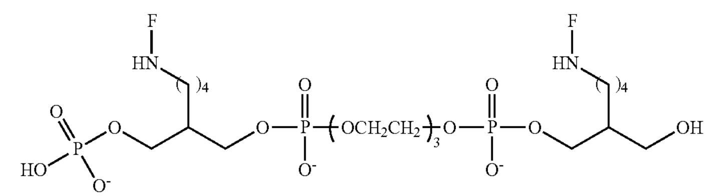 |
| I-2 | 1576.2 1577.3 | 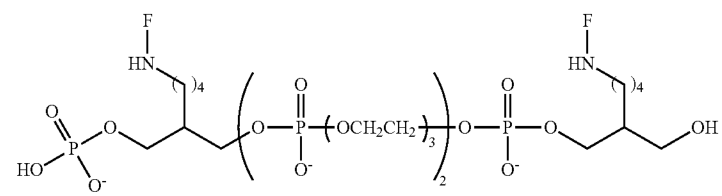 |
| I-3 | 1497.4 1497.3 | 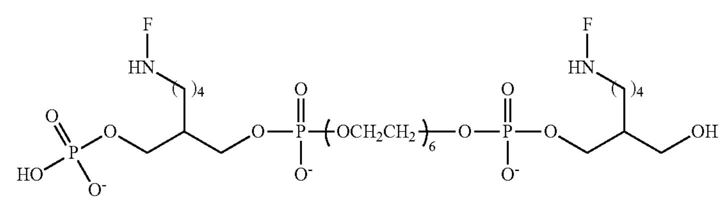 |
| I-4 | 1841.4 1841.6 | 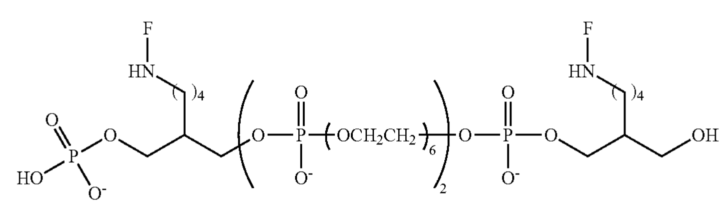 |
| I-5 | 2185.8 2185.9 | 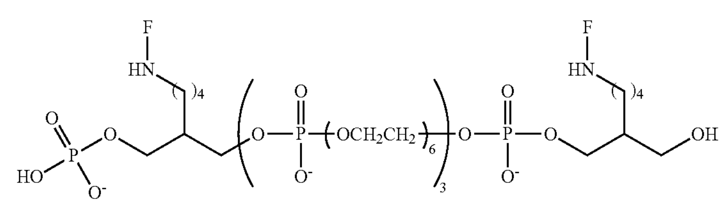 |

TABLE 2-continued

Exemplary Compounds of Structure I

| No. | MW. Found Calc. | Structure |
|---|---|---|
| I-6 | 2532.2 / 2530.2 | 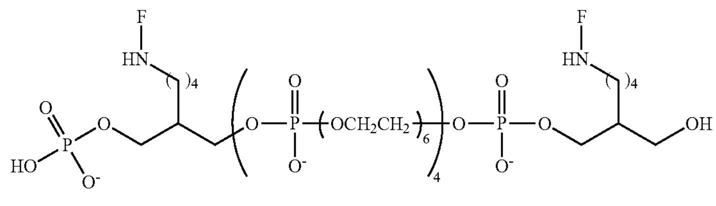 |
| I-7 | 1789.6 / 1789.5 | 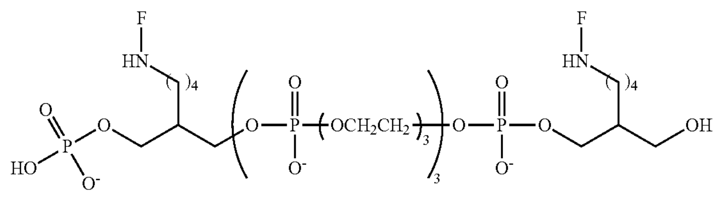 |
| I-8 | 2001.6 / 2001.6 | 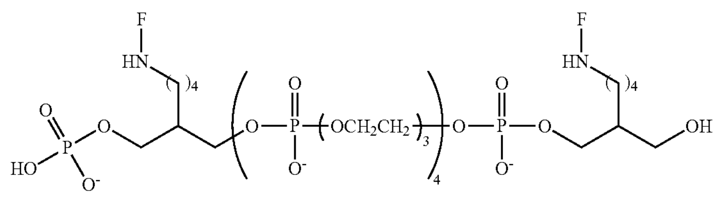 |
| I-9 | 2213.5 / 2213.8 | 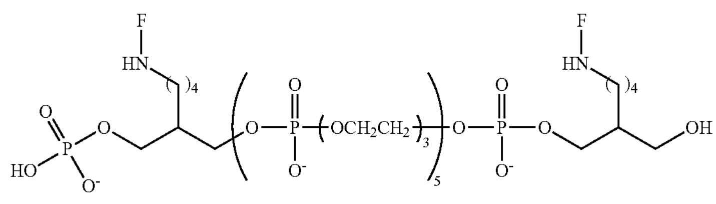 |
| I-10 | 4481.6 / 4480.9 | 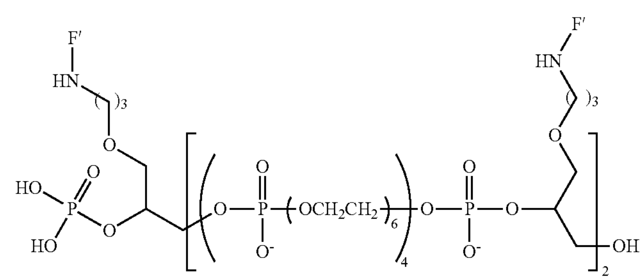 |
| I-11 | 8375.9 / 8374.3 | 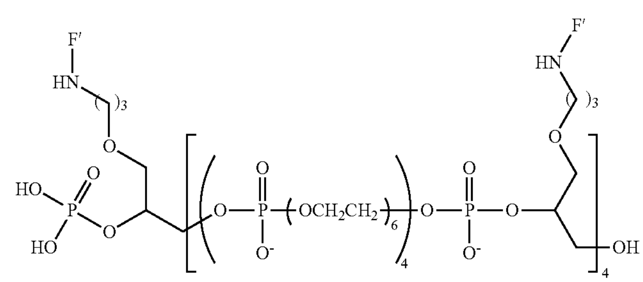 |

TABLE 2-continued
Exemplary Compounds of Structure I
| No. | MW. Found Calc. | Structure |
|---|---|---|
| I-12 | TBD | 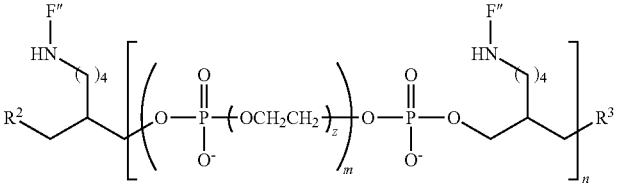 z = 3, 4, 5 or 6<br>m = 2, 3, 4 or 5<br>n = 1-10 |
| I-13 | TBD | 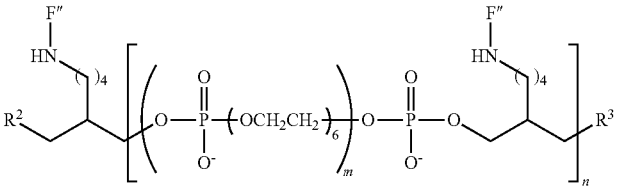 |
| I-14 | TBD | 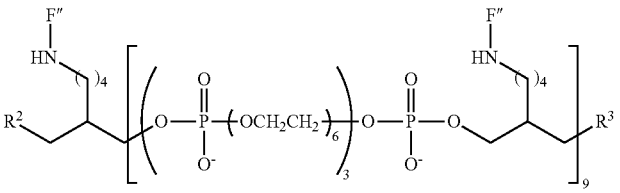 |
| I-15 | TBD | 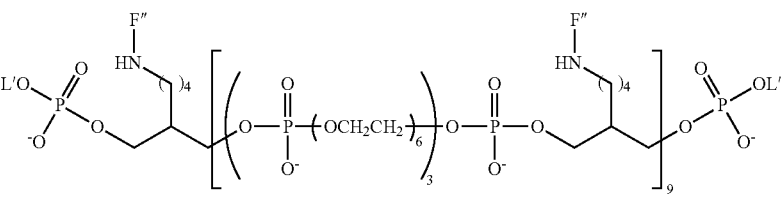 |
| I-16 | TBD | 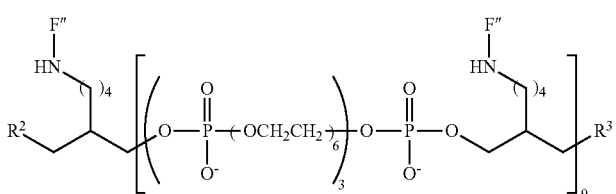 |
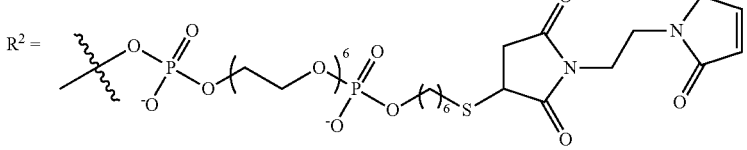
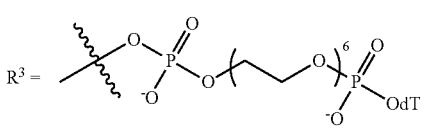

TABLE 2-continued

Exemplary Compounds of Structure I

| No. | MW. Found Calc. | Structure |
|---|---|---|
| I-17 | 15684.6 15681.5 | |
| I-18 | TBD | |

TABLE 2-continued
Exemplary Compounds of Structure I
| No. | MW. Found Calc. | Structure |
|---|---|---|
| I-19 | TBD | 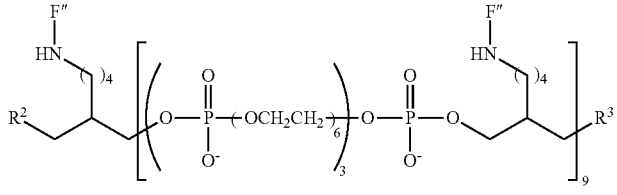 |
| I-20 | TBD | 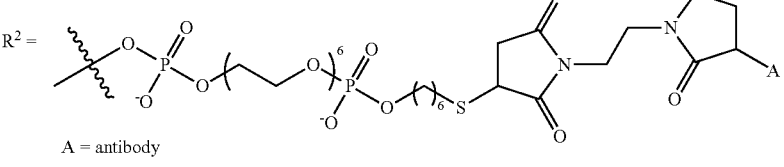 |

## TABLE 2-continued
Exemplary Compounds of Structure I
| No. | MW. Found Calc. | Structure |
|---|---|---|
| I-21 | TBD | 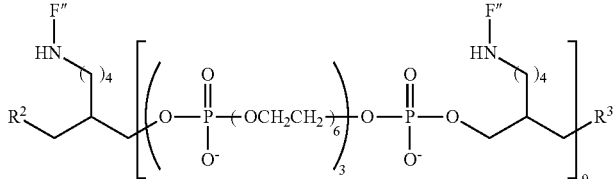 |
| I-22 | TBD | 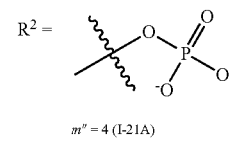 |

TABLE 2-continued

Exemplary Compounds of Structure I

| No. | MW. Found Calc. | Structure |
|---|---|---|
| I-23 | TBD | 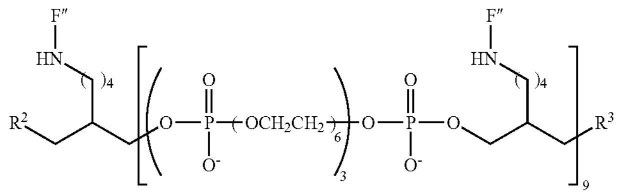 |
| I-24 | TBD | 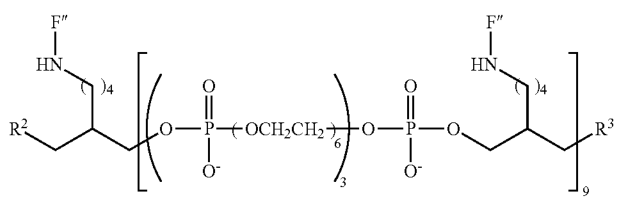 |

TABLE 2-continued
Exemplary Compounds of Structure I
| No. | MW. Found Calc. | Structure |
|---|---|---|
| I-25 | TBD | 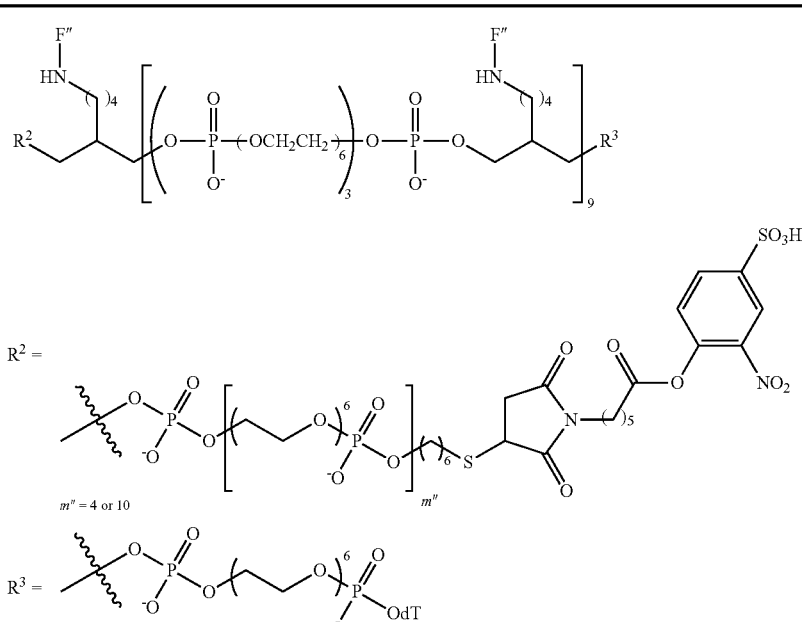 |
| I-26 | TBD | 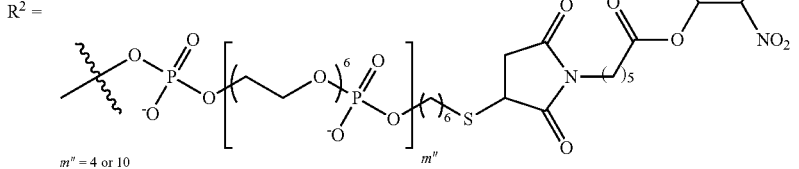 |

TABLE 2-continued
Exemplary Compounds of Structure I
| No. | MW. Found Calc. | Structure |
|---|---|---|
| I-27 | TBD | 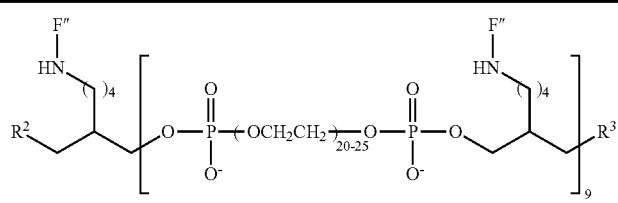 |
| I-28 | TBD | 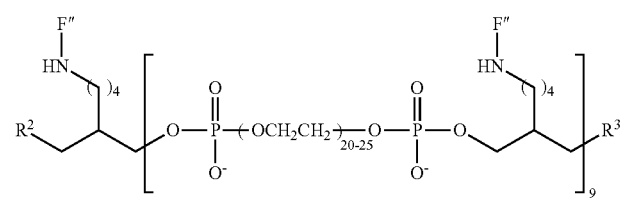 |

TABLE 2-continued
Exemplary Compounds of Structure I
| No. | MW. Found Calc. | Structure |
|---|---|---|
| I-29 | TBD | 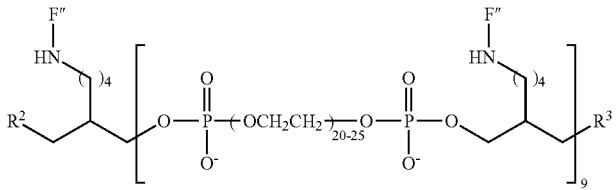 |
| I-30 | TBD | 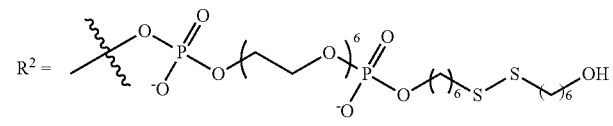 |

TABLE 2-continued
Exemplary Compounds of Structure I
| No. | MW. Found Calc. | Structure |
|---|---|---|
| I-31 | TBD | 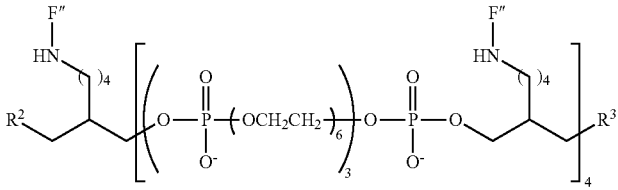 |
| I-32 | 7241.2 7238.2 | 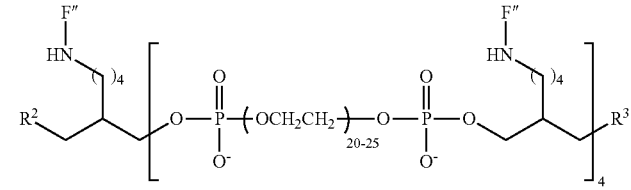 |

TABLE 2-continued
Exemplary Compounds of Structure I
| No. | MW. Found Calc. | Structure |
|---|---|---|
| I-33 | TBD | 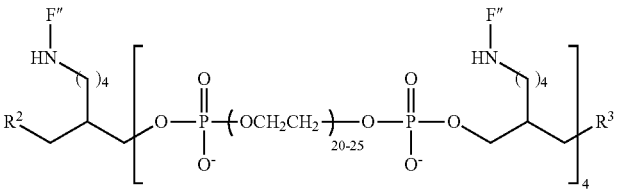 |
| I-34 | TBD | 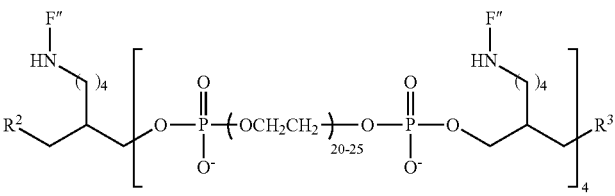 |

TABLE 2-continued

Exemplary Compounds of Structure I

| No. | MW. Found Calc. | Structure |
|---|---|---|
| I-35 | TBD | |
| I-36 | TBD | |

TABLE 2-continued

Exemplary Compounds of Structure I

| No. | MW. Found Calc. | Structure |
|---|---|---|
| I-37 | 6997.1<br>6997.0 | |
| I-38 | TBD | |

TABLE 2-continued

Exemplary Compounds of Structure I

| No. | MW. Found Calc. | Structure |
|---|---|---|
| I-39 | TBD | 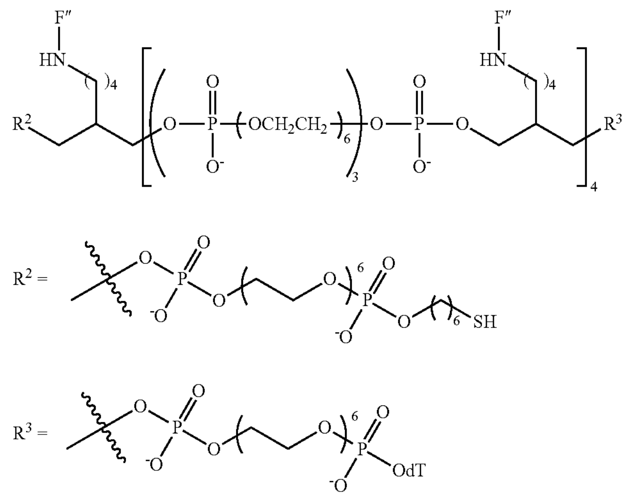 |
| I-40 | TBD | 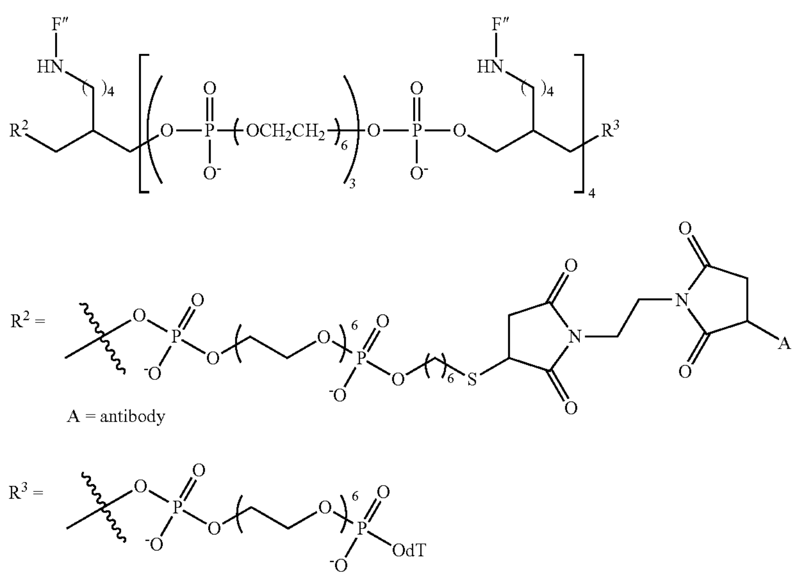 |

A = antibody

TABLE 2-continued
Exemplary Compounds of Structure I
| No. | MW. Found Calc. | Structure |
|---|---|---|
| I-41 | TBD | 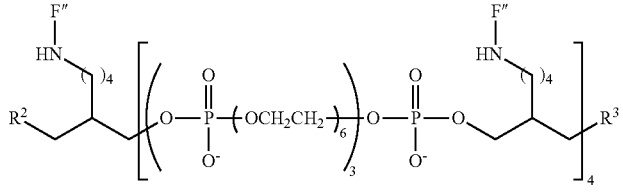 |
| I-42 | TBD | 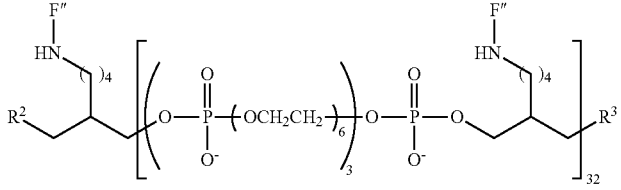 |
| I-43 | 3103.9<br>3103.6 | 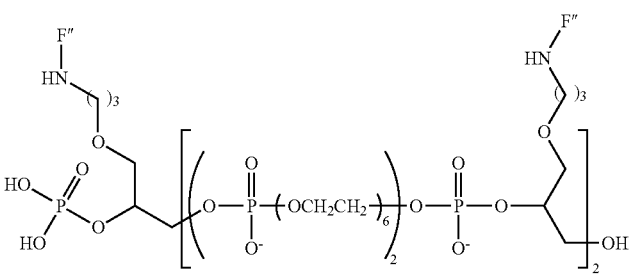 |

TABLE 2-continued

Exemplary Compounds of Structure I

| No. | MW. Found Calc. | Structure |
|---|---|---|
| I-44 | 5619.5 5619.8 | 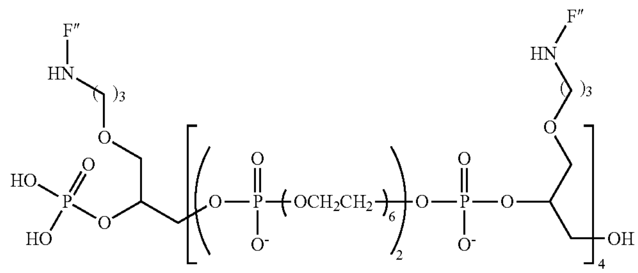 |
| I-45 | 15684.6 15681.5 | 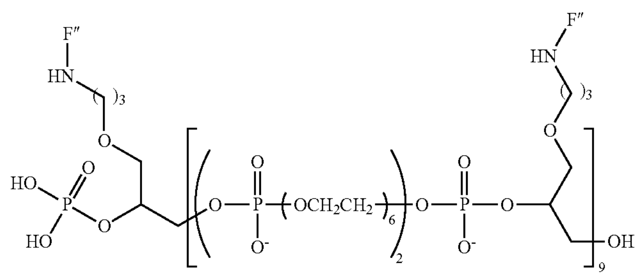 |
| I-46 | 6997.1 6997.0 | 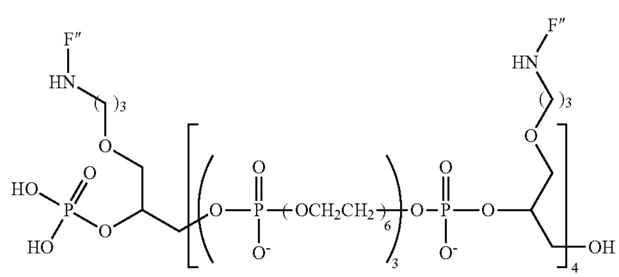 |
| I-47 | 11912.1 11910.1 | 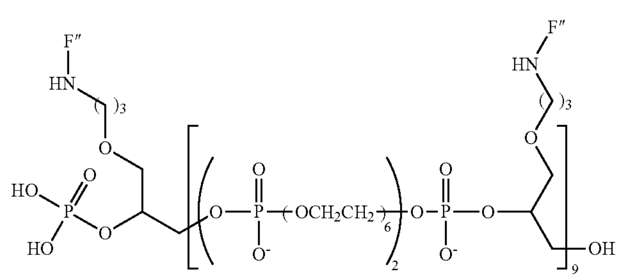 |

TABLE 2-continued

Exemplary Compounds of Structure I

| No. | MW. Found Calc. | Structure |
|---|---|---|
| I-48 | 9273.9 9272.0 | 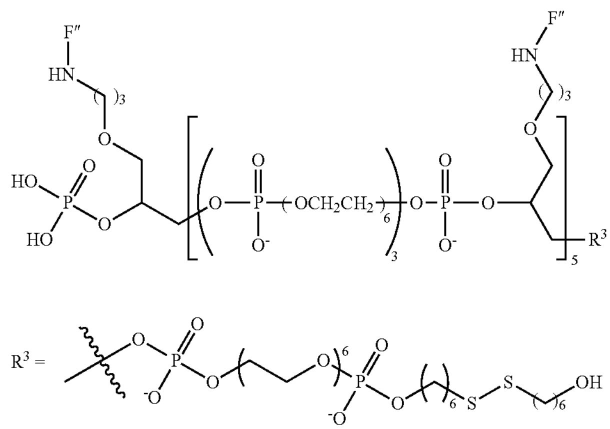 |
| I-49 | 16252.9 16250.0 | 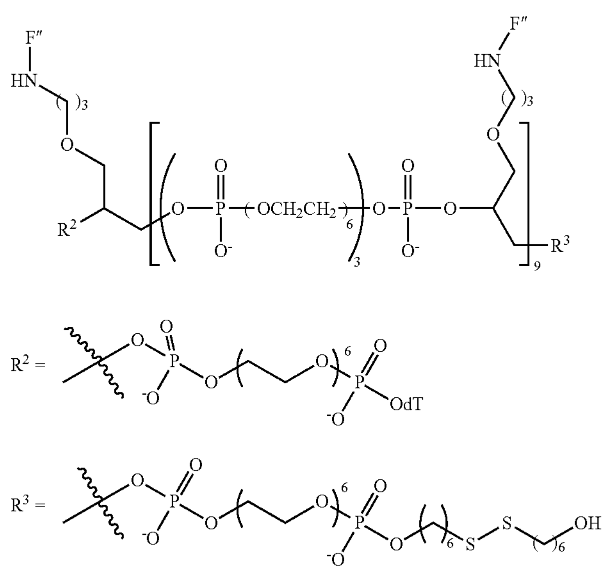 |

TABLE 2-continued

Exemplary Compounds of Structure I

| No. | MW. Found Calc. | Structure |
|---|---|---|
| I-50 | 17260.3 17260.0 | |
| I-51 | TBD | |
| I-52 | TBD | |

TABLE 2-continued
Exemplary Compounds of Structure I
| No. | MW. Found Calc. | Structure |
|---|---|---|
| I-53 | TBD | 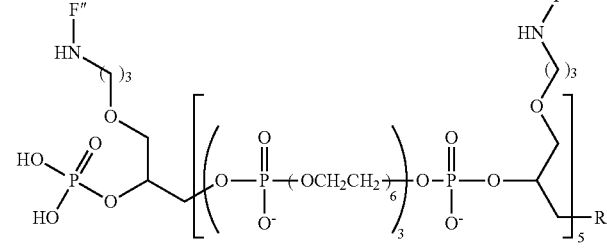 |
| I-54 | TBD | 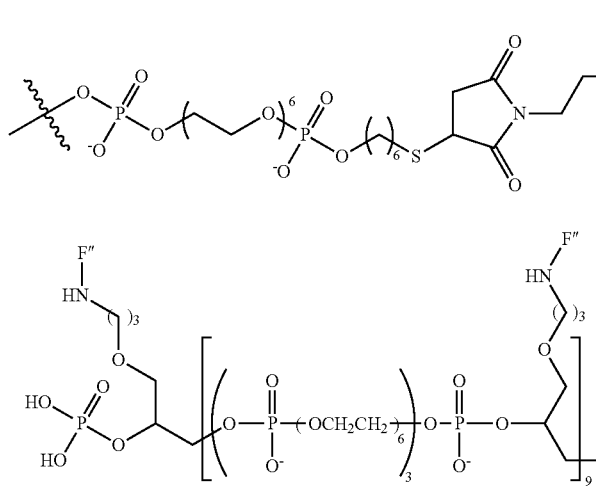 |
| I-55 | TBD | 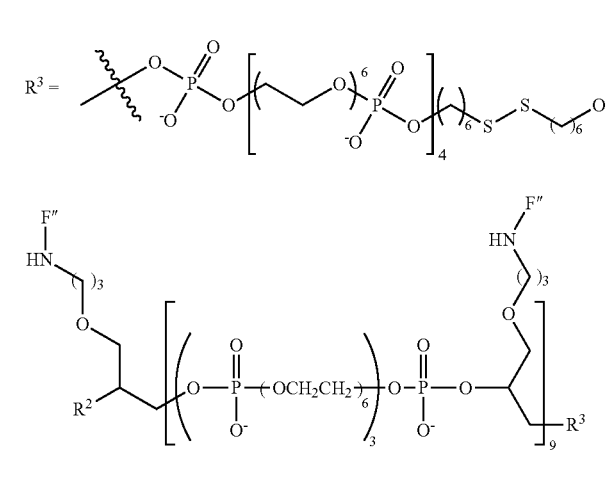 |

US 9,851,359 B2
TABLE 2-continued
Exemplary Compounds of Structure I
| No. | MW. Found Calc. | Structure |
|---|---|---|
| I-56 | TBD | 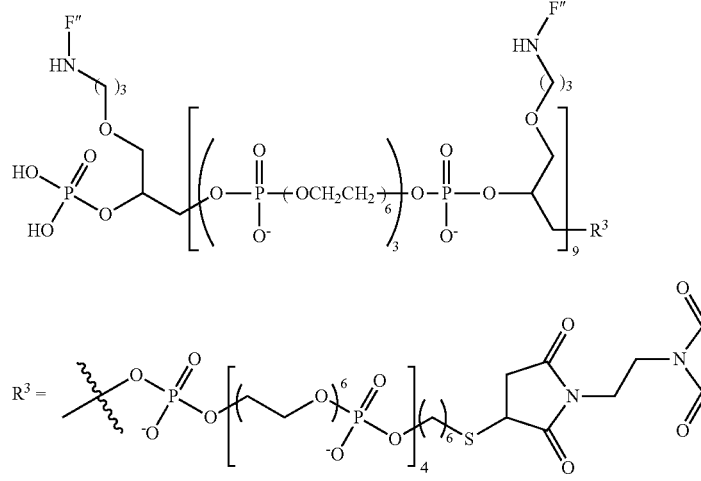 |
| I-57 | TBD | 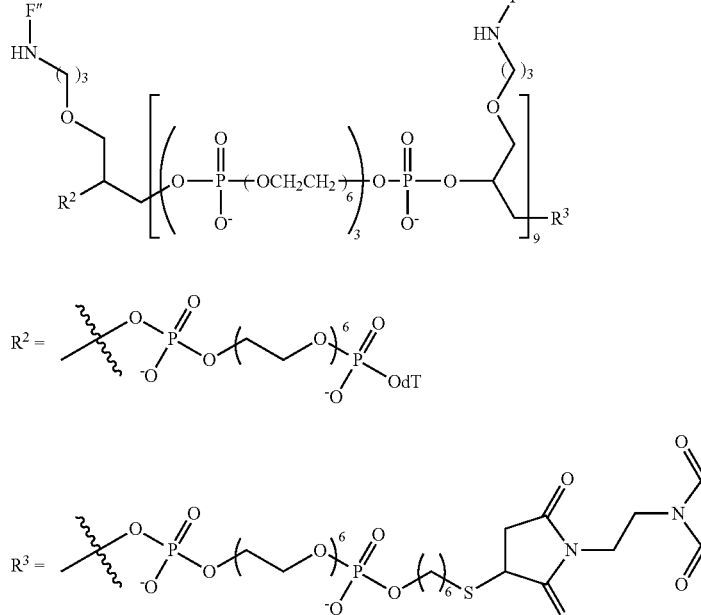 |

TABLE 2-continued
Exemplary Compounds of Structure I
| No. | MW. Found Calc. | Structure |
|---|---|---|
| I-58 | TBD | 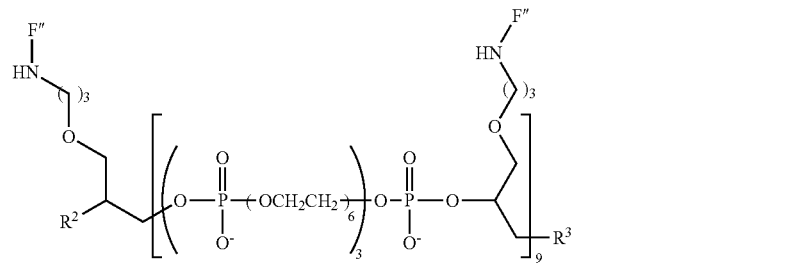 |
| I-59 | TBD | 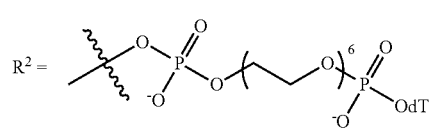 |
| I-60 | TBD | 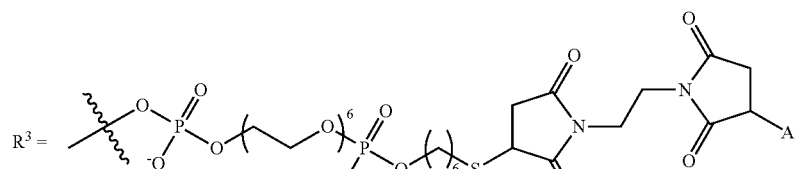<br>n = about 23 such that PEG M.W. = about 1,000 |
*TBD = to be determined As used in Table 2 and throughout the application $R^2$, $R^3$, m, n and L' have the definitions provided for compounds of structure (I) unless otherwise indicated, and F, F' and F" refer to a fluorescein moiety having the following structures, respectively:

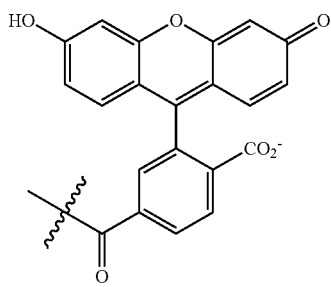

F

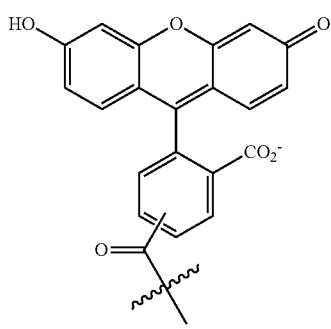

F'

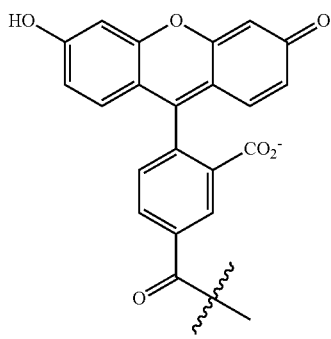

F"

"dT" refers to the following structure:

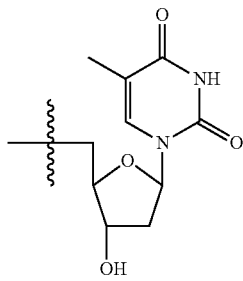

dT

Some embodiments include any of the foregoing compounds, including the specific compounds provided in Table 2, conjugated to a targeting moiety, such as an antibody.

The present disclosure generally provides compounds having increased fluorescence emission relative to earlier known compounds. Accordingly, certain embodiments are directed to a fluorescent compound comprising Y fluorescent moieties M, wherein the fluorescent compound has a peak fluorescence emission upon excitation with a predetermined wavelength of ultraviolet light of at least 85% of Y times greater than the peak fluorescence emission of a single M moiety upon excitation with the same wavelength of ultraviolet light, and wherein Y is an integer of 2 or more. Fluorescent compounds include compounds which emit a fluorescent signal upon excitation with light, such as ultraviolet light.

In some embodiments, the fluorescent compound has a peak fluorescence emission of at least 90% of Y times greater, 95% of Y times greater, 97% of Y times greater or 99% of Y times greater than the peak fluorescence emission of a single M moiety.

In some embodiments, Y is an integer from 2 to 100, for example 2-10.

In some embodiments, the Y M moiety have, independently, one of the following structures:

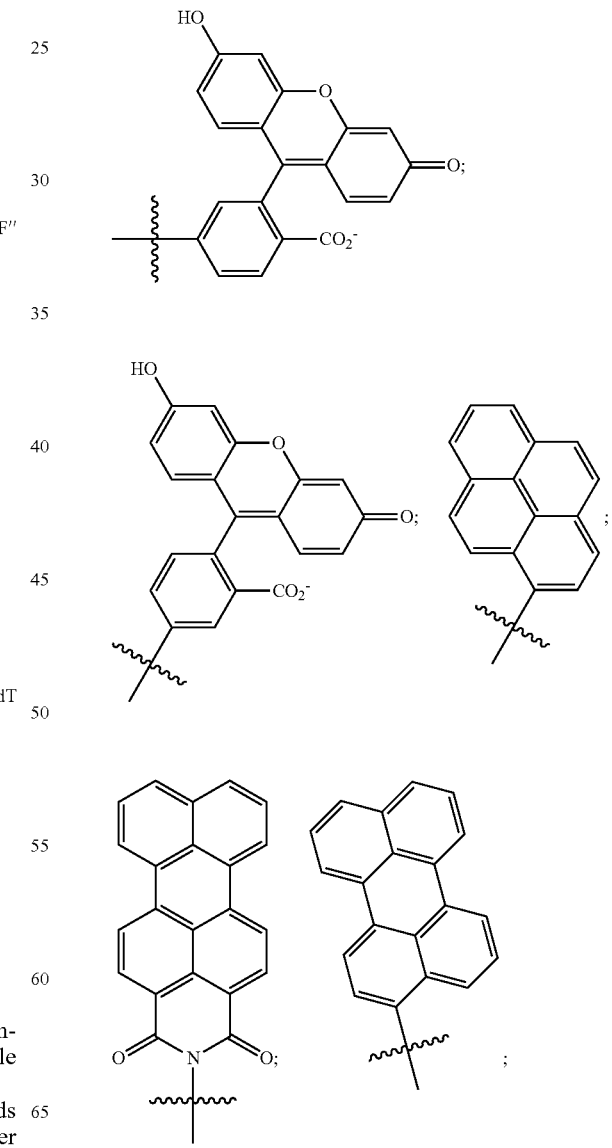

-continued
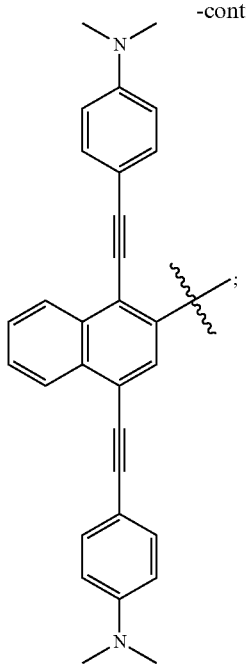
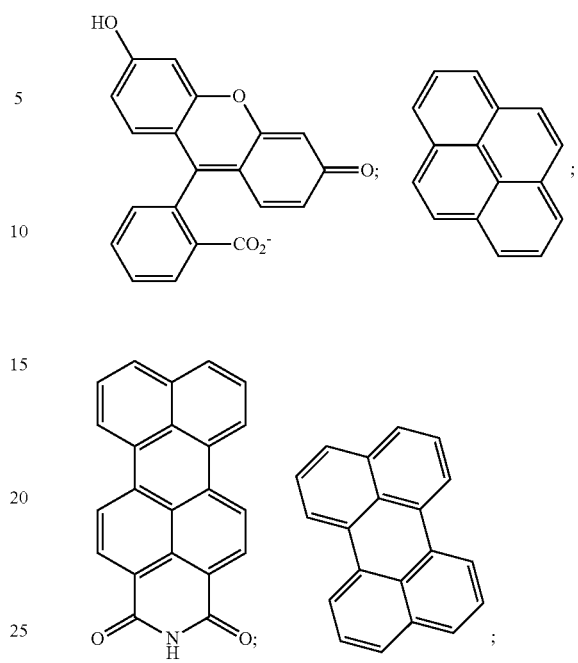
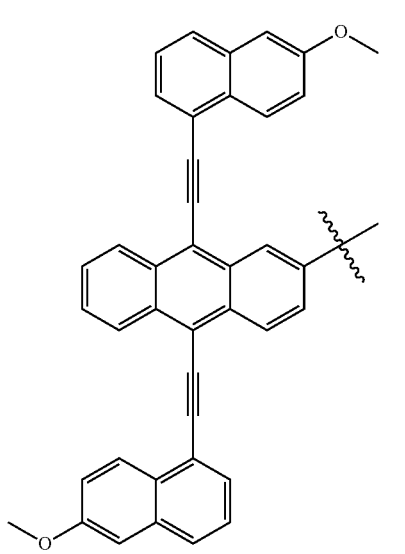
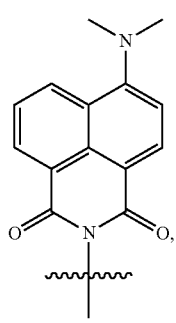
wherein ⌇ indicates a point of attachment to the fluorescent compound.
In other embodiments, the single M moiety has, independently, one of the following structures:
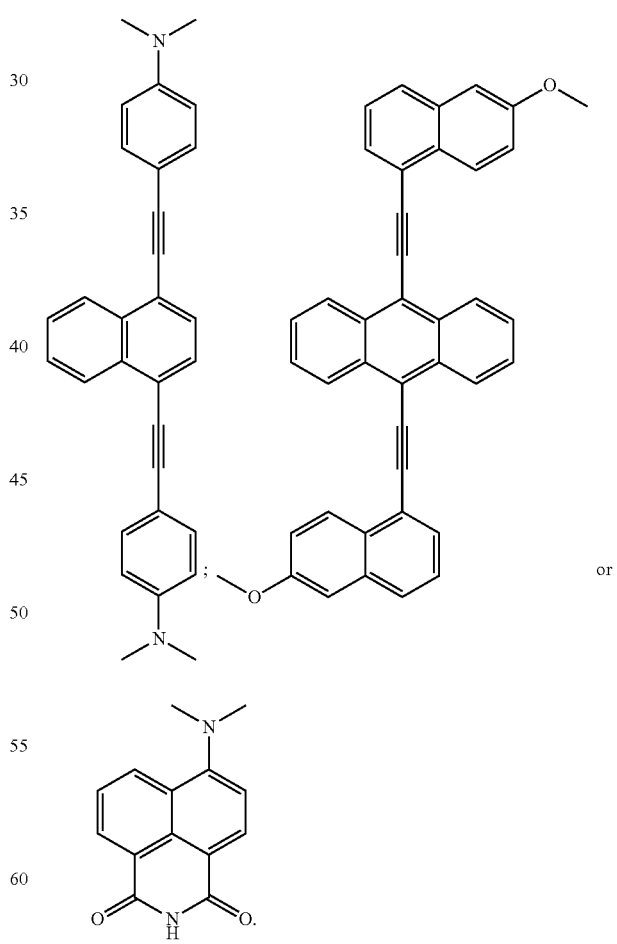
In more specific embodiments, the fluorescent compound comprises Y M moieties, independently having one of the following structures:

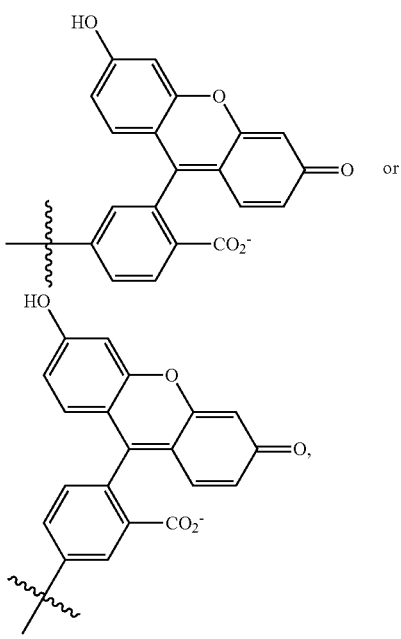

wherein ⌇⌇⌇ indicates a point of attachment to the fluorescent compound, and the single M moiety has the following structure:

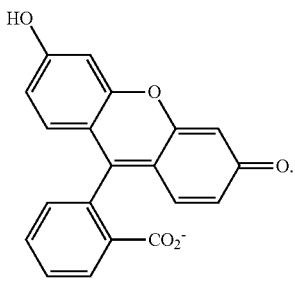

In other embodiments, the peak fluorescence emission is at a wavelength ranging from about 500 to about 550 nm.

In still more embodiments, the fluorescent compound comprises at least one ethylene oxide moiety.

Compositions comprising the fluorescent compound of any one of claims and an analyte are also provided.

The presently disclosed compounds are "tunable," meaning that by proper selection of the variables in any of the foregoing compounds, one of skill in the art can arrive at a compound having a desired and/or predetermined molar fluorescence (molar brightness). The tunability of the compounds allows the user to easily arrive at compounds having the desired fluorescence and/or color for use in a particular assay or for identifying a specific analyte of interest. Although all variables may have an effect on the molar fluorescence of the compounds, proper selection of M, $L^4$, m and n is believed to play an important role in the molar fluorescence of the compounds. Accordingly, in one embodiment is provided a method for obtaining a compound having a desired molar fluorescence, the method comprising selecting an M moiety having a known fluorescence, preparing a compound of structure (I) comprising the M moiety, and selecting the appropriate variables for $L^4$, m and n to arrive at the desired molar fluorescence.

Molar fluorescence in certain embodiments can be expressed in terms of the fold increase or decrease relative to the fluorescence emission of the parent fluorophore (e.g., monomer). In some embodiments the molar fluorescence of the present compounds is 1.1×, 1.5×, 2×, 3×, 4×, 5×, 6×, 7×, 8×, 9× 10× or even higher relative to the parent fluorophore. Various embodiments include preparing compounds having the desired fold increase in fluorescence relative to the parent fluorophore by proper selection of $L^4$, m and n.

For ease of illustration, various compounds comprising phosphorous moieties (e.g., phosphate and the like) are depicted in the anionic state (e.g., —OPO(OH)O⁻, —OPO$_3^{2-}$). One of skill in the art will readily understand that the charge is dependent on pH and the uncharged (e.g., protonated or salt, such as sodium or other cation) forms are also included in the scope of embodiments of the invention.

Compositions comprising any of the foregoing compounds and one or more analyte molecules (e.g., biomolecules) are provided in various other embodiments. In some embodiments, use of such compositions in analytical methods for detection of the one or more analyte molecules are also provided.

In still other embodiments, the compounds are useful in various analytical methods. For example, in certain embodiments the disclosure provides a method of staining a sample, the method comprising adding to said sample a compound of structure (I), for example wherein one of $R^2$ or $R^3$ is a linker comprising a covalent bond to an analyte molecule (e.g., biomolecule) or microparticle, and the other of $R^2$ or $R^3$ is H, OH, alkyl, alkoxy, alkylether or —OP(=$R_a$)($R_b$)$R_c$, in an amount sufficient to produce an optical response when said sample is illuminated at an appropriate wavelength.

In some embodiments of the foregoing methods, $R^2$ is a linker comprising a covalent linkage to an analyte molecule, such as a biomolecule. For example, a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In yet other embodiments of the foregoing method, $R^2$ is a linker comprising a covalent linkage to a solid support such as a microparticle. For example, in some embodiments the microparticle is a polymeric bead or nonpolymeric bead.

In even more embodiments, said optical response is a fluorescent response.

In other embodiments, said sample comprises cells, and some embodiments further comprise observing said cells by flow cytometry.

In still more embodiments, the method further comprises distinguishing the fluorescence response from that of a second fluorophore having detectably different optical properties.

In other embodiments, the disclosure provides a method for visually detecting an analyte molecule, such as a biomolecule, comprising:

(a) providing a compound of structure (I), for example, wherein one of $R^2$ or $R^3$ is a linker comprising a covalent bond to the analyte molecule, and the other of $R^2$ or $R^3$ is H, OH, alkyl, alkoxy, alkylether or —OP(=$R_a$)($R_b$)$R_c$; and (b) detecting the compound by its visible properties.

In some embodiments the analyte molecule is a nucleic acid, amino acid or a polymer thereof (e.g., polynucleotide or polypeptide). In still more embodiments, the analyte molecule is an enzyme, receptor, receptor ligand, antibody, glycoprotein, aptamer or prion.

In other embodiments, a method for visually detecting an analyte molecule, such as a biomolecule is provided, the method comprising:
(a) admixing any of the foregoing compounds with one or more analyte molecules; and
(b) detecting the compound by its visible properties.

In other embodiments is provided a method for visually detecting an analyte molecule, the method comprising:
(a) admixing the compound of claim 1, wherein $R^2$ or $R^3$ is Q or a linker comprising a covalent bond to Q, with the analyte molecule;
(b) forming a conjugate of the compound and the analyte molecule; and
(c) detecting the conjugate by its visible properties.

Other exemplary methods include a method for detecting an analyte, the method comprising:
(a) providing a compound of structure (I), wherein $R^2$ or $R^3$ comprises a linker comprising a covalent bond to a targeting moiety having specificity for the analyte;
(b) admixing the compound and the analyte, thereby associating the targeting moiety and the analyte; and
(c) detecting the compound, for example by its visible or fluorescent properties.

In certain embodiments of the foregoing method, the analyte is a particle, such as a cell, and the method includes use of flow cytometry. For example, the compound may be provided with a targeting moiety, such as an antibody, for selectively associating with the desired cell, thus rendering the cell detectable by any number of techniques, such as visible or fluorescence detection. Appropriate antibodies can be selected by one of ordinary skill in the art depending on the desired end use. Exemplary antibodies for use in certain embodiments include UCHT1 and MOPC-21.

Embodiments of the present compounds thus find utility in any number of methods, including, but not limited: cell counting; cell sorting; biomarker detection; quantifying apoptosis; determining cell viability; identifying cell surface antigens; determining total DNA and/or RNA content; identifying specific nucleic acid sequences (e.g., as a nucleic acid probe); and diagnosing diseases, such as blood cancers.

In addition to the above methods, embodiments of the compounds of structure (I) find utility in various disciplines and methods, including but not limited to: imaging in endoscopy procedures for identification of cancerous and other tissues; single-cell and/or single molecule analytical methods, for example detection of polynucleotides with little or no amplification; cancer imaging, for example by including a targeting moiety, such as an antibody or sugar or other moiety that preferentially binds cancer cells, in a compound of structure (I) to; imaging in surgical procedures; binding of histones for identification of various diseases; drug delivery, for example by replacing the M moiety in a compound of structure (I) with an active drug moiety; and/or contrast agents in dental work and other procedures, for example by preferential binding of the compound of structure (I) to various flora and/or organisms.

It is understood that any embodiment of the compounds of structure (I), as set forth above, and any specific choice set forth herein for a $R^1$, $R^2$, $R^3$, $R^4$, $R^5$, L', $L^1$, $L^2$, $L^3$, $L^4$, M, m and/or n variable in the compounds of structure (I), as set forth above, may be independently combined with other embodiments and/or variables of the compounds of structure (I) to form embodiments of the invention not specifically set forth above. In addition, in the event that a list of choices is listed for any particular $R^1$, $R^2$, $R^3$, $R^4$, $R^5$, L', $L^1$, $L^2$, $L^3$, $L^4$, M, m and/or n variable in a particular embodiment and/or claim, it is understood that each individual choice may be deleted from the particular embodiment and/or claim and that the remaining list of choices will be considered to be within the scope of the invention.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Furthermore, all compounds of the invention which exist in free base or acid form can be converted to their salts by treatment with the appropriate inorganic or organic base or acid by methods known to one skilled in the art. Salts of the compounds of the invention can be converted to their free base or acid form by standard techniques.

The following Reaction Schemes illustrate exemplary methods of making compounds of this invention. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

Reaction Scheme I

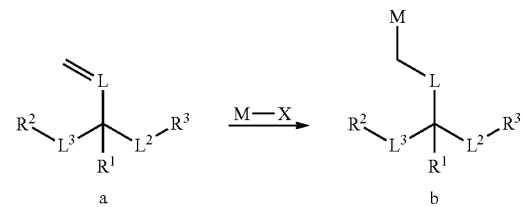

Reaction Scheme I illustrates an exemplary method for preparing an intermediate useful for preparation of compounds of structure (I), where $R^1$, $L^2$, $L^3$ and M are as defined above, $R^2$ and $R^3$ are as defined above or are protected variants thereof and L is an optional linker. Referring to Reaction Scheme 1, compounds of structure a can be purchased or prepared by methods well-known to those of ordinary skill in the art. Reaction of a with M-X, where x is a halogen such as bromo, under Suzuki coupling conditions known in the art results in compounds of structure b. Compounds of structure b can be used for preparation of compounds of structure (I) as described below.

Reaction Scheme II

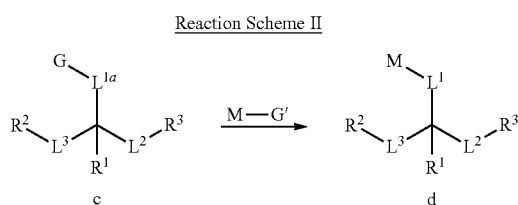

Reaction Scheme II illustrates an alternative method for preparation of intermediates useful for preparation of compounds of structure (I). Referring to reaction Scheme II, where $R^1$, $L^1$, $L^2$, $L^3$, G and M are as defined above, and $R^2$ and $R^3$ are as defined above, or are protected variants thereof, a compound of structure c, which can be purchased or prepared by well-known techniques, is reacted with M-G' to yield compounds of structure d. Here, G and G' represent functional groups having complementary reactivity (i.e., functional groups which react to form a covalent bond). G' may be pendant to M or a part of the structural backbone of M. G and G' may be any number of functional groups described herein, such as alkyne and azide, respectively, amine and activated ester, respectively or amine and isothiocyanate, respectively, and the like.

The compound of structure (I) may be prepared from one of structures b or d by reaction under well-known automated DNA synthesis conditions with a phosphoramidite compound having the following structure (e):

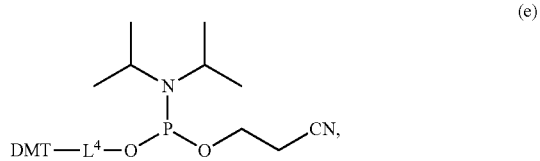

wherein A is as defined herein and each L is independently an optional linker.

DNA synthesis methods are well-known in the art. Briefly, two alcohol groups, for example $R^2$ and $R^3$ in intermediates b or d above, are functionalized with a dimethoxytrityl (DMT) group and a 2-cyanoethyl-N,N-diisopropylamino phosphoramidite group, respectively. The phosphoramidite group is coupled to an alcohol group, typically in the presence of an activator such as tetrazole, followed by oxidation of the phosphorous atom with iodine. The dimethoxytrityl group can be removed with acid (e.g., chloroacetic acid) to expose the free alcohol, which can be reacted with a phosphoramidite group. The 2-cyanoethyl group can be removed after oligomerization by treatment with aqueous ammonia.

Preparation of the phosphoramidites used in the oligomerization methods is also well-known in the art. For example, a primary alcohol (e.g., $R^3$) can be protected as a DMT group by reaction with DMT-Cl. A secondary alcohol (e.g., $R^2$) is then functionalized as a phosphoramidite by reaction with an appropriate reagent such as 2-cyanoethyl N,N-dissopropylchlorophosphoramidite. Methods for preparation of phosphoramidites and their oligomerization are well-known in the art and described in more detail in the examples.

Compounds of structure (I) are prepared by oligomerization of intermediates b or d and e according to the well-known phosphoramidite chemistry described above. The desired number of m and n repeating units is incorporated into the molecule by repeating the phosphoramidite coupling the desired number of times. It will be appreciated that compounds of structure (II) as, described below, can be prepared by analogous methods.

In various other embodiments, compounds useful for preparation of the compound of structure (I) are provided. The compounds can be prepared as described above in monomer, dimer and/or oligomeric form and then the M moiety covalently attached to the compound via any number of synthetic methodologies (e.g., the "click" reactions described above) to form a compound of structure (I). Accordingly, in various embodiments a compound is provided having the following structure (II):

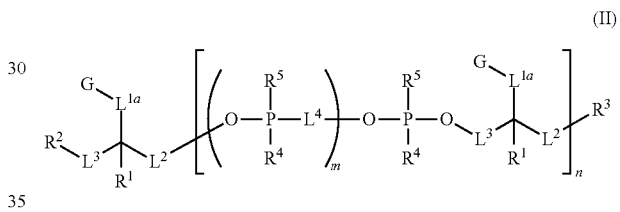

(II)

or a stereoisomer, salt or tautomer thereof, wherein:

G is, at each occurrence, independently a moiety comprising a reactive group, or protected analogue thereof, capable of forming a covalent bond with a complementary reactive group;

$L^{1a}$ $L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently a heteroalkylene, heteroalkenylene or heteroalkynylene linker of greater than three atoms in length, wherein the heteroatoms in the heteroalkylene, heteroalkenylene and heteroalkynylene linker are selected from O, N and S;

$R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q or L';

$R^4$ is, at each occurrence, independently OH, SH, O⁻, S⁻, O$R_d$ or S$R_d$;

$R^5$ is, at each occurrence, independently oxo, thioxo or absent;

$R_a$ is O or S;

$R_b$ is OH, SH, O⁻, S⁻, O$R_d$ or S$R_d$;

$R_c$ is OH, SH, O⁻, S⁻, O$R_d$, OL', S$R_d$, alkyl, alkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected analogue thereof, capable of forming a covalent bond with an analyte molecule, targeting moiety, a solid support or a complementary reactive group Q;

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (II);

m is, at each occurrence, independently an integer of zero or greater, provided that at least one occurrence of m is an integer of one or greater; and n is an integer of one or greater.

In other embodiments of structure (II):

G is, at each occurrence, independently a moiety comprising a reactive group capable of forming a covalent bond with a complementary reactive group;

$L^{1a}$, $L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently a heteroalkylene, heteroalkenylene or heteroalkynylene linker of greater than three atoms in length, wherein the heteroatoms in the heteroalkylene, heteroalkenylene and heteroalkynylene linker are selected from O, N and S;

$R^1$ is, at each occurrence, independently H, alkyl or alkoxy;

$R^2$ and $R^3$ are each independently H, OH, SH, alkyl, alkoxy, alkylether, —OP($=R_a$)($R_b$)$R_c$, Q, a linker comprising a covalent bond to Q, a linker comprising a covalent bond to an analyte molecule, a linker comprising a covalent bond to a solid support or a linker comprising a covalent bond to a further compound of structure (II), wherein: $R_a$ is O or S; $R_b$ is OH, SH, O$^-$, S$^-$, OR$_d$ or SR$_d$; $R_c$ is OH, SH, O$^-$, S$^-$, OR$_d$, SR$_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;

$R^4$ is, at each occurrence, independently OH, SH, O$^-$, S$^-$, OR$_d$ or SR$_d$;

$R^5$ is, at each occurrence, independently oxo, thioxo or absent;

Q is, at each occurrence, independently a moiety comprising a reactive group capable of forming a covalent bond with an analyte molecule, a solid support or a complementary reactive group Q;

m is, at each occurrence, independently an integer of zero or greater, provided that at least one occurrence of m is an integer of one or greater; and n is an integer of one or greater.

The G moiety in the compound of structure (II) can be selected from any moiety comprising a group having the appropriate reactivity group for forming a covalent bond with a complementary group on an M moiety. In exemplary embodiments, the G moiety can be selected from any of the Q moieties described herein, including those specific examples provided in Table 1. In some embodiments, G comprises, at each occurrence, independently a moiety suitable for reactions including: the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse-demand Diels-Alder, alkene and tetrazole photoreaction and various displacement reactions, such as displacement of a leaving group by nucleophilic attack on an electrophilic atom.

In some embodiments, G is, at each occurrence, independently a moiety comprising an aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin or thiirane functional group.

In other embodiments, G comprises, at each occurrence, independently an alkyne or an azide group. In other embodiments, G comprises, at each occurrence, independently an amino, isothiocyanate or activated ester group. In different embodiments, G comprises, at each occurrence, independently a reactive group capable of forming a functional group comprising an alkene, ester, amide, thioester, disulfide, carbocyclic, heterocyclic or heteroaryl group, upon reaction with the complementary reactive group. For example, in some embodiment the heteroaryl is triazolyl.

In various other embodiments of the compound of structure (II), $L^2$ and $L^3$ are, at each occurrence, independently $C_1$-$C_6$ alkylene, $C_2$-$C_6$ alkenylene or $C_2$-$C_6$ alkynylene.

In other embodiments, the compound has the following structure (IIA):

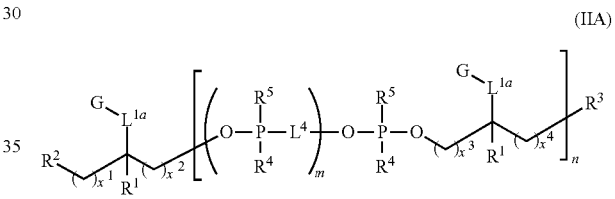

(IIA)

wherein:

$x^1$, $x^2$, $x^3$ and $x^4$ are, at each occurrence, independently an integer from 0 to 6.

In other embodiments of structure (II), each $L^{1a}$ is absent. In other embodiments, each $L^{1a}$ is present, for example $L^{1a}$ is, at each occurrence, independently heteroalkylene. In certain embodiments, $L^{1a}$ has the following structure:

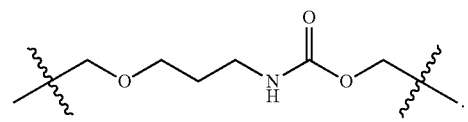 [SMILES: *COCCCNC(=O)OC*]

In other of any of the foregoing embodiments of compound (II), G is, at each occurrence, independently

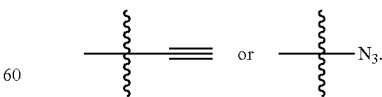

In various embodiments of the compound of structure (IIA), at least one occurrence of $x^1$, $x^2$, $x^3$ or $x^4$ is 1. In other embodiments, $x^1$, $x^2$, $x^3$ and $x^4$ are each 1 at each occurrence. In other embodiments, $x^1$ and $x^3$ are each 0 at each occurrence. In some embodiments, $x^2$ and $x^4$ are each 1 at each occurrence. In still other embodiments, $x^1$ and $x^3$ are each 0 at each occurrence, and $x^2$ and $x^4$ are each 1 at each occurrence.

In some other embodiments of the compound of structure (II) or (IIA), $L^4$ is at each occurrence, independently a heteroalkylene linker. In other more specific embodiments, $L^4$ is at each occurrence, independently an alkylene oxide linker. For example, in some embodiments $L^4$ is polyethylene oxide, and the compound has the following structure (IB):

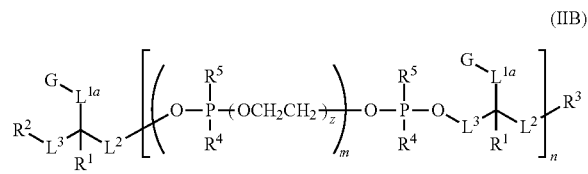
(IIB)

wherein z is an integer from 2 to 100, for example an integer from 3 to 6.

In other embodiments, $R^4$ is, at each occurrence, independently OH, O⁻ or $OR_d$, and in different embodiments $R^5$ is, at each occurrence, oxo.

In some different embodiments of any of the foregoing compounds of structure (II) or (IIa), $R^1$ is H.

In other various embodiments of the compounds of structure (II), $R^2$ and $R^3$ are each independently OH or $-OP(=R_a)(R_b)R_c$. In some different embodiments, $R^2$ or $R^3$ is OH or $-OP(=R_a)(R_b)R_c$, and the other of $R^2$ or $R^3$ is Q or a linker comprising a covalent bond to Q.

In still more different embodiments of any of the foregoing compounds of structure (II), $R^2$ and $R^3$ are each independently $-OP(=R_a)(R_b)R_c$. In some of these embodiments, $R_c$ is OL'.

In other embodiments of structure (II), $R^2$ and $R^3$ are each independently $-OP(=R_a)(R_b)OL'$, and L' is a heteroalkylene linker to: Q, a targeting moiety, an analyte (e.g., analyte molecule), a solid support, a solid support residue, a nucleoside or a further compound of structure (II).

The linker L' can be any linker suitable for attaching Q, a targeting moiety, an analyte (e.g., analyte molecule), a solid support, a solid support residue, a nucleoside or a further compound of structure (II) to the compound of structure (II). Advantageously certain embodiments include use of L' moieties selected to increase or optimize water solubility of the compound. In some certain embodiments, L' comprises an alkylene oxide or phosphodiester moiety, or combinations thereof.

In certain embodiments. L' has the following structure:

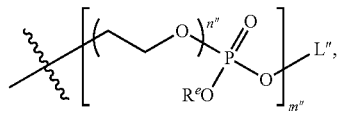

wherein:
m" and n" are independently an integer from 1 to 10;
$R^e$ is H, an electron pair or a counter ion;
L" is $R^e$ or a direct bond or linkage to: Q, a targeting moiety, an analyte (e.g., analyte molecule), a solid support, a solid support residue, a nucleoside or a further compound of structure (II).

In certain of the foregoing embodiments, the targeting moiety is an antibody or cell surface receptor antagonist.

In other more specific embodiments f any of the foregoing compounds of structure (II), $R^2$ or $R^3$ has one of the following structures:

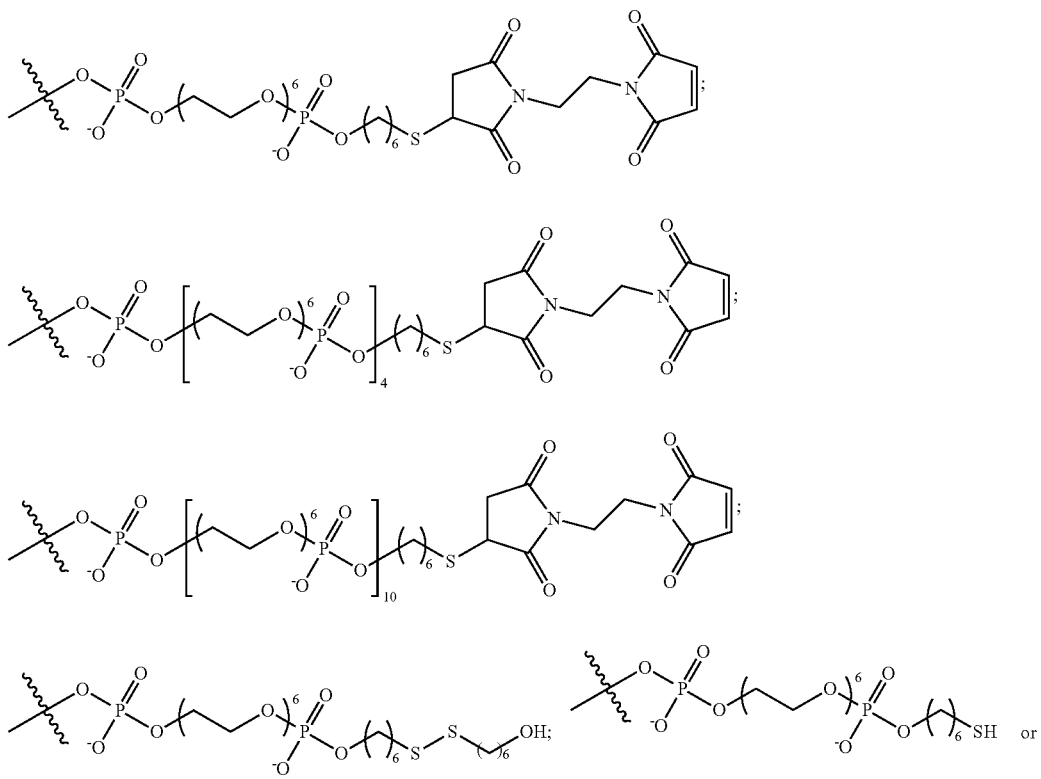

-continued

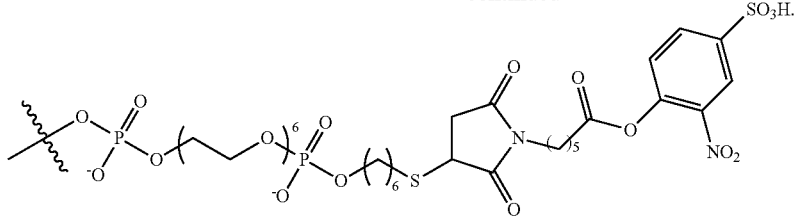

Certain embodiments of compounds of structure (II) can be prepared according to solid-phase synthetic methods analogous to those known in the art for preparation of oligonucleotides. Accordingly, in some embodiments, L' is a linkage to a solid support, a solid support residue or a nucleoside. Solid supports comprising an activated deoxythymidine (dT) group are readily available, and in some embodiments can be employed as starting material for preparation of compounds of structure (II). Accordingly, in some embodiments $R^2$ or $R^3$ has the following structure:

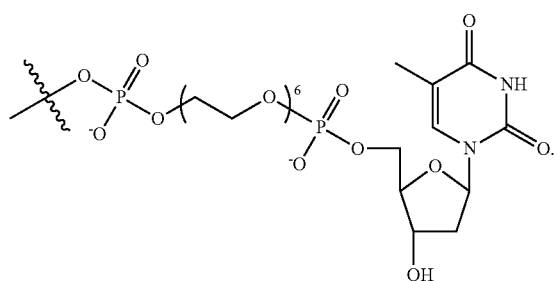

In still other embodiments of compounds of structure (II), Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'. For example, in some embodiments, Q' is present on a further compound of structure (II) (e.g., in the $R^2$ or $R^3$ position), and Q and Q' comprise complementary reactive groups such that reaction of the compound of structure (II) and the further compound of structure (II) results in covalently bound dimer of the compound of structure (II). Multimer compounds of structure (II) can also be prepared in an analogous manner and are included within the scope of embodiments of the invention.

The type of Q group and connectivity of the Q group to the remainder of the compound of structure (II) is not limited, provided that Q comprises a moiety having appropriate reactivity for forming the desired bond.

In certain embodiments of compounds of structure (II), the Q is a moiety which is not susceptible to hydrolysis under aqueous conditions, but is sufficiently reactive to form a bond with a corresponding group on an analyte molecule or solid support (e.g., an amine, azide or alkyne).

Certain embodiments of compounds of structure (II) comprises Q groups commonly employed in the field of bioconjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group. In some embodiments, the activated ester is an N-succinimide ester, imidoester or polyflourophenyl ester. In other embodiments, the alkyne is an alkyl azide or acyl azide.

Exemplary Q moieties for compounds of structure (II) are provided in Table I above.

As with compounds of structure (I), in some embodiments of compounds of structure (II), wherein Q is SH, the SH moiety will tend to form disulfide bonds with another sulfhydryl group on another compound of structure (II). Accordingly, some embodiments include compounds of structure (II), which are in the form of disulfide dimers, the disulfide bond being derived from SH Q groups.

In some other embodiments of compounds of structure (II), one of $R^2$ or $R^3$ is OH or —OP(=$R_a$)($R_b$)$R_c$, and the other of $R^2$ or $R^3$ is a linker comprising a covalent bond to an analyte molecule, a linker comprising a covalent bond to a targeting moiety or a linker comprising a covalent bond to a solid support. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In some embodiments, the targeting moiety is an antibody or cell surface receptor antagonist. In still different embodiments, the solid support is a polymeric bead or nonpolymeric bead.

In other embodiments of compounds of structure (II), m is, at each occurrence, independently an integer from 1 to 10. For example, in some embodiments m is, at each occurrence, independently an integer from 1 to 5, such as 1, 2, 3, 4 or 5. In some embodiments, m is 1. In some embodiments, m is 2. In some embodiments, m is 3. In some embodiments, m is 4. In some embodiments, m is 5.

In yet different embodiments of compounds of structure (II), n is an integer from 1 to 100. For example, in some embodiments n is an integer from 1 to 10. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In other different embodiments, the compound of structure (II) is selected from Table 3.

TABLE 3

Exemplary Compounds of Structure (II)

| No. | Structure |
|---|---|
| I-1 | 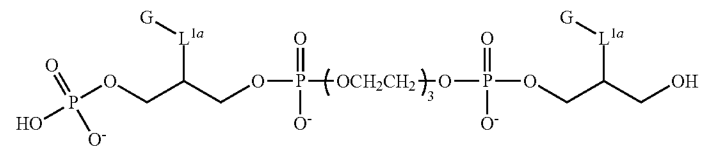 |
| II-2 | 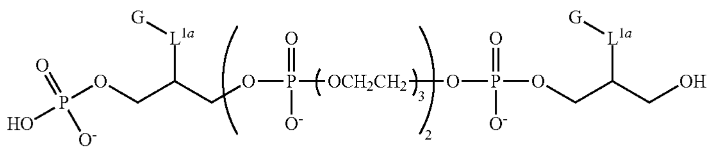 |
| II-3 | 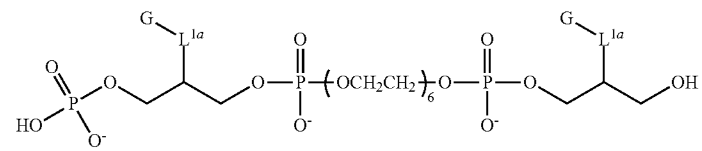 |
| II-4 | 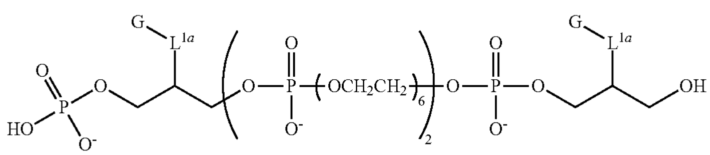 |
| II-5 | 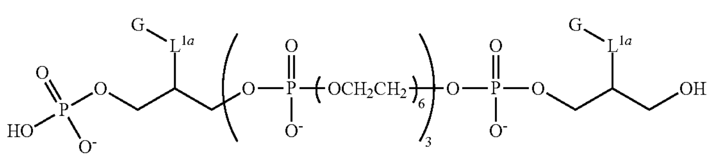 |
| II-6 | 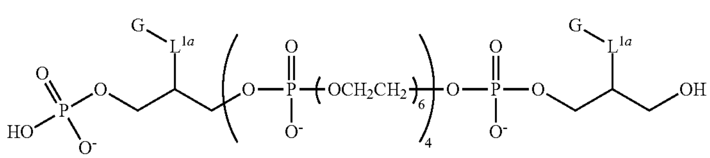 |
| II-7 | 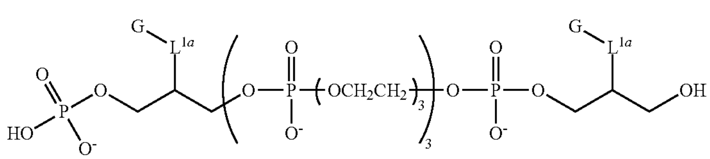 |
| II-8 | 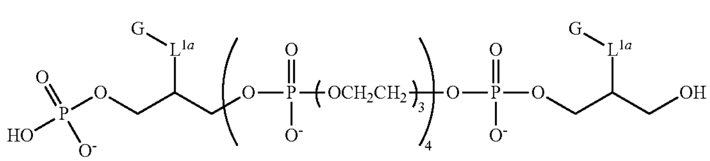 |
| II-9 | 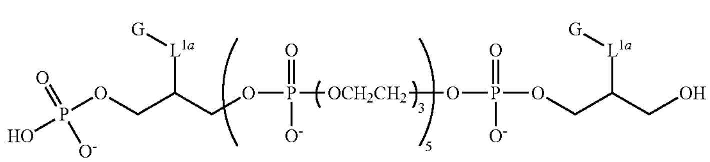 |

TABLE 3-continued

Exemplary Compounds of Structure (II)

| No. | Structure |
|---|---|
| II-10 | 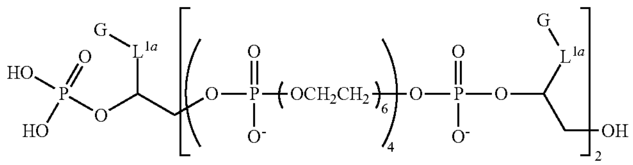 |
| II-11 | 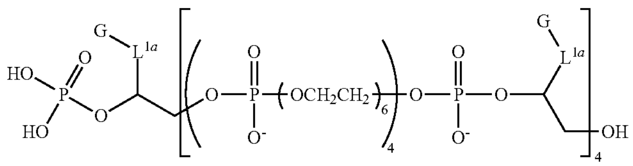 |
| II-12 | z = 3, 4, 5 or 6; m = 2, 3, 4 or 5; n = 1-10 |
| II-13 | 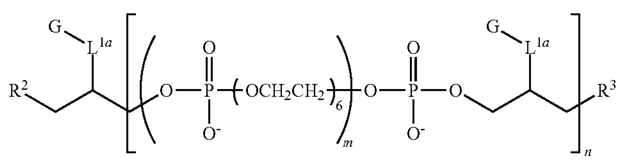 |
| II-14 | 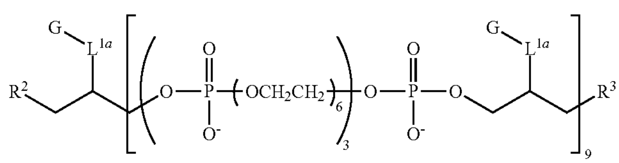 |
| II-15 | 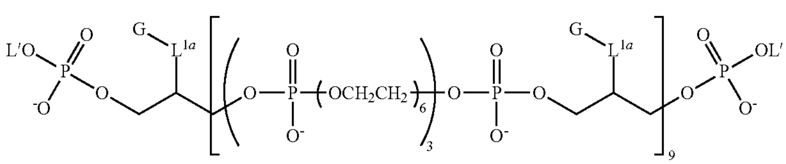 |
| II-16 | |

TABLE 3-continued
Exemplary Compounds of Structure (II)
| No. | Structure |
|---|---|
| II-17 | 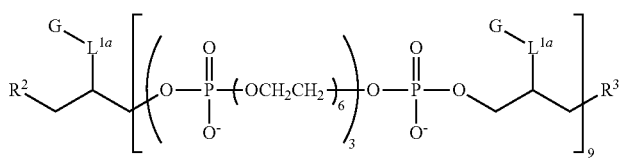<br>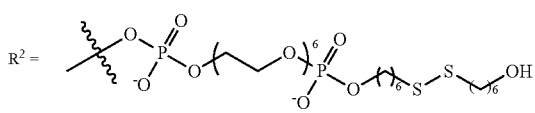<br>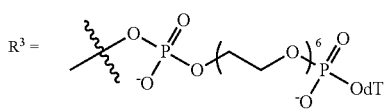 |
| II-18 | 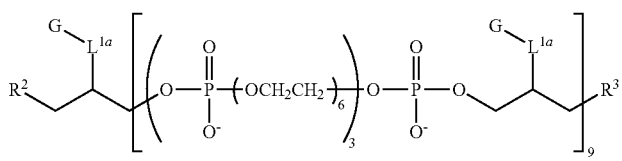<br>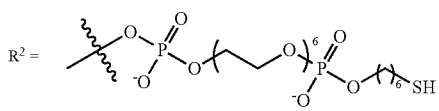<br>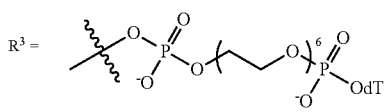 |
| II-19 | 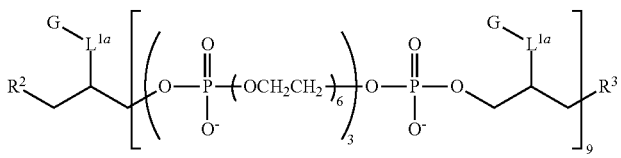<br>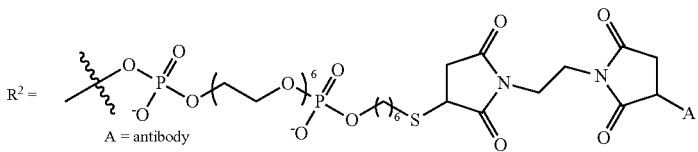<br>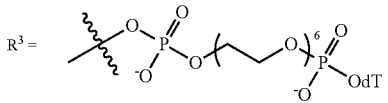 |

TABLE 3-continued
Exemplary Compounds of Structure (II)
| No. | Structure |
|---|---|
| II-20 | 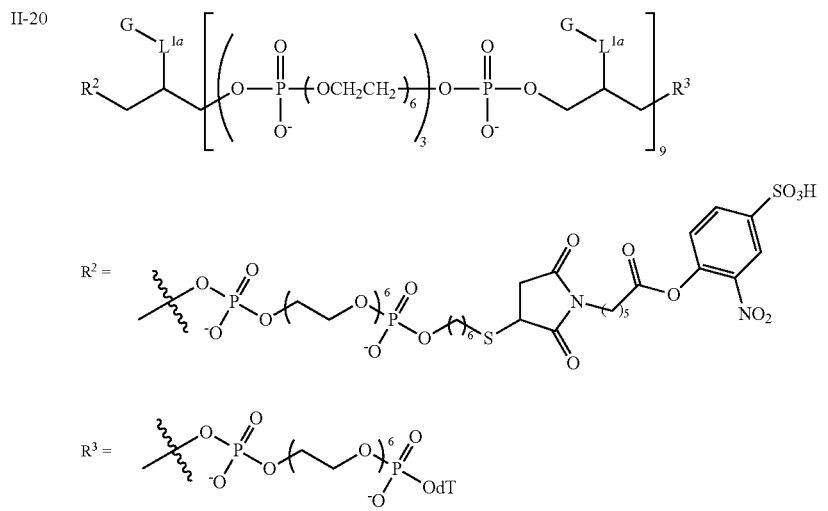 |
| II-21 | 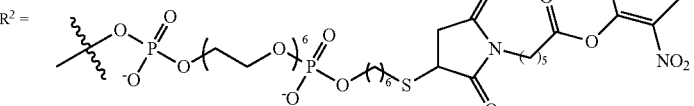 |
| II-22 | 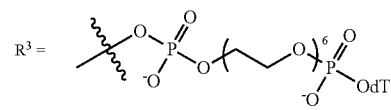 |

TABLE 3-continued
Exemplary Compounds of Structure (II)
| No. | Structure |
|---|---|
| II-23 | 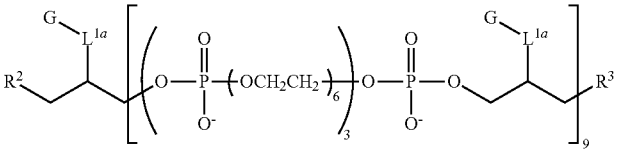 |
| II-24 | 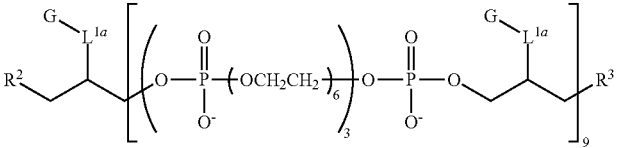 |
| II-25 | 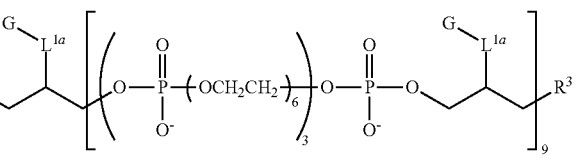 |

TABLE 3-continued
Exemplary Compounds of Structure (II)
| No. | Structure |
|---|---|
| II-26 | 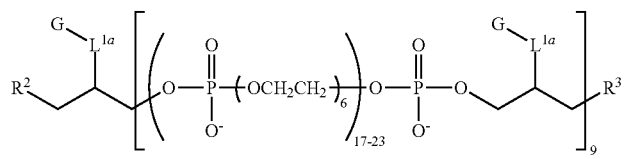 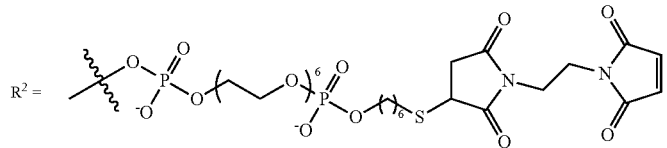 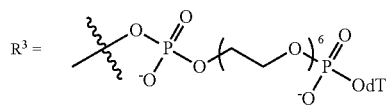 |
| II-27 | 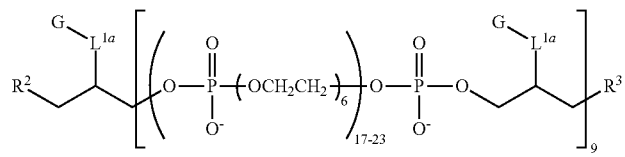 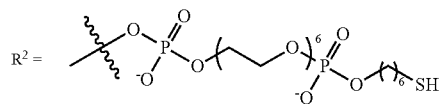 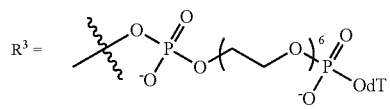 |
| II-28 | 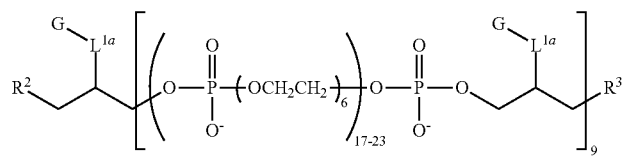 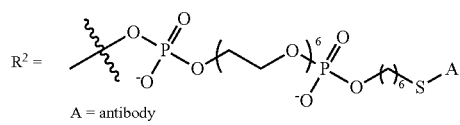 A = antibody 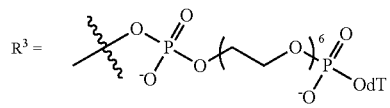 |

TABLE 3-continued

Exemplary Compounds of Structure (II)

| No. | Structure |
|---|---|
| II-29 | 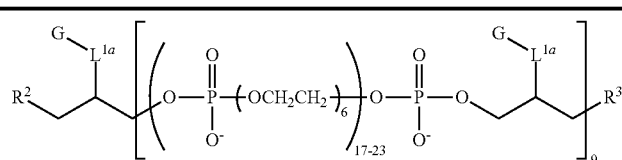 |
| II-30 | 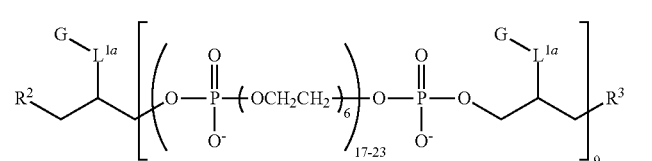 |

In various embodiments, G in the compounds of Table 3 is alkynyl, such as ethynyl. In other embodiments, G in the compounds of Table 3 is an azide. In other embodiments, G in the compounds of Table 3 is amino ($NH_2$). In other embodiments, G in the compounds of Table 3 is an isothiocyanate. In other embodiments, G in the compounds of Table 3 is an activated ester, such as an ester of N-hydroxysuccinimide.

The compounds of structure (II) can be used in various methods, for example in embodiments is provided a method for labeling an analyte, such as an analyte molecule, or targeting moiety, the method comprising:
 (a) admixing any of the described compounds of structure (II), wherein $R^2$ or $R^3$ is Q or a linker comprising a covalent bond to Q, with the analyte molecule;
 (b) forming a conjugate of the compound and the analyte or targeting moiety; and
 (c) reacting the conjugate with a compound of formula M-$L^{1b}$-G', thereby forming at least one covalent bond by reaction of at least one G and at least one G',
wherein:
 M is a moiety comprising two or more carbon-carbon double bonds and at least one degree of conjugation;
 $L^{1b}$ is an optional alkylene, heteroalkylene or heteroatomic linker; and
 G' is a reactive group complementary to G.

A different embodiment is a method for labeling an analyte, such as an analyte molecule or targeting moiety, the method comprising:
 (a) admixing any of the compounds of structure (II) disclosed herein, wherein $R^2$ or $R^3$ is Q or a linker comprising a covalent bond to Q, with a compound of formula M-$L^{1b}$-G', thereby forming at least one covalent bond by reaction of G and G'; and
 (b) reacting the product of step (A) with the analyte or targeting moiety, thereby forming a conjugate of the product of step (A) and the analyte molecule,
wherein:
 M is a moiety comprising two or more carbon-carbon double bonds and at least one degree of conjugation;
 $L^{1b}$ is an optional alkylene, heteroalkylene or heteroatomic linker; and
 G' is a reactive group complementary to G.

Further, as noted above, the compounds of structure (II) are useful for preparation of compounds of structure (I).

Accordingly, in one embodiment is provided a method for preparing a compound of structure (I), the method comprising admixing a compound of structure (II) with a compound of formula M-L$^{1b}$-G', thereby forming at least one covalent bond by reaction of G and G', wherein:

M is a moiety comprising two or more carbon-carbon double bonds and at least one degree of conjugation;

L$^{1b}$ is an optional alkylene, heteroalkylene or heteroatomic linker; and

G' is a reactive group complementary to G.

The following examples are provided for purposes of illustration, not limitation.

EXAMPLES

General Methods

Mass spectral analysis was performed on a Waters/Micromass Quattro micro MS/MS system (in MS only mode) using MassLynx 4.1 acquisition software. Mobile phase used for LC/MS on dyes was 100 mM 1,1,1,3,3,3-hexafluoro-2-propanol (HFIP), 8.6 mM triethylamine (TEA), pH 8. Phosphoramidites and precursor molecules were also analyzed using a Waters Acquity UHPLC system with a 2.1 mm×50 mm Acquity BEH-C18 column held at 45° C., employing an acetonitrile/water mobile phase gradient. Molecular weights for monomer intermediates were obtained using tropylium cation infusion enhanced ionization on a Waters/Micromass Quattro micro MS/MS system (in MS only mode). Excitation and emission profiles experiments were recorded on a Cary Eclipse spectra photometer.

All reactions were carried out in oven dried glassware under a nitrogen atmosphere unless otherwise stated. Commercially available DNA synthesis reagents were purchased from Glen Research (Sterling, Va.). Anhydrous pyridine, toluene, dichloromethane, diisopropylethyl amine, triethylamine, acetic acid, pyridine, and THF were purchased from Aldrich. All other chemicals were purchase from Aldrich or TCI and were used as is with no additional purification.

Example 1

Synthesis of Dyes with Ethylene Glycol Spacer

Compounds with ethylene oxide linkers were prepared as followed:

The oligofluoroside constructs (i.e., compounds of structure (I)) were synthesized on an Applied Biosystems 394 DNA/RNA synthesizer on 1 µmol scale and possessed a 3'-phosphate group or 3'-S$_2$—(CH$_2$)$_6$—OH group or any of the other groups described herein. Synthesis was performed directly on CPG beads or on Polystyrene solid support using standard phopshoporamadite chemistry. The oligofluorosides were synthesized in the 3' to 5' direction using standard solid phase DNA methods, and coupling employed standard β-cyanoethyl phosphoramidite chemistry. Fluoroside phosphoramidite and spacers (e.g., hexaethyloxy-glycol phosphoramidite, triethyloxy-glycol phosphoramidite, polyethylene glycol phosphoramidite) and linker (e.g., 5'-amino-Modifier Phosphoramidite and thiol-Modifiers S2 Phosphoramidite) were dissolved in acetonitrile to make 0.1 M solutions, and were added in successive order using the following synthesis cycle: 1) removal of the 5'-dimethoxytrityl protecting group with dichloroacetic acid in dichloromethane, 2) coupling of the next phosphoramidite with activator reagent in acetonitrile, 3) oxidation of P(III) to form stable P(v) with iodine/pyridine/water, and 4) capping of any unreacted 5'-hydroxyl groups with acetic anhydride/1-methylimidizole/acetonitrile. The synthesis cycle was repeated until the full length oligofluoroside construct was assembled. At the end of the chain assembly, the monomethoxytrityl (MMT) group or dimethoxytrityl (DMT) group was removed with dichloroacetic acid in dichloromethane.

The compounds were provided on controlled-pore glass (CPG) support at 0.2 umol scale in a labeled Eppendorf tube. 400 µL of 20-30% NH$_4$OH was added and mixed gently. Open tubes were placed at 55° C. for ~5 minutes or until excess gases had been liberated, and then were closed tightly and incubated for 2 hrs (+/−15 min.). Tubes were removed from the heat block and allowed to reach room temperature, followed by centrifugation at 13,400 RPM for 30 seconds to consolidate the supernatant and solids. Supernatant was carefully removed and placed into a labeled tube, and then 150 µL acetonitrile was added to wash the support. After the wash was added to the tubes they were placed into a CentriVap apparatus at 40° C. until dried.

The products were characterized by ESI-MS (see Table 2), UV-absorbance, and fluorescence spectroscopy.

Example 2

Spectral Testing of Compounds

Dried compounds were reconstituted in 150 µL of 0.1M Na$_2$CO$_3$ buffer to make a ~1 mM stock. The concentrated stock was diluted 50× in 0.1 x PBS and analyzed on a NanoDrop UV spectrometer to get an absorbance reading. Absorbance readings were used along with the extinction coefficient (75,000 M$^{-1}$ cm$^{-1}$ for each FAM unit) and Beer's Law to determine an actual concentration of the stock.

From the calculated stock concentrations, ~4 mL of a 5 µM solution was made in 0.1M Na$_2$CO$_3$ (pH 9) and analyzed in a 1×1 cm quartz cuvette on a Cary 60 UV spectrometer, using a spectral range of 300 nm to 700 nm, to gauge overall absorbance relative to the group. From these 5 µM solutions, a second dilution was made at either 50 nM or 25 nM (also in 0.1M Na$_2$CO$_3$, pH 9) for spectral analysis on a Cary Eclipse Fluorimeter. Excitation was set at 494 nm and emission spectra were collected from 499 to 700 nm.

Figure 2:
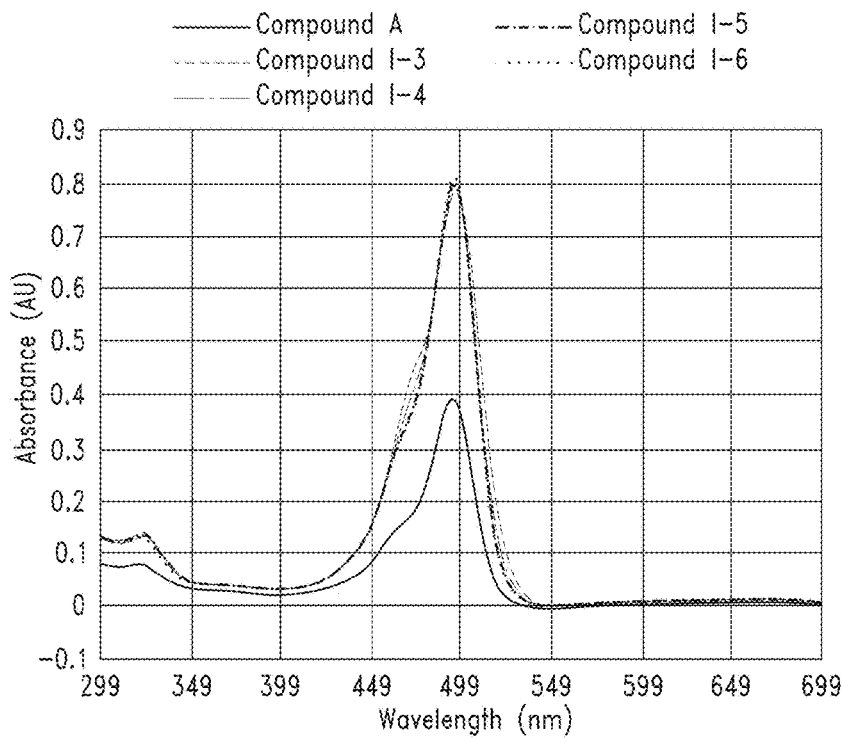
FIG. 2 is UV absorbance data for representative compounds comprising a hexaethylene glycol spacer and a comparative compound at 5 μm and pH 9.

FIG. 1 and FIG. 2 provide the UV absorbance of representative compounds of structure (I) and a comparative compound ("Compound A.") As seen in FIGS. 1 and 2, the UV extinction coefficient of representative compounds of structure (I) comprising two fluorescein moieties is approximately twice that of compound A.

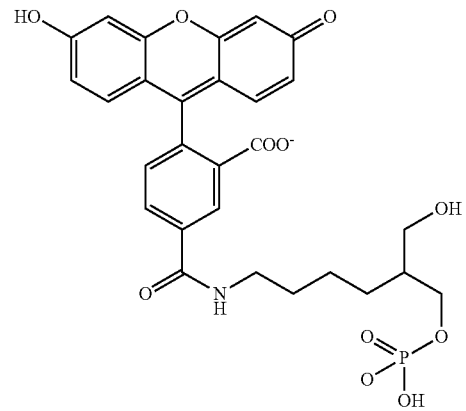

Compound A

Figure 3:
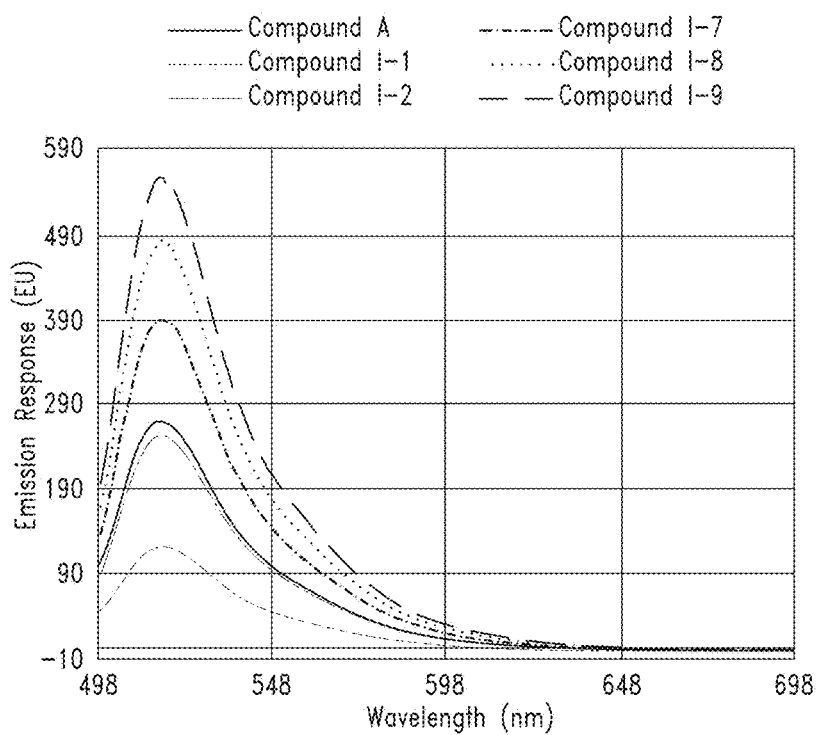
FIG. 3 is fluorescence emission spectra for representative compounds comprising a triethylene glycol spacer and a comparative compound at 50 nM and pH 9.
Figure 4:
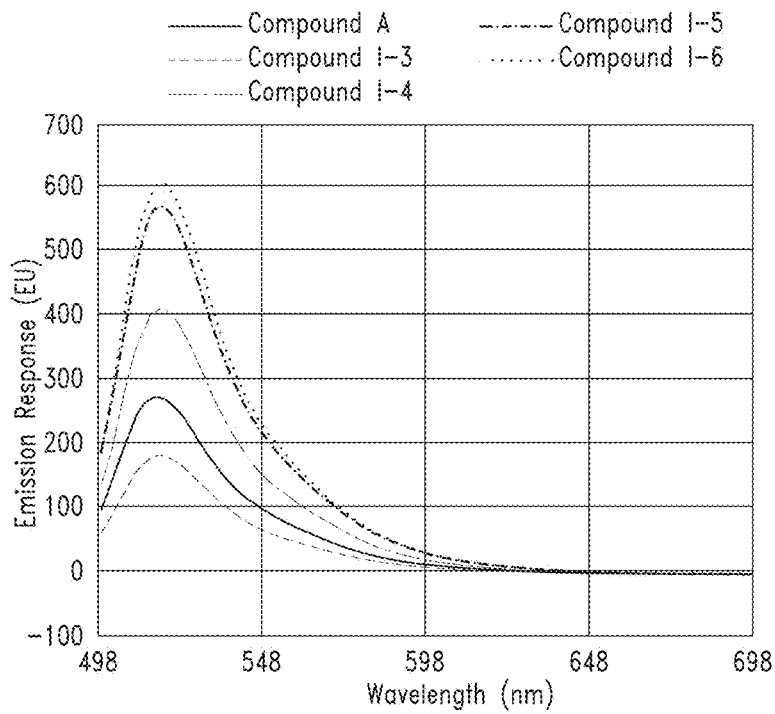
FIG. 4 presents fluorescence emission spectra for representative compounds comprising a hexaethylene glycol spacer and a comparative compound at 50 nM and pH 9.

The fluorescence emission spectra of representative compounds of structure (I) were also determined and compared to the emission spectrum of compound A. As demonstrated by the data in FIGS. 3 and 4, the fluorescence emission of representative compounds of structure (I) is higher than compound A, and the emission increases as the number of triethylene glycol or hexaethylene glycol units increases. While not wishing to be bound by theory, it is believed this unexpected increase in fluorescence emission is related to a decrease in internal quenching associated with the spatial distance provided by $L^4$.

Figure 5:
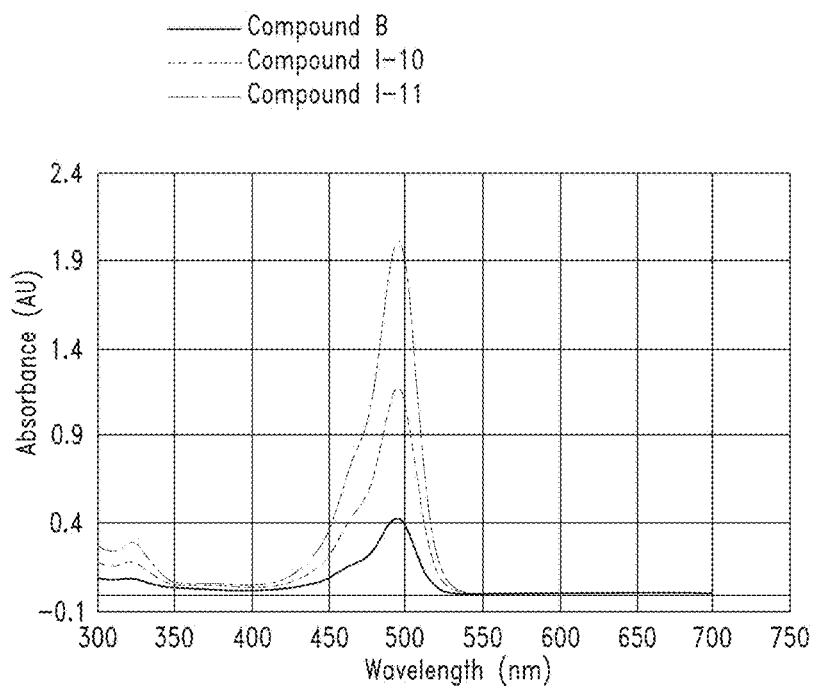
FIG. 5 is UV absorbance data at 5 μm for representative compounds comprising four hexaethylene glycol spacers and two or three fluorescein moieties relative to a comparative compound having a single fluorescein moiety.

Compounds I-10 and I-11 were tested to determine the effect of the number of M moieties on the UV absorbance and fluorescence emission of the compounds. FIG. 5 provides data comparing UV absorbance of compounds I-10 and I-11 to a comparative compound having a single M moiety ("Compound B") at 5 μm. At 5 uM, Compound B, which contains a single FAM unit absorbed at 0.43 AU, while compound I-10 (3 FAM units) absorbed at 1.17 AU and compound I-11 (5 FAM units) absorbed at 2.00 AU.

Compound B

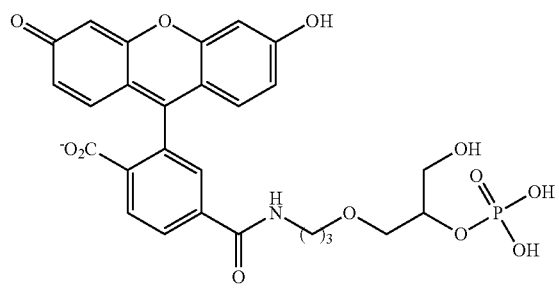

Figure 6:
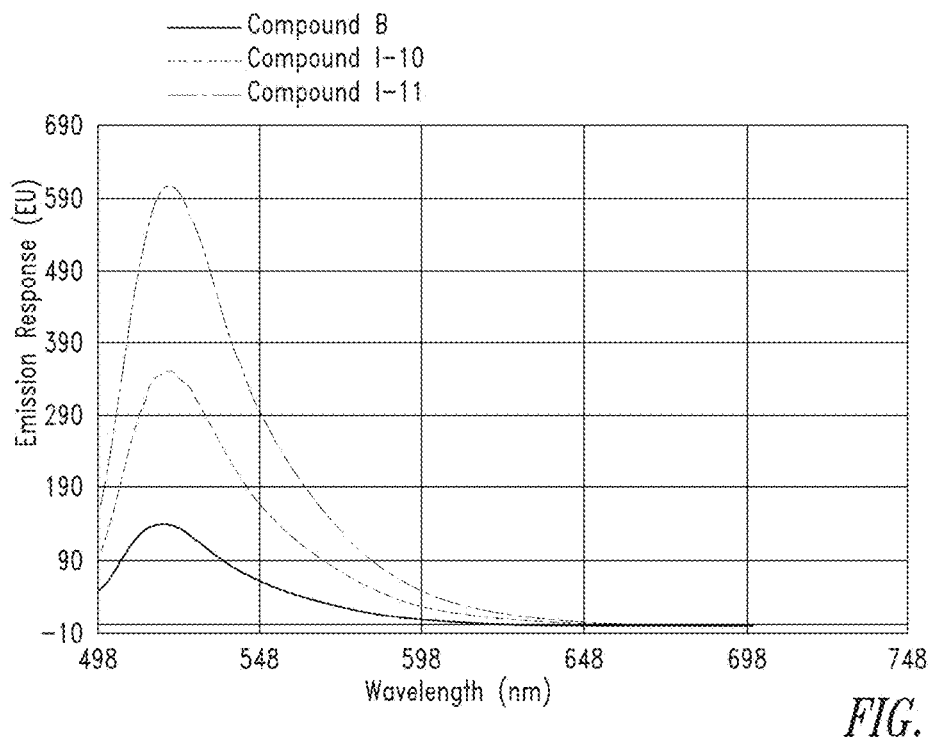
FIG. 6 is a graph of fluorescent emission data at 5 μm for representative compounds comprising four hexaethylene glycol spacers and two or three fluorescein moieties relative to a comparative compound having a single fluorescein moiety.

Fluorescence emission spectra for compounds I-10, I-11 and B at 25 nM are presented in FIG. 6. Rather than quenching (as more closely-spaced FAM units would do), compounds I-10 and I-11 showed emission responses that were increased by 2.5× and 4.3×, respectively, compared to the value of Compound B.

Example 3

Comparative Fluorescence Emission Response

Figure 7:
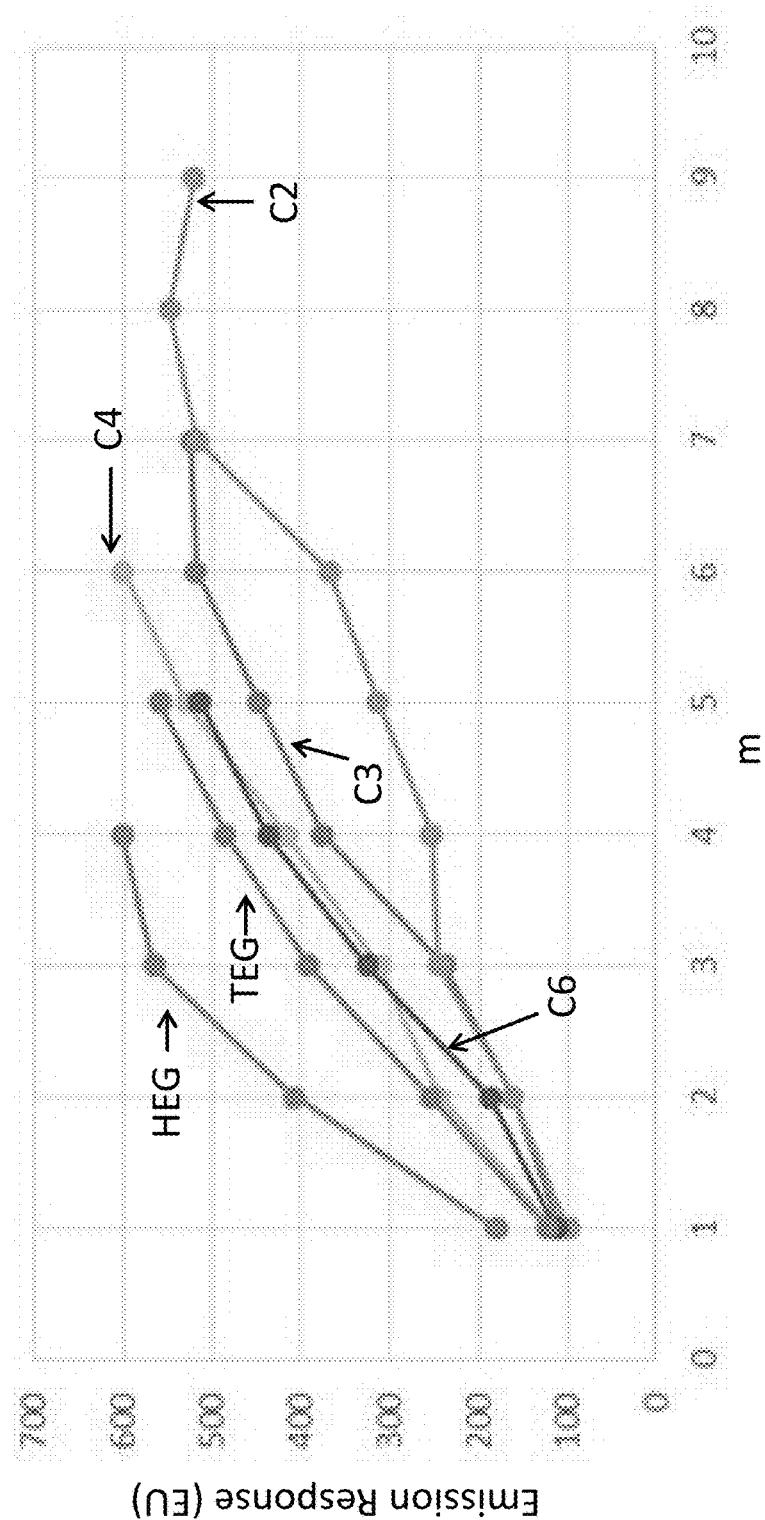
FIG. 7 shows comparative fluorescence emission response for illustrative compounds with various m values.

Compounds "HEG," "TEG," "C2," "C3," "C4" and "C6," wherein $R^2$ and $R^3$ are as defined for compound I-3 and m varied from 1 to 9, were prepared and their fluorescence emission spectra determined. Results are presented in FIG. 7. The data show that compounds according to embodiments of the present invention (i.e., HEG and TEG) have increased fluorescence emission with fewer repeating spacer moieties (i.e., lower values of m) relative to other dye compounds.

Figure 8:
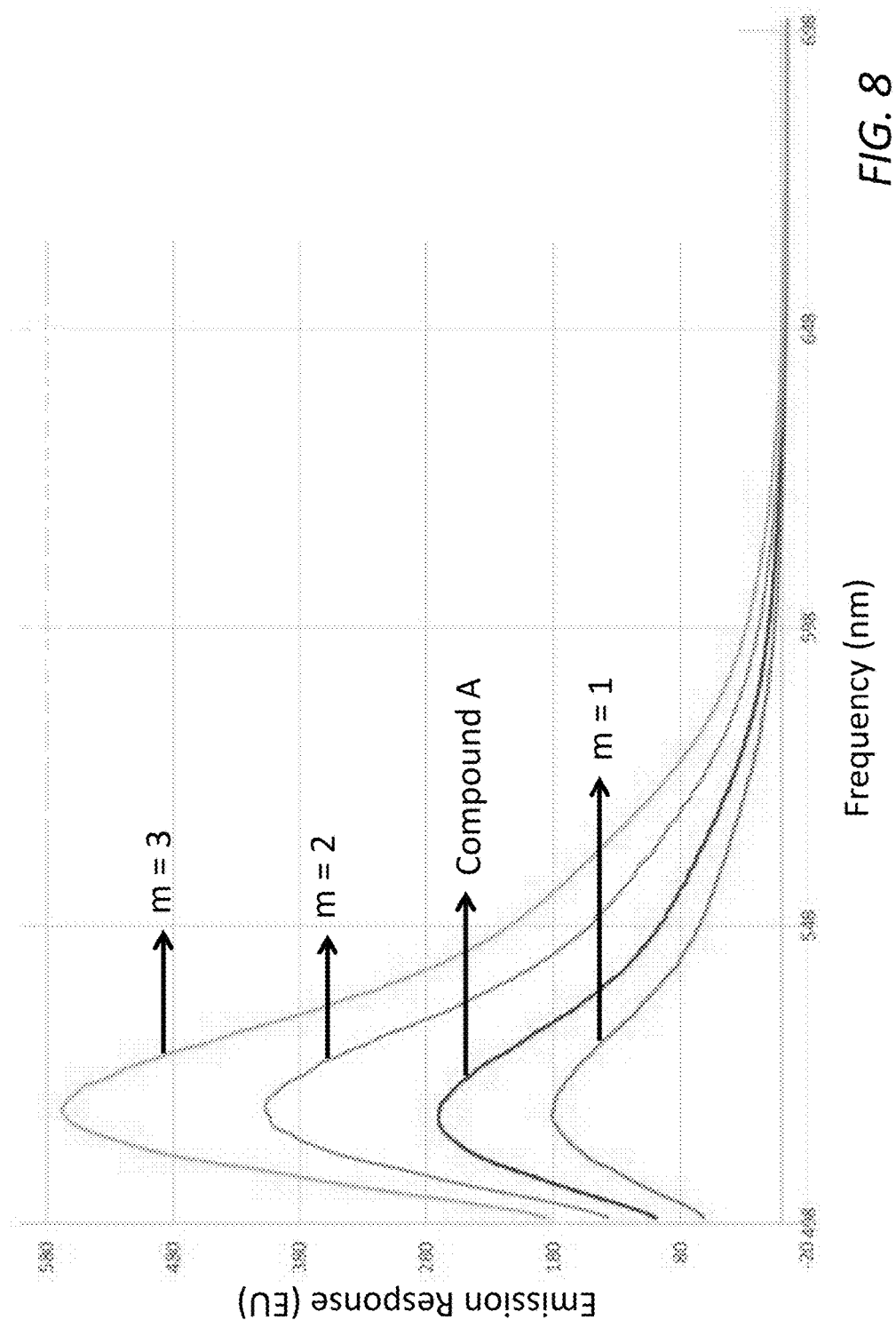
FIG. 8 provides data comparing fluorescence emission for the "HEG" compound, wherein m is 1, 2 or 3, relative to Compound A.

FIG. 8 provides data comparing fluorescence emission for the "HEG" compound, wherein m is 1, 2 or 3, relative to Compound A (50 nM, pH=9). The data show an increase in fluorescence emission for HEG relative to Compound A when m is greater than 2.

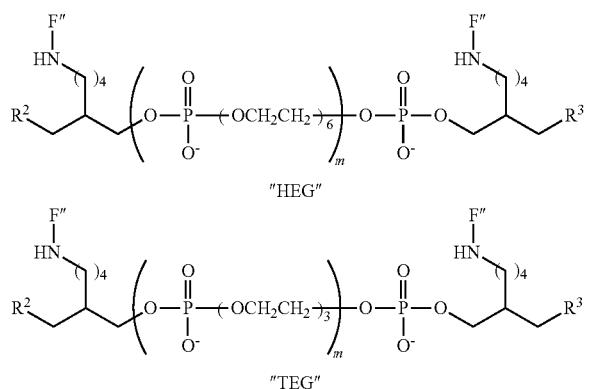

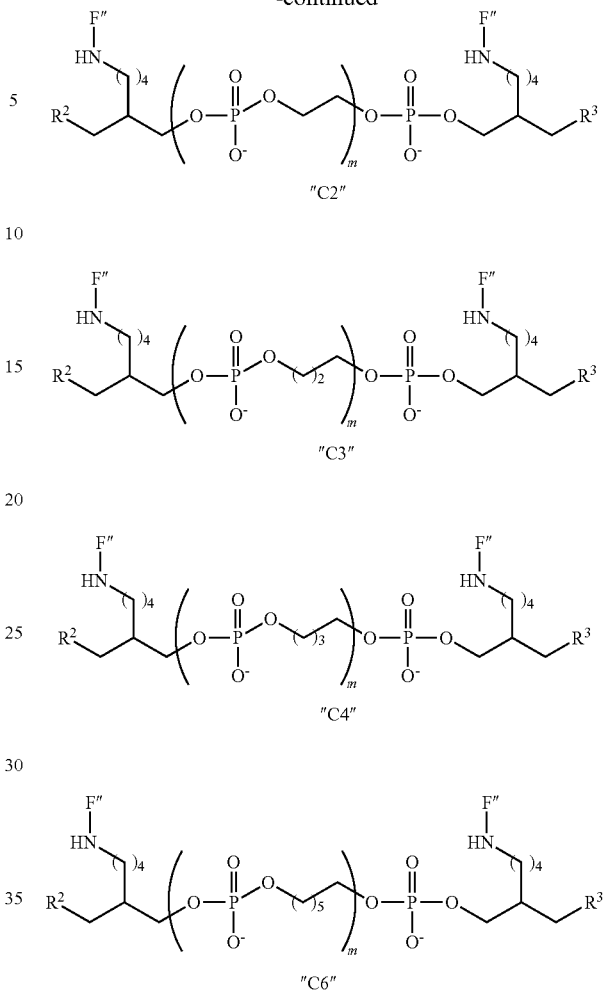

Preparation of Representative Compounds

Figure 9:
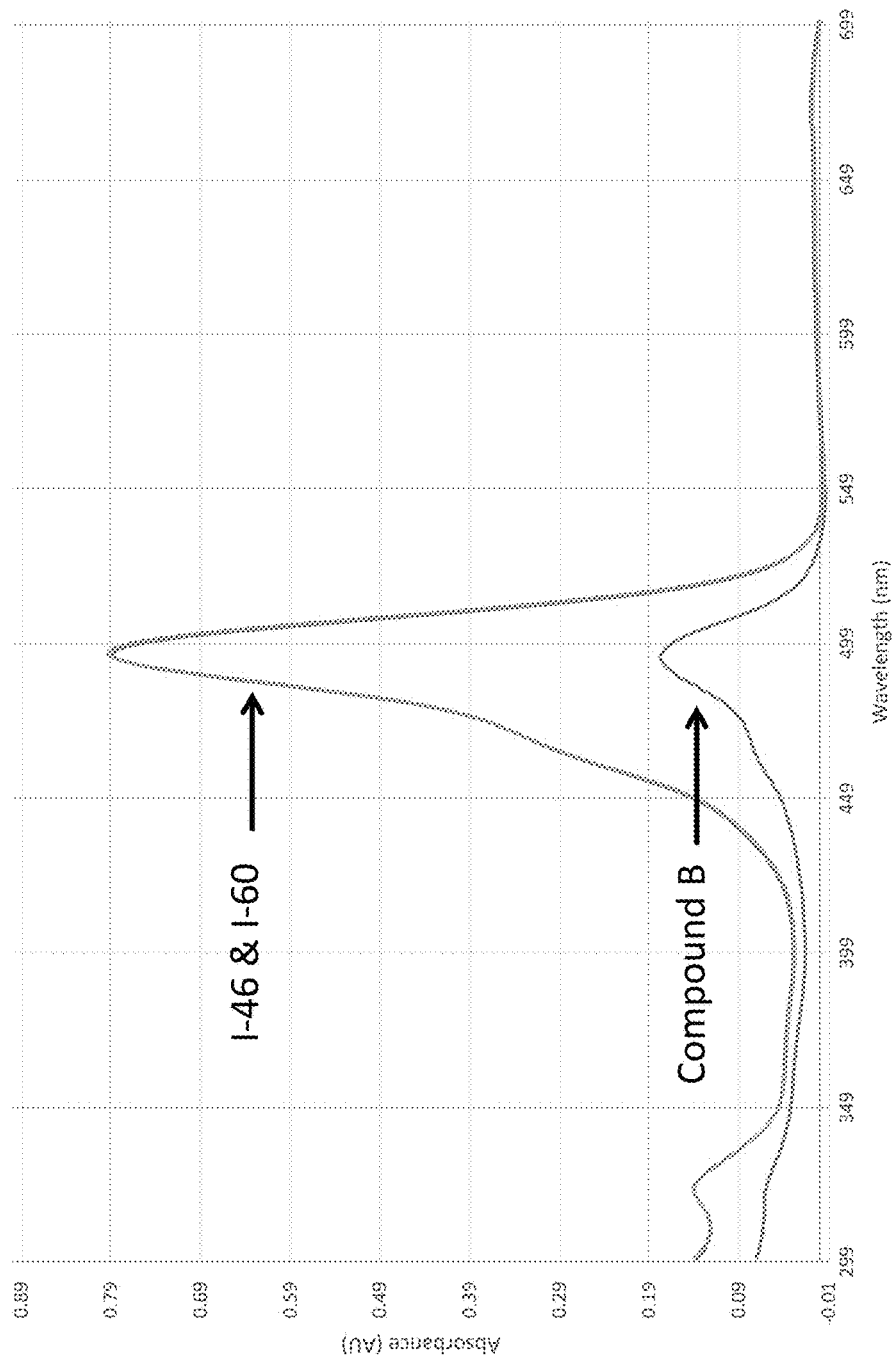
FIG. 9 provides UV absorbance data for compound I-32, compound I-46 and Compound B.

Compounds I-29, I-32 and representative analogues were prepared and tested to determine whether compounds wherein $L^4$ is a long linker (~1,000 dalton PEG) have similar properties to compounds with shorter $L^4$ linkers, but with multiple repeats (i.e., m is greater than 1). FIG. 9 provides UV absorbance data for compound I-60, compound I-46 and Compound B. The data show that compounds with long $L^4$ linkers have UV absorbance similar to those of compounds with multiple repeats of shorter linkers, and both compounds have increased absorbance relative to the control Compound B.

Example 5

Preparation of 99-Mer Dye

Compound I-42, having 33 fluorescein moieties was prepared using standard solid-phase oligonucleotide techniques as described herein. I-42 (represented by "A" in the below scheme) was trimerized as illustrated and described below to form a 99-mer dye.

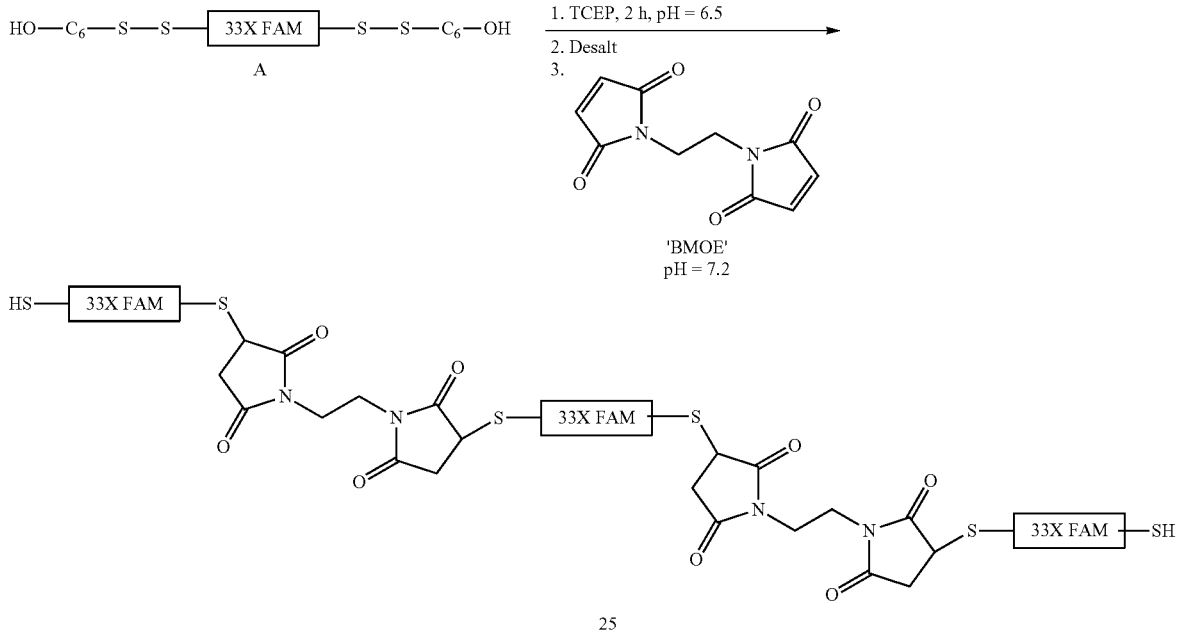

Figure 10:
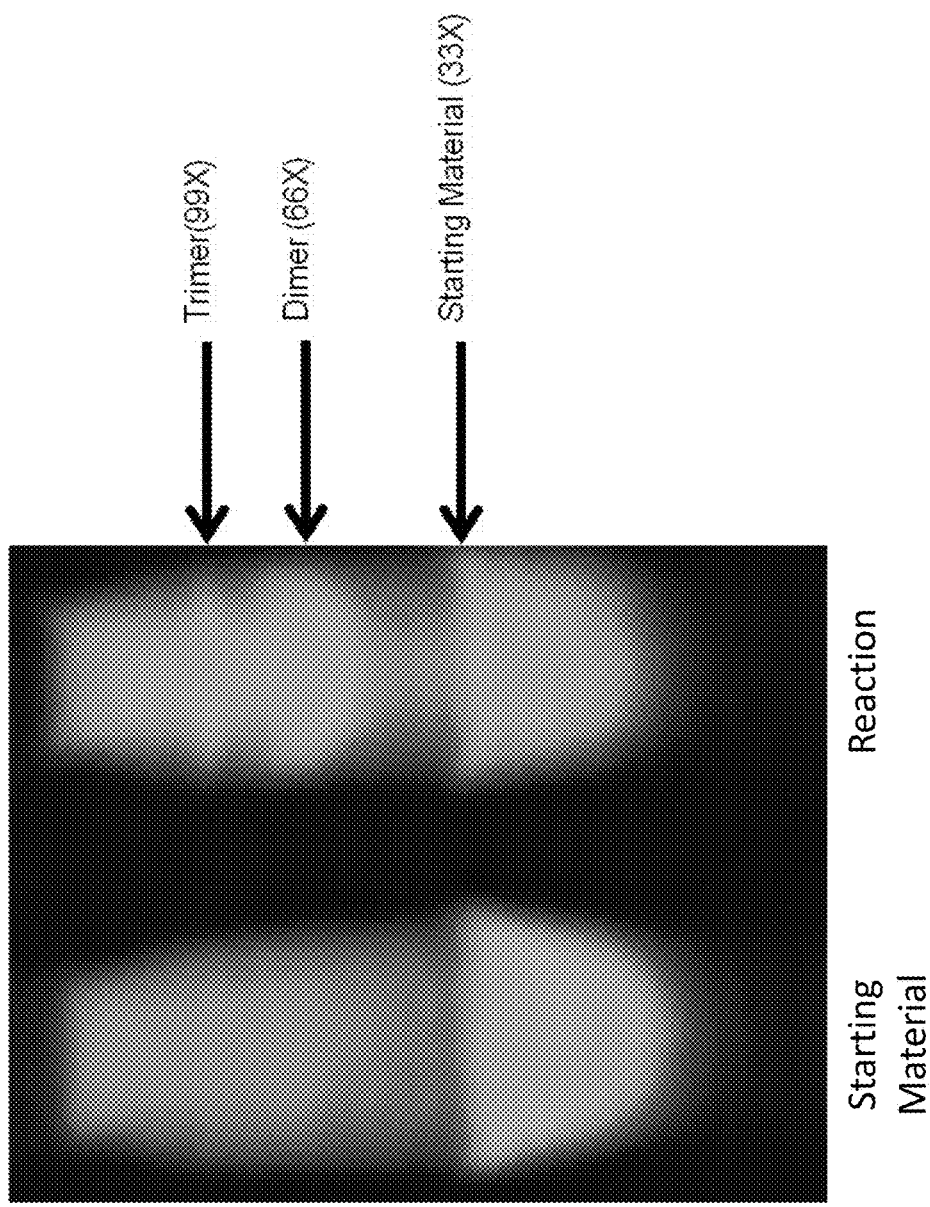
FIG. 10 shows the results of a reaction trimerizing compound I-42 as analyzed by PAGE.

In a 200 μL polypropylene tube was placed sodium phosphate buffer (3.5 μL, 100 mM, pH=6.5) and a solution of I-42 bis-disulfide (5.5 μL, 0.18 mM in water). To this was added a solution tris(2-carboxyethyl)phosphine (TCEP, 1.0 μL, 10 mM in water). The tube was capped, vortexed and allowed to incubate at room temperature for 2 h. The mixture was desalted through micro Zeba Spin desalting columns (Pierce, Cat#89877). The desalted solution was treated with sodium phosphate buffer (2.0 μL, 500 mM, pH=7.2) and a DMSO solution of bismaleimidoethane (BMOE, 1.0 μL, 0.25 mM) and incubated overnight at room temperature. The reaction mixture was diluted with water (100 μL) and analyzed by PAGE (FIG. 10, Invitrogen EC6875, 10% TBE-Urea gel, 180V constant, electrophoresis halted with resolution of highest MW species completed, visualized by UV illumination (365 nm)).

Other oligomer dyes having any desired number of dye moieties are prepared in an analogous manner.

Example 6

General Flow Cytometry Methods

Unless otherwise noted, the following general procedures were used in throughout the following Examples.
Lysis of Whole Blood:
Buffered Ammonium Chloride Method.

For staining of live cells, ethylenediaminetetraacetate (EDTA) anticoagulated normal human blood is bulk lysed with Ammonium Chloride solution (ACK), 15 mL blood to 35 mL lyse for 15 min at room temperature (RT). The cells were washed twice with 50% Hank's Balanced Salt Solution (HBSS) and 50% 1% Fetal Bovine Serum (FBS) 1× Dulbecco's Phosphate-Buffered Saline (DPBS) with 0.02% sodium azide. The cells were then re-suspended to 100 μL/test/0.1-1×10e6 in donor plasma. Cells in plasma were added to pre-diluted antibodies for $V_f$ of 1004, 1% Bovine Serum Albumin (BSA) and 1×DPBS with 0.02% sodium azide in polypropylene 96 well HTS plates. After incubating for 45 min. at RT, the cells were washed twice with 50% HBSS and 50%-1% FBS 1×DPBS with 0.02% sodium azide. Lyse/Fixation Method. Blood was lysed with 1.0 mL RBC lysing solution (ammonium chloride), 100-15 mL blood to 35 mL lyse for 15 min at RT. The cells were then washed twice with 50% HBSS and 50%-1% FBS 1×DPBS with 0.02% sodium azide. Cells were then re-suspended to 100 μL/test/1×10e6 in donor plasma. Pre-diluted antibodies were added in 1004, 1% BSA and 1×DPBS with 0.02% sodium azide. 100 μL cells were added to 96 well polypropylene HTS plates (total 200 μL test size). After incubation for 45 min. at RT the cells were washed twice with 50% HBSS and 50% 1% FBS 1×DPBS with 0.02% sodium azide.
Preparation of Antibody Conjugates:

Antibody conjugates were prepared by reacting a compound of structure (I) comprising a Q moiety having the following structure:

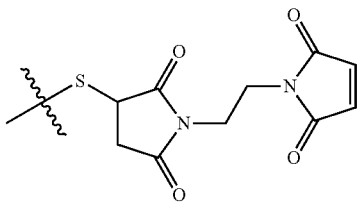 [SMILES: *SC1CC(=O)N(CCN2C(=O)C=CC2=O)C1=O]

with the desired antibody. The compound and antibody are thus conjugated by reaction of an S on the antibody with the Q moiety to form the following linking structure:

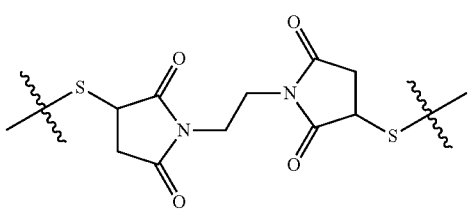 [SMILES: *SC1CC(=O)N(CCN2C(=O)CC(S*)C2=O)C1=O]

Antibody conjugates are indicated by the antibody name following by the compound number. For example, UCHT1-I-45 indicates a conjugate formed between compound I-45 and the UCHT1 antibody. If a referenced compound number does not include the above Q moiety in Table 2, it is understood that the Q moiety was installed and the conjugate prepared from the resulting compound having the Q moiety.

Dilution of Conjugates:

Antibodies were brought to RT. The antibody conjugates were diluted to concentrations in a range of 0.1-540 nM (8.0 micrograms or less per test) in a cell staining buffer (1×DPBS, 1% BSA, 0.02% sodium azide). In some examples, serial dilutions for each sample started at 269 nM antibody in cell staining buffer, and the antibody dilutions were kept protected from light until use. In other experiments, dilutions started at 4.0 μg antibody/test size, with the test size ranging from 100-200 μL. Titers were performed in two fold or four fold dilutions to generate binding curves. In some cases, 8.0 or 2.0 μg/test size were used in first well in a dilution series.

Flow Cytometry with Conjugate:

After physical characterization, the conjugates were tested for activity and functionality (antibody binding affinity and brightness of dye) and compared to reference antibody staining. Then the quality of resolution was determined by reviewing the brightness in comparison to auto-fluorescent negative controls, and other non-specific binding using the flow cytometer. Extensive studies of the mouse IgG1,k isotype control MOPC-21 conjugates were not included when testing I-45 because MOPC-21 non-specific binding was characterized during the testing of UCHT1-Compound C and UCHT1-I-45 in earlier tests. The I-45 conjugates were tested on Jurkat T cells, Ramos B cells, and a heterogeneous population of leukocytes in human blood or peripheral blood mononuclear cells (PBMC), and using polystyrene goat-anti-mouse Ig coated beads. Whole blood screening was the most routine for testing UCHT1 I-45 and its analogues. Bridging studies were implemented as new constructs were formed. Additional flow cytometry methods were used when testing conjugates (UCHT1-I-56, I-48, I-49, I-16, and I-21B) and compared to antibody conjugate references from Sony Biotechnology (UCHT1-FITC) and the key bridging references previously characterized (e.g. UCHT1-I-45, UCHT1-I-49) in most studies.

gate form. The I-45 dyes were tested on heterogeneous population of leukocytes in human blood when cells are treated with lysis and fixation solution, and when the blood is aged, or when applied to PBMC monocyte populations. Bridging studies ranking the affinity (Compound D, I-45, I-49, and I-16) were performed for dye lot comparisons while including dyes from very early studies when characterizing Compound D.

Compound D

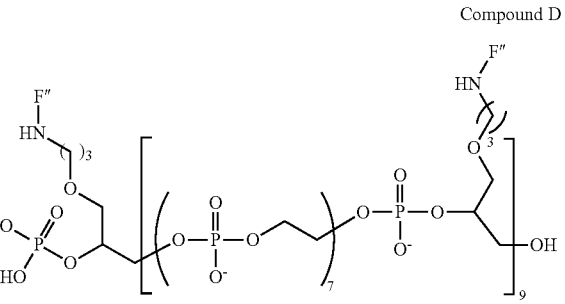

Flow Cytometry Workflow:

Cells were cultured and observed for visual signs of metabolic stress for dye screening or off target binding (data not shown), or fresh healthy cells were used for conjugate screening. Cells were counted periodically to check cell density (1×10e5 and 1×10e6 viable cells/mL). Antibody conjugates were diluted (preferably in plate or tubes) before harvesting cells in stain buffer (DPBS, 0.1% BSA, 0.02% sodium azide). Cells with a viability range of 80-85% were used. The cells were washed twice by centrifuging and washing cells with buffer to remove pH indicator, and to block cells with Ig and other proteins contained in FBS. The cell density was adjusted to test size in stain buffer. The cells were plated, one test per well, or dyes (pre-diluted) were applied to cells in plate. Then, the cells were incubated 45 min at 23° C. The cells were washed twice by centrifuging Compound C

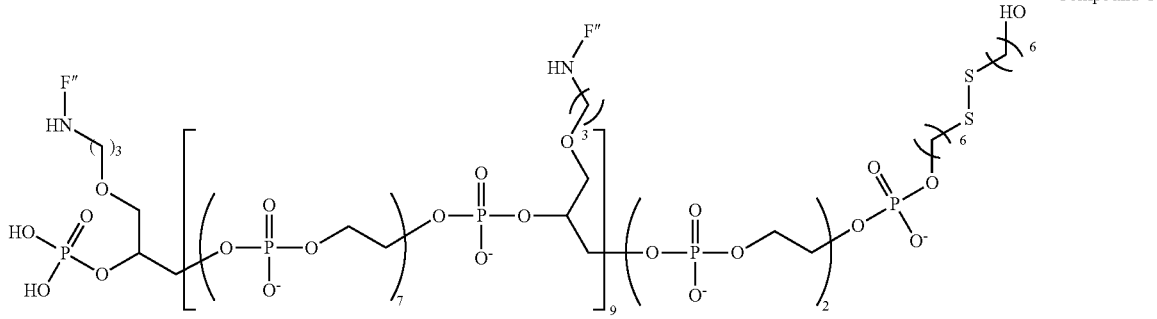

Perform Free Dye Flow Cytometry:

After molecular and physical characterization, the dyes were also tested for potential affinity to cells compared to a reference dye stain. Because dyes have the potential to also function as cellular probes and bind to cellular material, dyes can be generally screened against blood at high concentrations (>100 nM-to-10,000 nM) to ascertain specific characteristics. Expected or unexpected off target binding was then qualified by evaluating brightness and linearity upon dilution in comparison to auto-fluorescent negative controls, and other dye controls using the flow cytometer. Studies of Compound D (a Compound Cfree dye, but non-functionalized) was the positive control for bright off target binding of dyes and has been previously characterized when in conjuand washing cells with wash buffer, then aspirating the plate. The cells were re-suspended in acquisition buffer. 5000 intact cells were acquired by flow cytometry. The fluorescence of the dyes was detected by 488 nM blue laser line by flow cytometry with peak emission (521 nM) detected using 525/50 bandpass filter. At least 1500 intact cells, with target acquisitions of 3000-5000 intact cells, were acquired by flow cytometry and analyzed to identify viable cells present in the cell preparation.

Data Analysis Methods:

Descriptive Statistics.

The EC-800 software allows a user to collect numerous statistical data for each sample acquisition. Mean or Median Fluorescence Intensity (MFI) in the FL1-A channel was used to measure the brightness of an antibody-dye reagent when it was being interrogated by flow cytometry and when noise was reviewed. Other statistics were evaluated to determine dye characteristics and overall quality of the reagents including median Signal-to-Noise and absolute fluorescence (median or Geomean).

Histograms.

The flow cytometry events were gated by size on forward versus side scatter (cell volume versus cell granularity). Those cells were then gated by fluorescent emission at 515 nm for Mean Fluorescence Intensity (MFI). The data collected are presented as dual parameter histograms plotted as number of events on the y-axis versus fluorescent intensity, which is represented on a log scale on the x-axis. The data may be summarized by affinity curves, or histograms of relative fluorescence intensity.

Binding Curves.

MFI was chosen as it is the parameter that best measures the brightness of an antibody-dye reagent when it is being interrogated by FCM, this can be expressed as the geometric mean, median, or mean, and represent absolute fluorescence measurements. For comparison, where the noise can be highly characterized, a Signal-to-Noise ratio is reported as MFI, S/N. In Examples 7, 8, and 14, the MFI of the UCHT1-Compound C conjugates versus concentration is shown to demonstrate binding curves of the reagent.

Bi-Variate, Dual Parameter Histograms.

In some cases, the FCM events were not gated in order to review qualitative outputs, and data are expressed by cell granularity (SSC) versus dye fluorescence. This method allows for the overall evaluation of all populations recovered in whole blood.

Example 7

Figure 11:
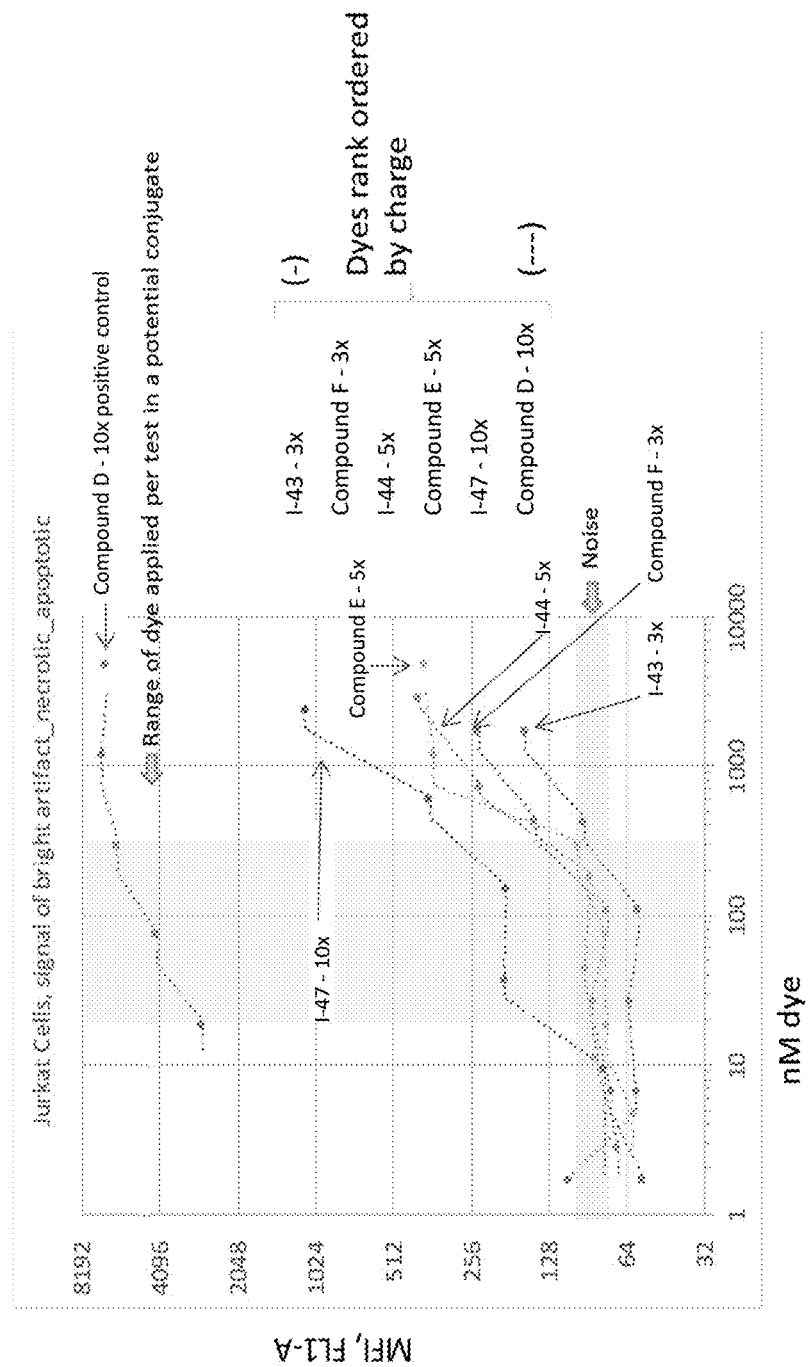
FIG. 11 provides data comparing the fluorescence signal of seven compounds in a dead and necrotic cell population.

Evaluation of Dyes for Non-Specific and Off Target Binding Using Necrotic and Apoptotic Populations of Heat Stressed Jurkat T Cells Jurkat cells were cultured according to instructions provided by American Type Culture Collection (ATCC), harvested live, heat stressed, washed 2-3×, and stained with conjugate antibodies. Staining was performed by applying cells to pre-diluted dyes and pre-diluted conjugated antibodies, incubating, washing, and then acquiring by flow cytometry. The dead and necrotic cell population (~10% of acquired cells) was evaluated for fluorescence signal. The results are shown in FIG. 11. As shown in FIG. 11, fluorescence is observed to be higher in 10× Compound D free dye compared to 10×I-47, 5× Compound E, 5×I-44, 3× Compound F, and 3×I-43.

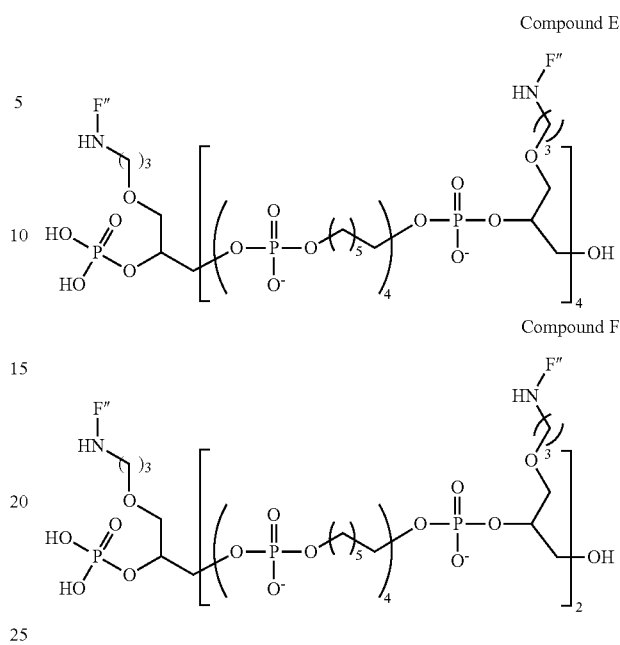

Example 8

Evaluation of Conjugates for Fluorescence Intensity: UCHT1-Compound G Vs. UCHT1-I-51

Viable Jurkat cells were cultured according to instructions provided by ATCC and harvested, then recovered at ~225 RCF for 6 minutes in a temperature controlled centrifuge set to 23° C. The supernatant was removed. Then the cells were washed twice in cell suspension buffer (calcium and magnesium free 1×DPBS, 1.0% FBS, 0.02% sodium azide, pH 7.2). After the second wash, the cells were centrifuged, the supernatant was removed, and the cells (~5×10$^5$ viable cells per sample) were re-suspended to test-size (final volume 100 µL). Cells were incubated with antibody dye conjugate solutions for 45 minutes at RT. After the incubation, samples were washed twice and then suspended in acquisition buffer.

Figure 12:
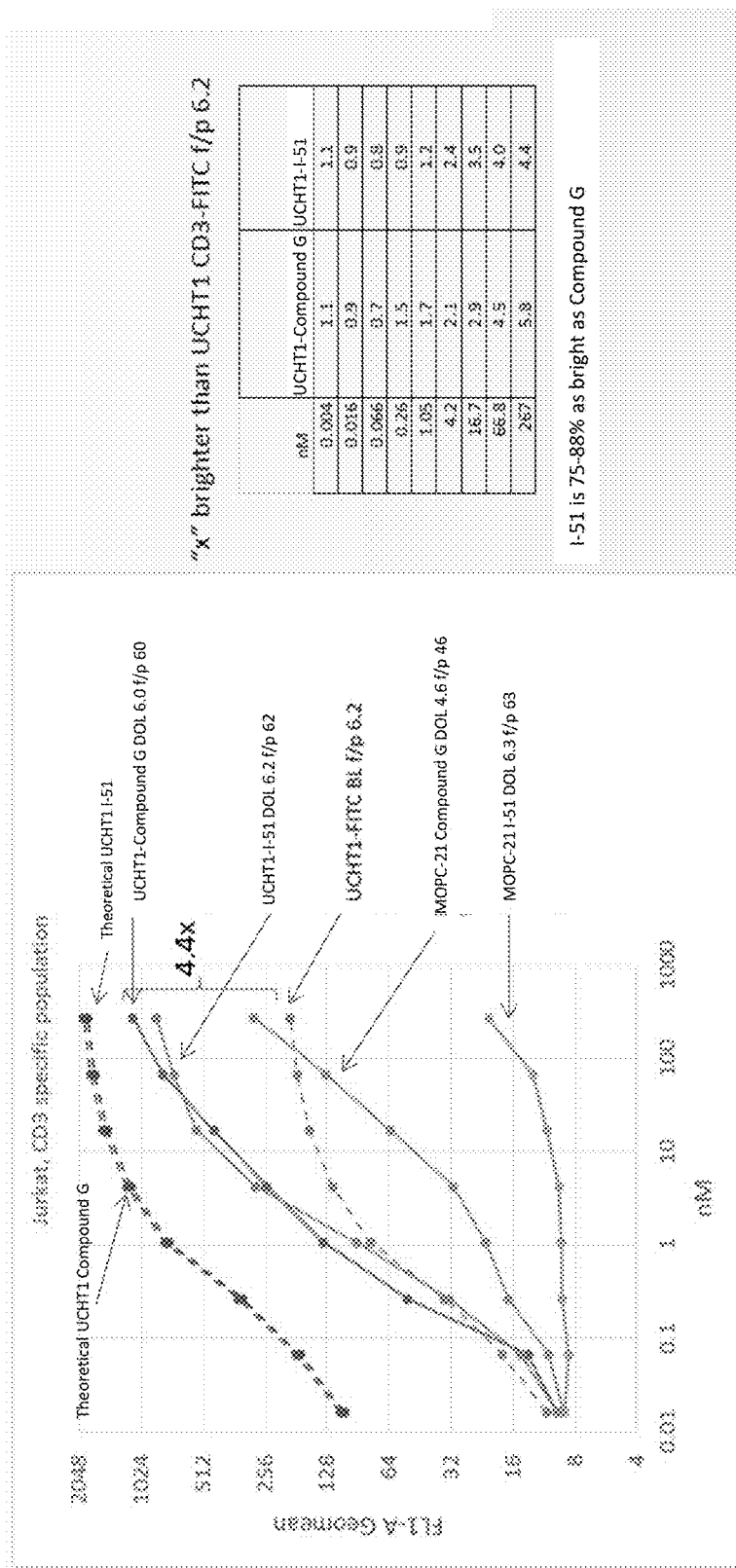
FIG. 12 shows fluorescence intensity of an antibody conjugate of I-51 versus an antibody conjugate of Compound G.

Data were acquired and evaluated on the SONY EC-800 FCM, and plotted nM of antibody protein versus geometric mean of relative fluorescence, as shown in FIG. 12. As can be seen, MOPC-21-Compound Ghas non-specific binding, yet both conjugates are 4-5× brighter than FITC reference. This example also shows that MOPC 21-I-51 shows reduced non-specific binding compared to UCHT1-Compound G conjugate (at these dye on label (DOL) levels).

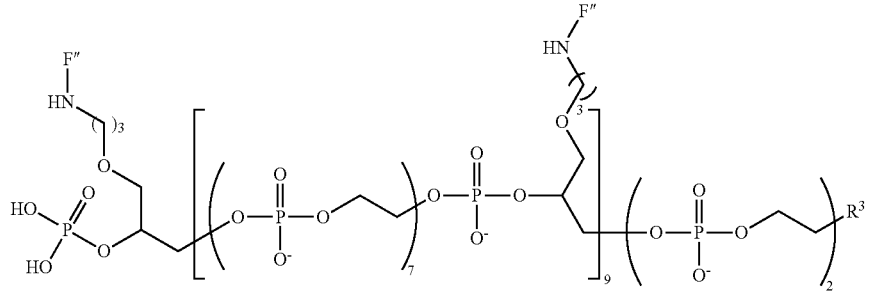

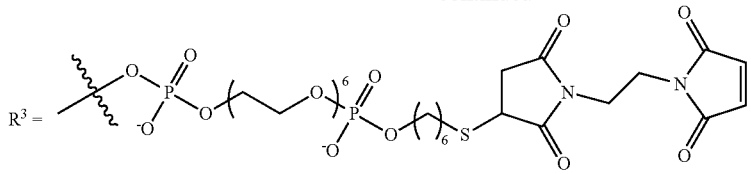

Example 9

Evaluation of CD3 Expression (Specificity and Resolution) in Heterogeneous Cell Sample and Peripheral Whole Blood Cells Whole blood was drawn from a normal donor into an EDTA stabilized sample tube for transport and short term storage. The blood was lysed with ACK, 15 mL blood to 35 mL lyse for 15 min at RT. The cells were washed twice with 50% Hanks Balanced Salt Solution (HBSS) and 50%-1% FBS 1×DPBS with 0.02% sodium azide. The cells were re-suspended to 100 µL/test/1×10e6 in donor plasma. Antibodies were pre-diluted in 1004, 1% BSA and 1×DPBS with 0.02% sodium azide, and were added to 100 µL cells in polypropylene 96 well HTS plates (total 200 µL test size). The cells were incubated for 45 min. at RT, washed twice with 50% HBSS and 50%-1% FBS 1×DPBS with 0.02% sodium azide, and re-suspended in 1% FBS 1×DPBS with 0.02% sodium azide.

Figure 13:
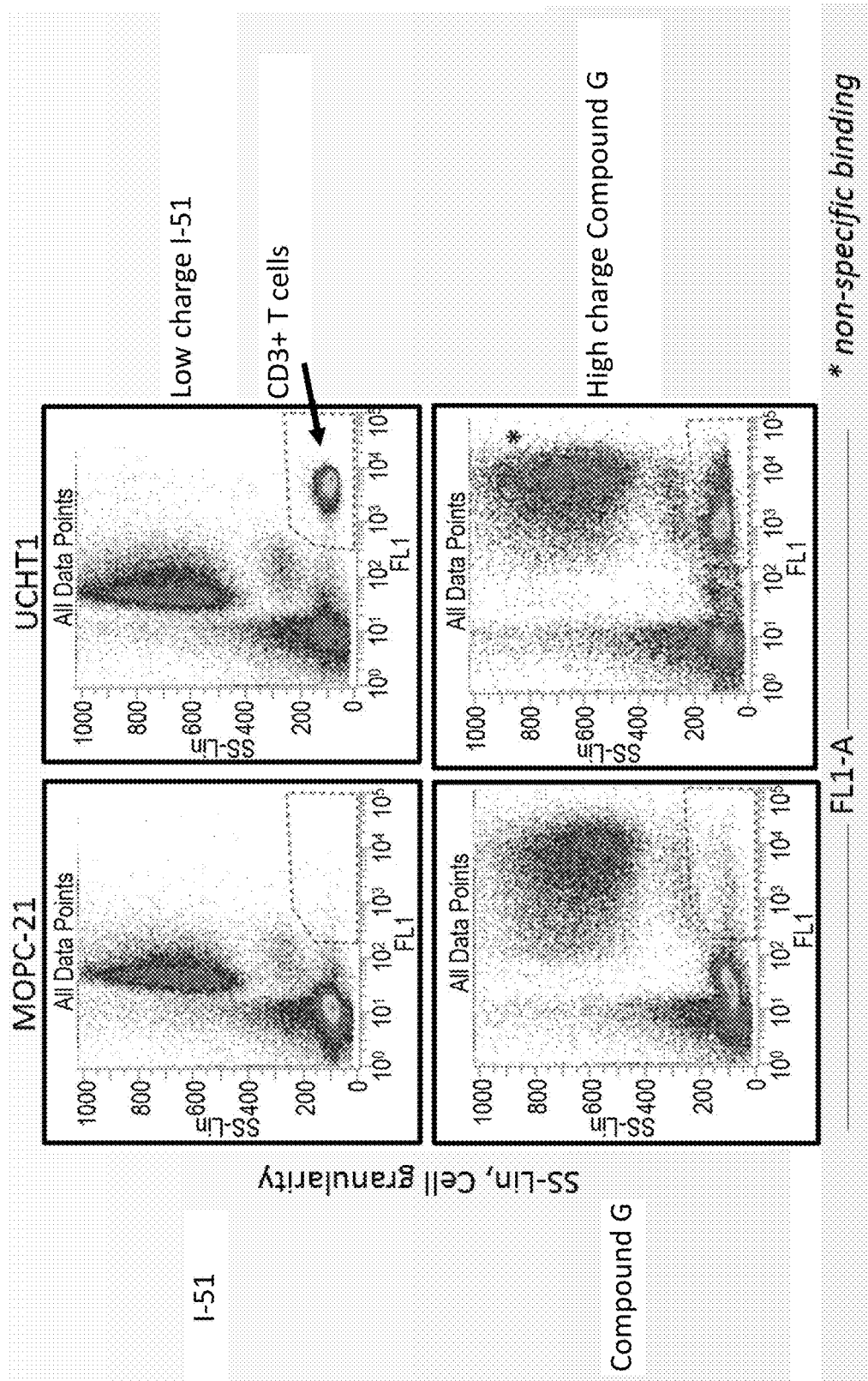
FIG. 13 shows comparisons of an I-51 conjugation and a Compound G reference antibody.

FIG. 13 shows comparisons of I-51 conjugation and Compound G reference antibody. In FIG. 13, the cell morphology (SSC-Lin) is shown in a dual parameter histogram with dye emission detected in the FL1-A channel. This shows the non-specific binding (NSB) of Compound G conjugate on heterogeneous population of cells, primarily neutrophils and monocytes while I-51 conjugates do not show NSB. The NSB of UCHT1-Compound G in lysed whole blood, effectively reduces the available antibody for binding to CD3

Figure 14:
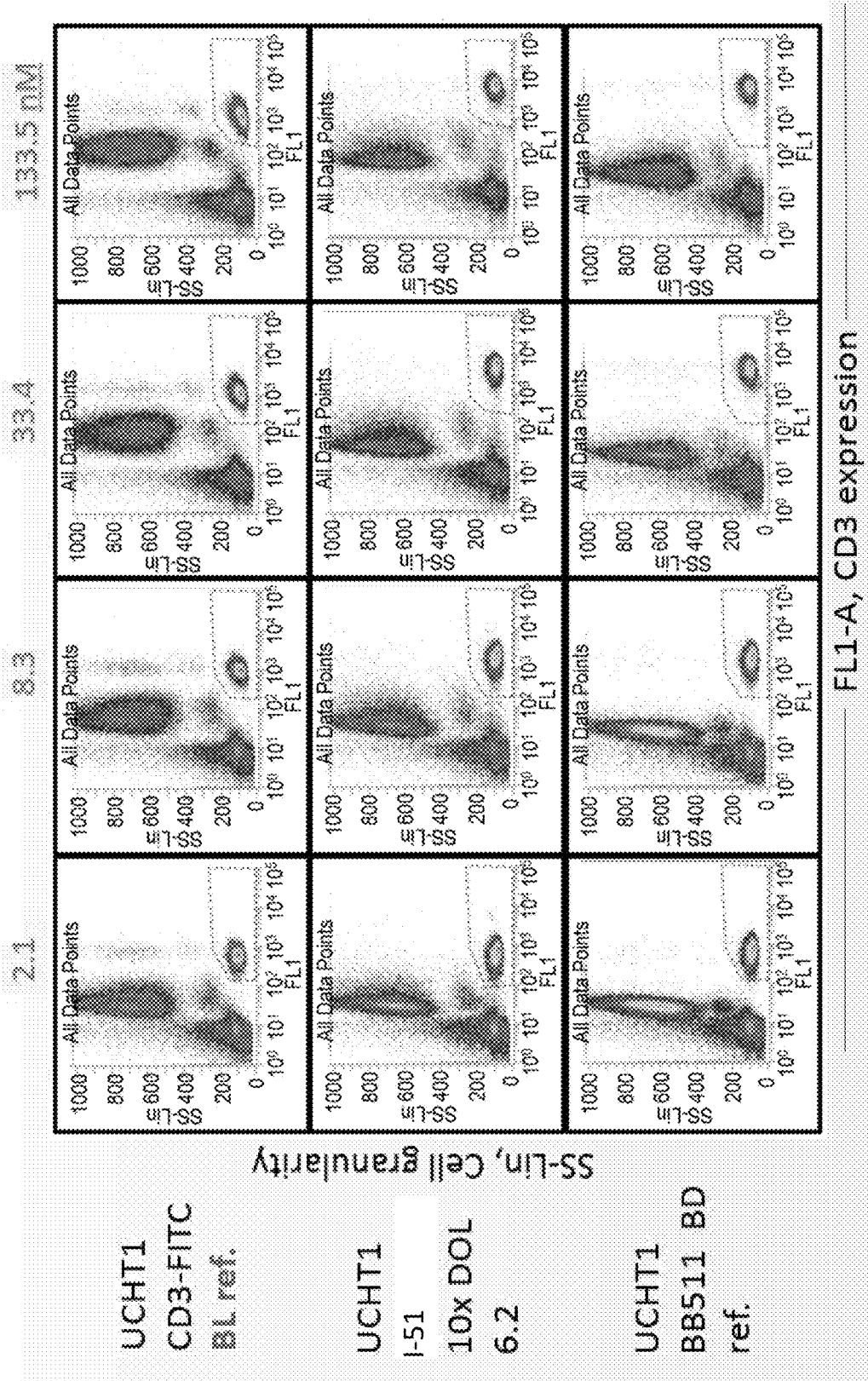
FIG. 14 shows a comparison of UCHT1-I-51, UCHT1-BB515, and UCHT1-FITC.

FIG. 14 shows a comparison of UCHT1-I-51, UCHT1 BB515, and UCHT1-FITC. UCHT1-I-51 is 6× brighter than UCHT1-FITC.

Example 10

Expression Levels of CD3 Compared to a Molecules of Equivalent Fluorochrome (MEF) Standard Curve Using lysed whole blood, high antigen density CD3 expression was visualized by fluorescence intensity results and compared to 6-Peak (or 8-peak) bead fluorescence outputs (Sony Biotech, Cat. No. AE700520) to estimate MEF Values. UCHT1-FITC, used as a reference, UCHT1-Compound G, and UCHT1-I-51, as well as UCHT1-BB515, used as an additional reference conjugate, were compared in the same experiment using standards. 6 Peak Beads consisted of a mixture of 3.8 micron beads of 6 different fluorescence intensities and were used to verify the linearity and sensitivity of the instrument and to estimate MEF when run in parallel in a given protocol.

Figure 15:
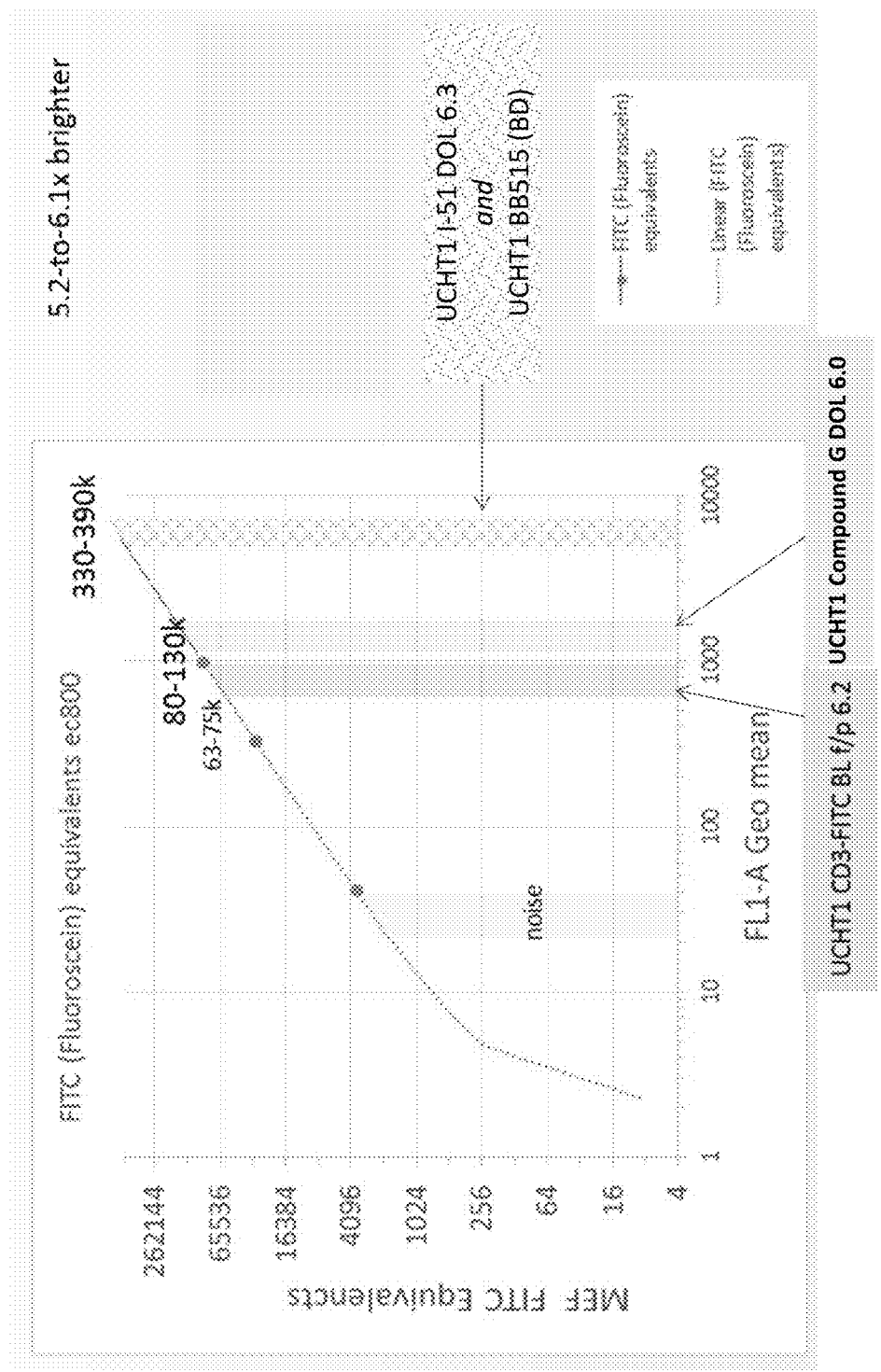
FIG. 15 shows expression levels of CD3 compared to a MEF standard curve.

FIG. 15 shows expression levels of CD3 compared to a MEF standard curve. As can be seen, I-51 is approximately 6× brighter than the reference, and Compound G is about 2× as bright. Concentration ranges shown are 133 nM and below. Note that, in comparison, FIG. 13 shows that the non-specific binding of UCHT1-Compound Gin lysed whole blood effectively reduced the available antibody for binding to CD3.

Example 11

Comparison of UCHT1 I-16 Fractions to FITC and I-56 Conjugates Beads were Pre-Treated (Vortexed and Sonicated) and Washed, and Bead counts calibrated to a 2×C dilution as determined in preliminary experiments to optimize acquisitions and target a linear saturation curve. Beads were incubated with antibody conjugates, washed, and then acquired by flow cytometry. BSA solution 0.1% in 1×DPBS was used for bead dilutions, washing, and acquisition. The antibodies were pre-diluted in 1% BSA Stain Buffer in 96 well polypropylene plates starting at 4.0 µg in a 200 µL volume in first well, and then serial diluted 100 µL in each subsequent well for at least 8 dilutions, (two fold). Thoroughly vortexed beads (at 2×C) were then added, and 100 µL of beads were added to 100 µL of antibody in each well. The beads were incubated for 20 minutes at RT, washed, and acquired by flow cytometry.

Figure 16:
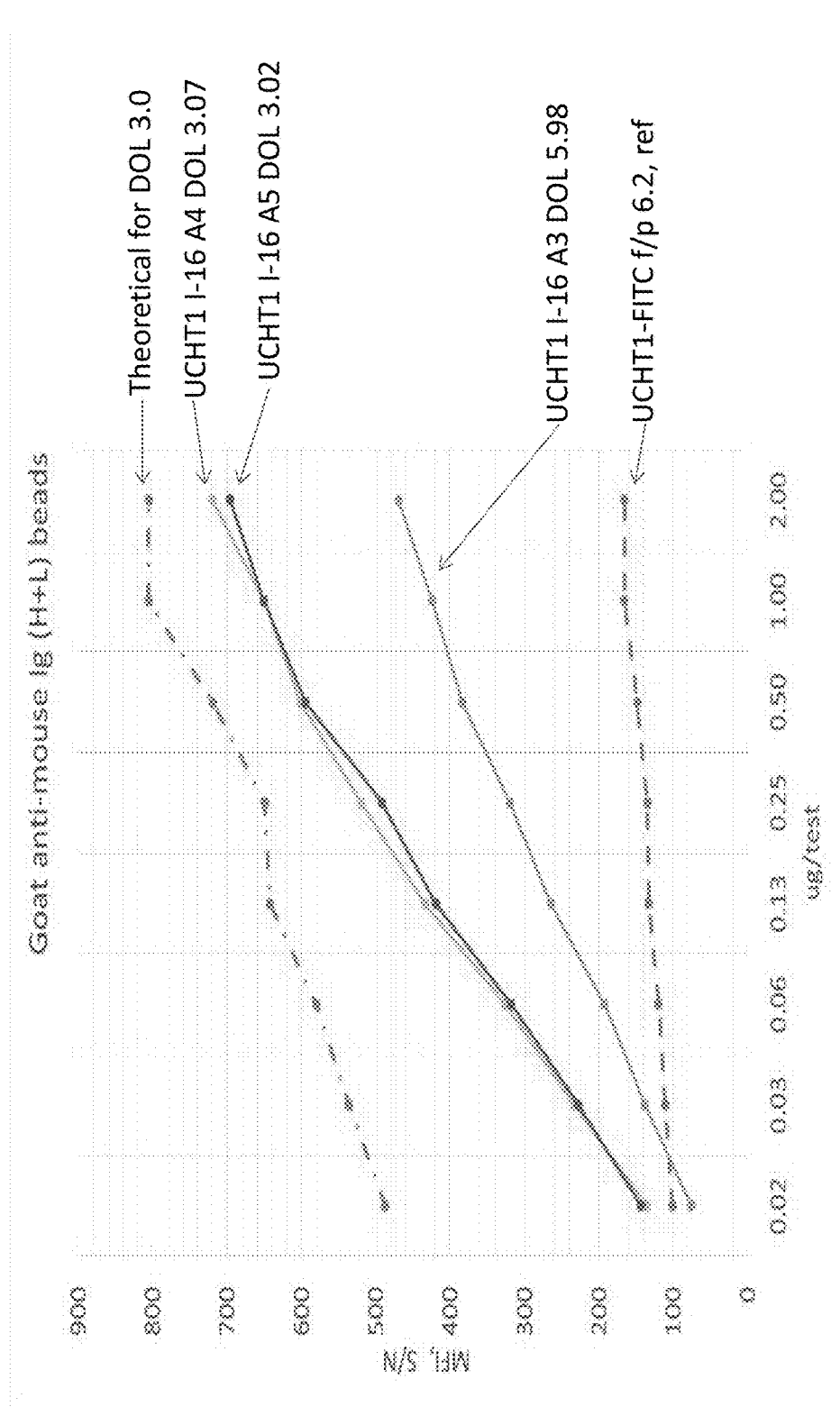
FIG. 16 shows a comparison of UCHT1-I-16 fractions to FITC.
Figure 17:
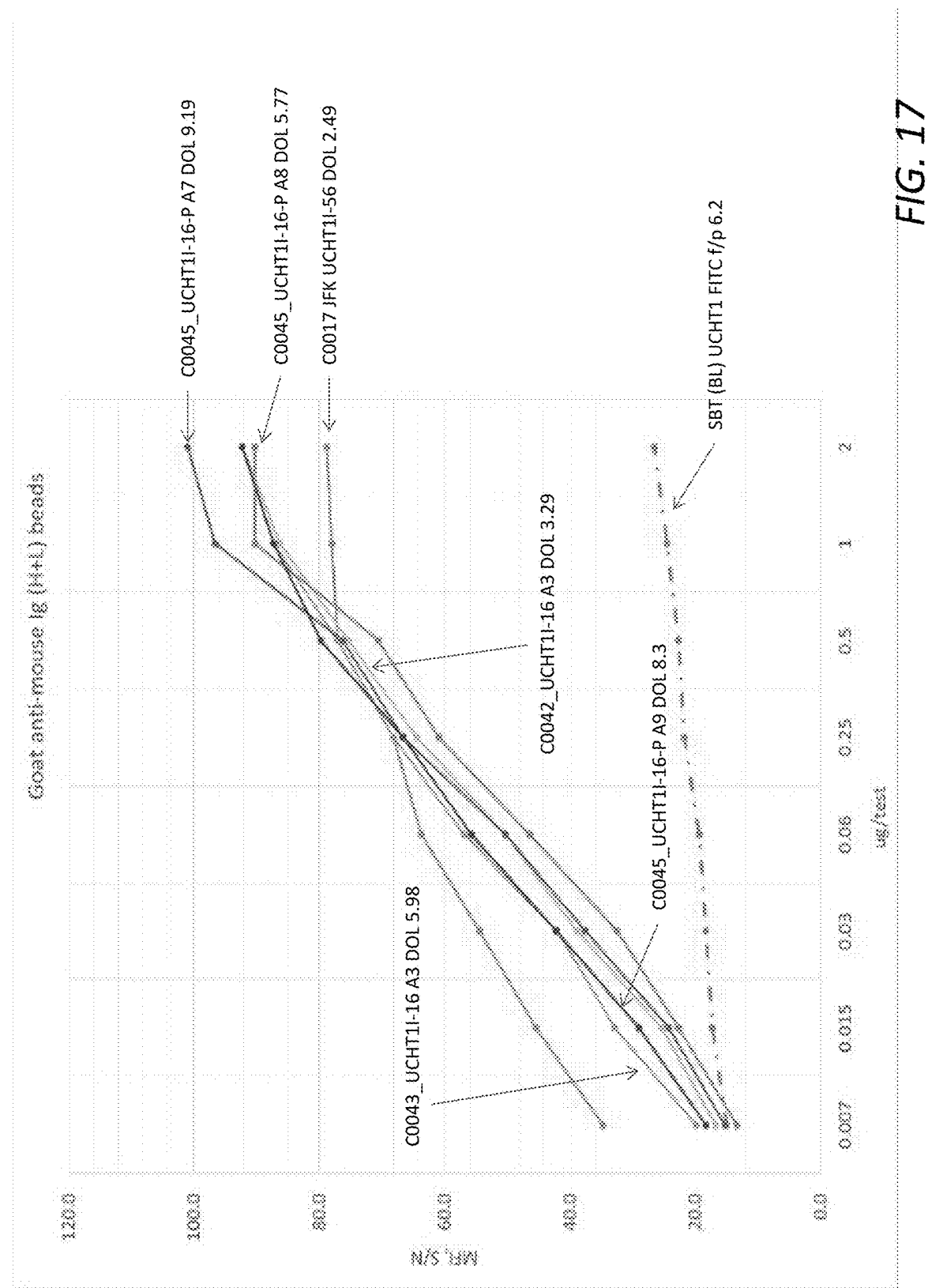
FIG. 17 shows a comparison of UCHT1-I-16 fractions to I-56 conjugates.

The results are shown in FIG. 16. UCHT1-I-16 at DOL ~3.0 approached theoretical maximum. As shown in FIG. 17, a similar experiment was performed to highlight the affinity curve differences noted between UCHT1-I-16 and the bridging reference with a longer tether, UCHT1-I-56.

Example 12

UCHT1 I-51-Like Analogue, UCHT1 I-16, Compared to UCHT1 I-56 (10×), and UCHT1 I-53 (6×)

Peripheral WBC were treated with lysis buffer, buffered ACK, for 20 minutes at 25° C., while slow rocking, then centrifuged and the lysis buffer removed. The cells were washed once with HBSS, pH 7.2, then 1×HBSS containing 0.5% FBS, and 0.02% Sodium Azide, pH 7.2, and re-suspended in Staining Buffer (1×DPBS, 1% BSA, 0.02% Sodium Azide, Ph 7.2). Cells were then applied to pre-diluted conjugated antibodies and incubated for 40 minutes at 23-25° C. protected from light.

Figure 18:
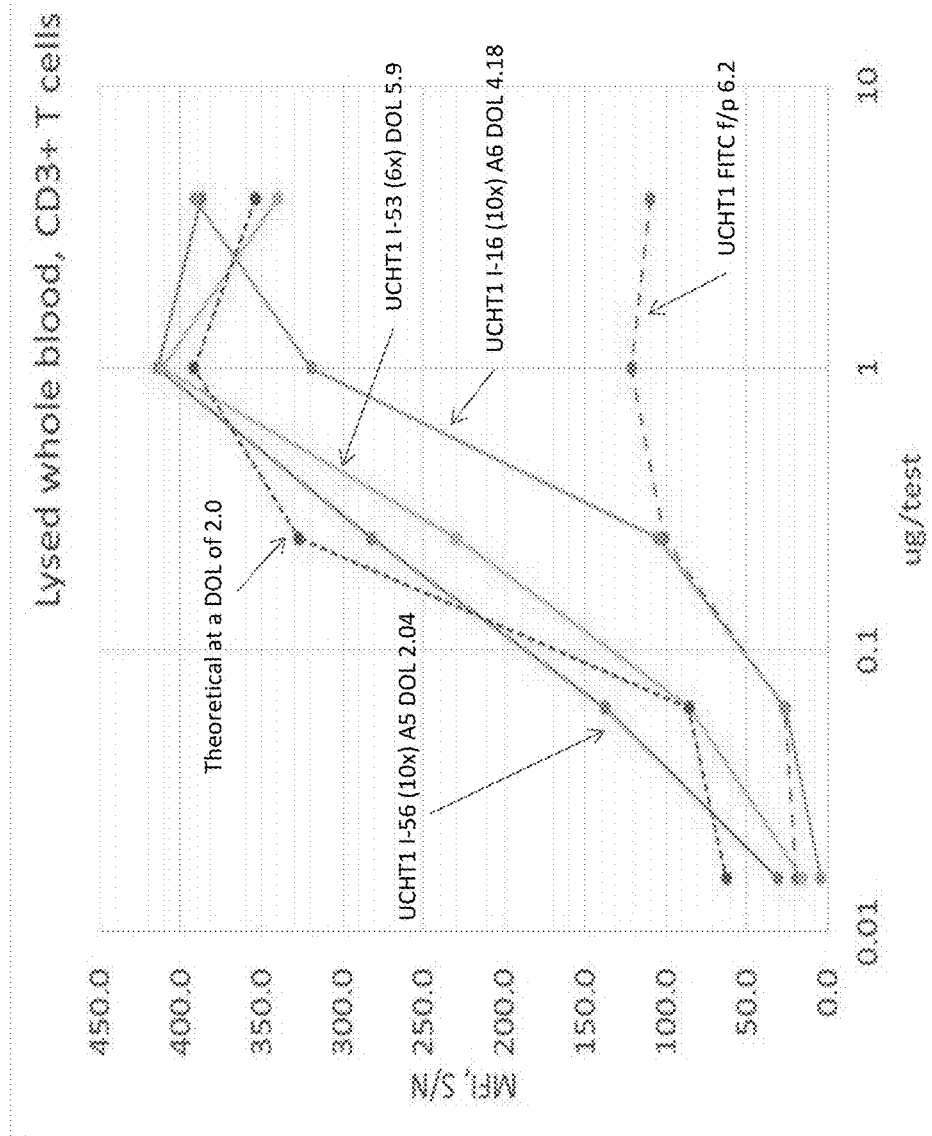
FIG. 18 shows a comparison of the UCHT1-I-51-like analogue, UCHT1 I-16, with UCHT1 I-56 (10×), and UCHT1 I-53 (6×).

FIG. 18 shows a comparison of the UCHT1-I-51-like analogue, UCHT1-I-16, with UCHT1-I-56 (10×), and UCHT1-I-53 (6×).

Example 13

UCHT1 I-51-Like Analogue, UCHT1 I-16, Compared to UCHT1 I-56 (10×), and UCHT1 I-53 (6×)

Figure 19:
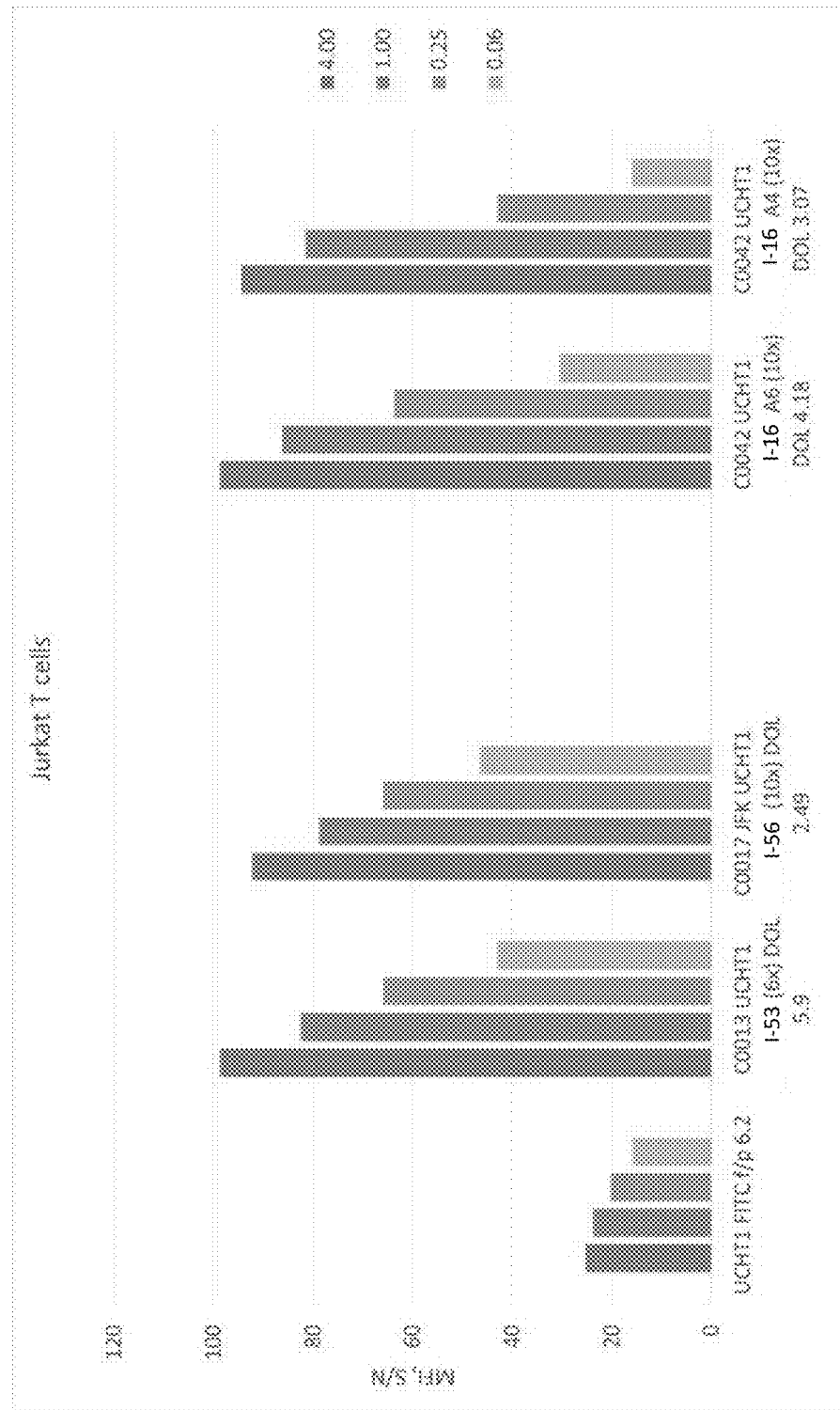
FIG. 19 provides data comparing the UCHT1 I-51-like analogue, UCHT1 I-16, was compared with UCHT1 I-56 (10×), and UCHT1 I-53 (6×).

Antibodies were evaluated for specific binding and fluorescence resolution by flow cytometry. Jurkat cells were cultured according to instructions provided by ATCC and harvested live. Staining was performed when cells were applied to pre-diluted conjugated antibodies, incubated for 20-40 minutes, washed, and then acquired by flow cytometry. The UCHT1-I-51-like analogue, UCHT1-I-16, was compared with UCHT1-I-56 (10×), and UCHT1-I-53 (6×). The results are shown in FIG. 19.

Example 14

Comparison of UCHT1 Conjugate Resolution by Regression Analysis

Cells were isolated from peripheral whole blood, and frozen in freezing buffer. Cells were thawed, rested, treated with autologous plasma to block FcR and to mimic a whole blood environment, washed two to three times, and then stained with conjugate much like when using whole blood. Beads were pre-calibrated to optimize acquisitions and target saturation in an antibody staining. Beads were incubated with antibody conjugates, washed, and then acquired by flow cytometry.

Figure 20:
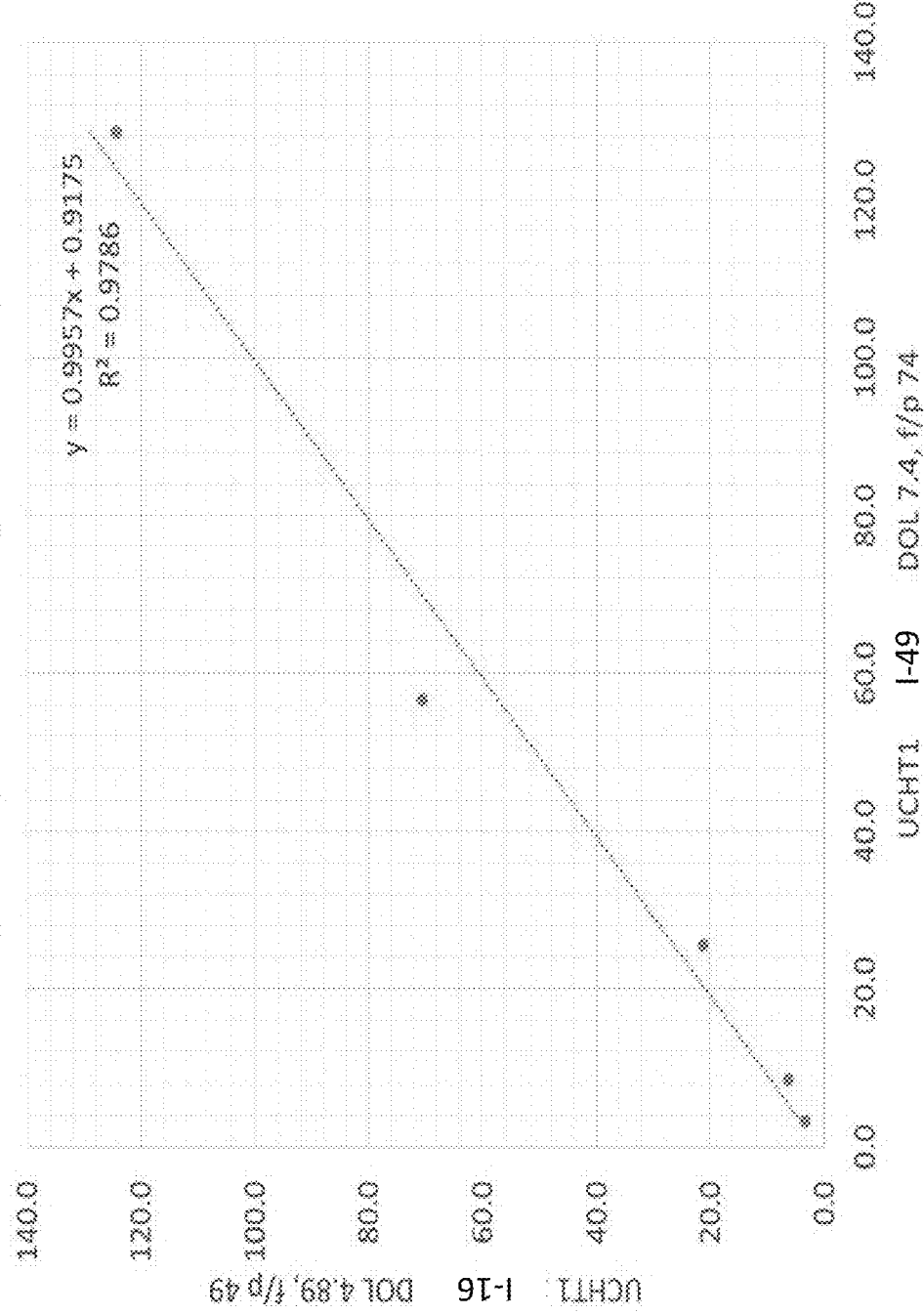
FIG. 20 shows the results of a regression analysis performed on data produced when testing UCHT1 I-16 and UCHT1 I-49 conjugates to demonstrate equivalency between conjugations.

Regression analysis was performed on data produced when testing UCHT1-I-16 and UCHT1-I-49 to demonstrate equivalency between conjugations. The results are shown in FIG. 20.

Example 15

I-49 and I-16 Affinity Testing of Raw Dye in Whole Blood

The dye was screened using the stain, lyse, fix, and wash whole blood method to evaluate background in three populations, monocytes, granulocytes, and lymphocytes, in an equivalency test in the presence of excess dye. Granulocytes present in the whole blood were chosen as the main target for analyses. Although lymphocytes and monocytes were also studied, data are not shown in regression graphs.

The raw dye was used in excess (first titration starting at 10,000 nM) without antibody conjugate being present in order to highlight, but also qualify, non-specific binding differences between the two nearly identical constructs. Peripheral WBC were treated with lysis buffer, buffered ACK, for 20 minutes at 25° C., while slow rocking, centrifuged, and the lysis buffer removed. A red cell lysis and fixation solution was applied to the dye and cells, and the cells were then washed once with HBSS, pH 7.2, then 1×HBSS containing 0.5% FBS, and 0.02% Sodium Azide, pH 7.2, and then re-suspended in Staining Buffer (1×DPBS, 1% BSA, 0.02% Sodium Azide, pH 7.2).

Figure 21A:
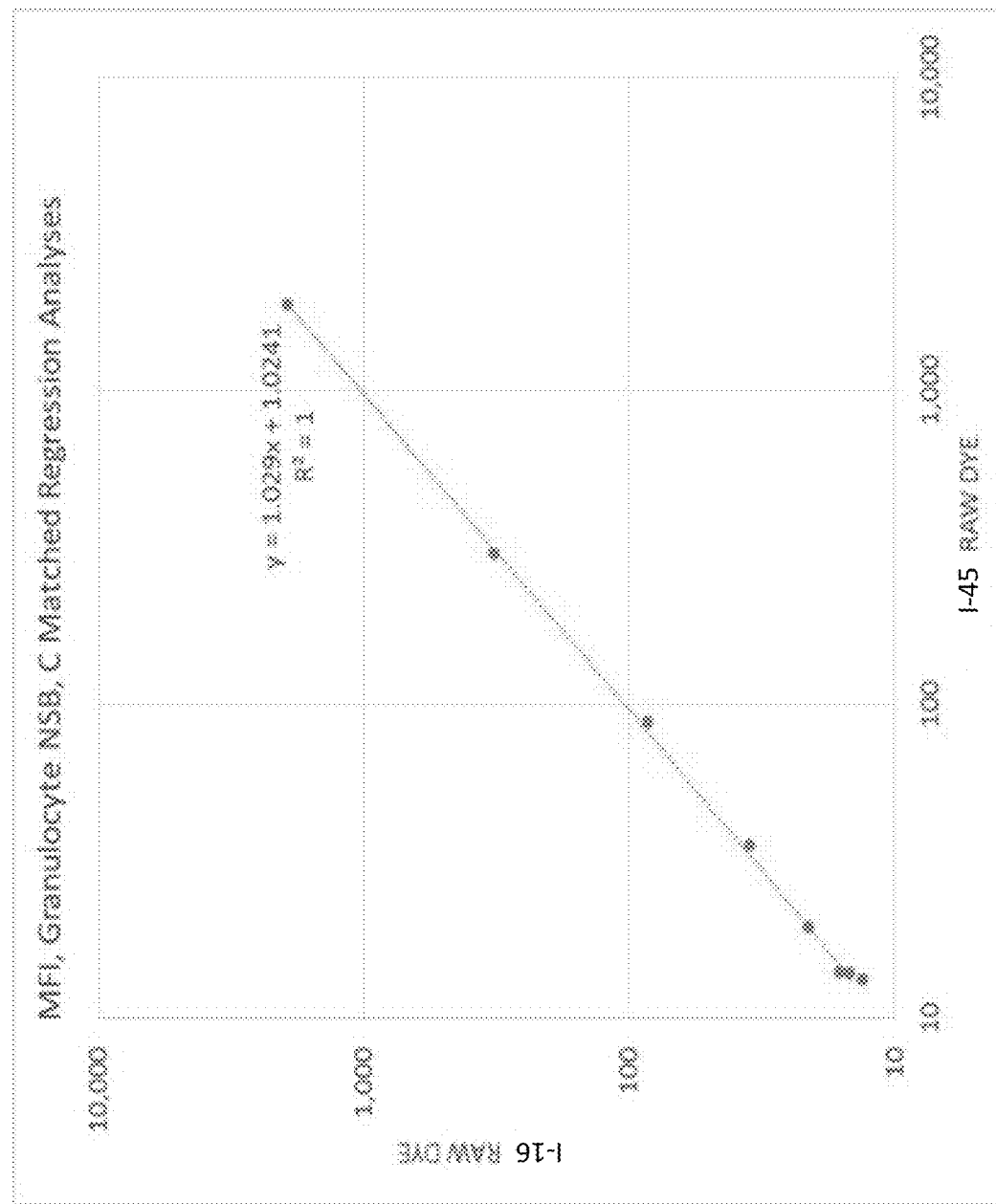
FIG. 21A shows correlations between I-16 and I-45 as determined using regression analysis.
Figure 21B:
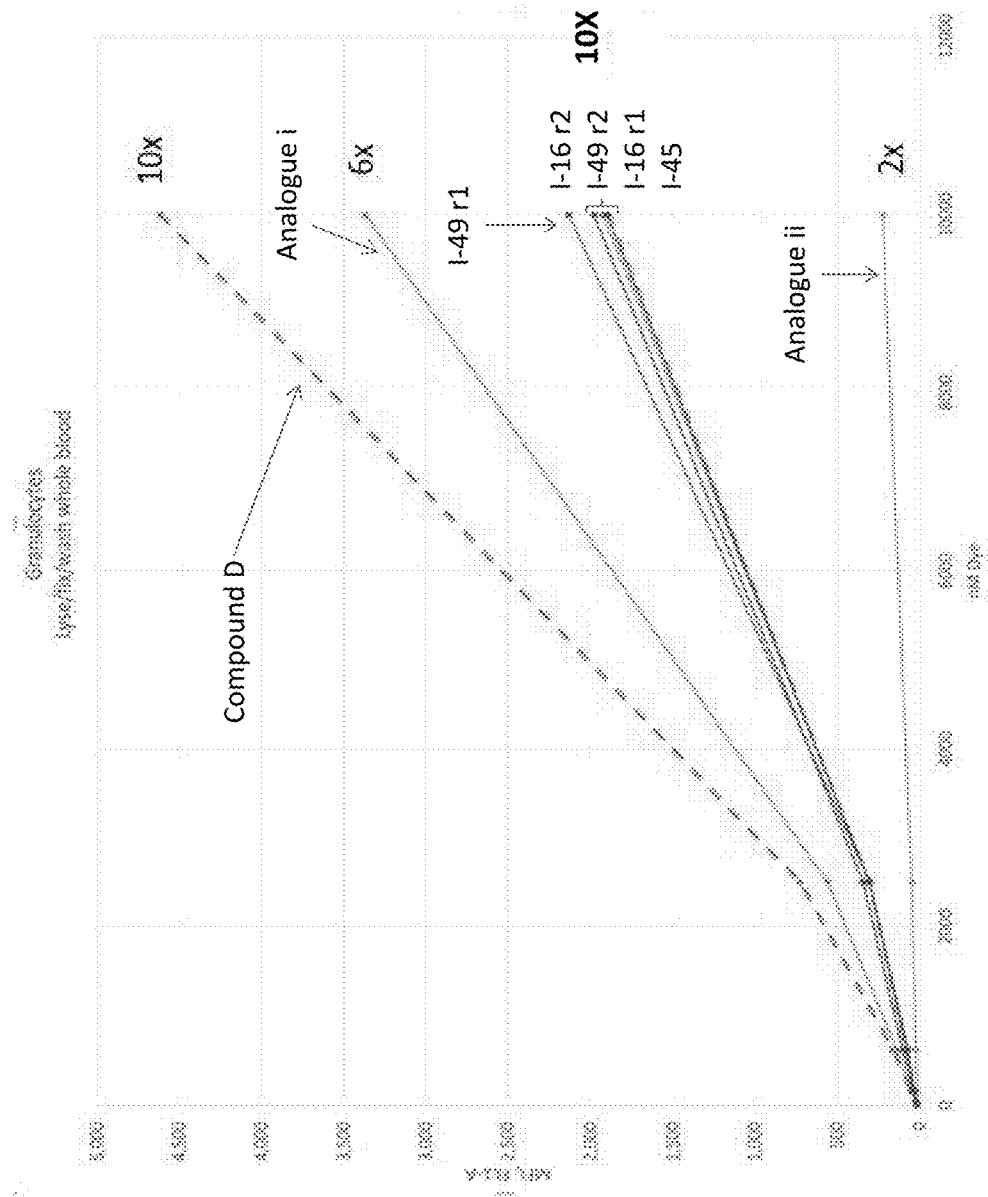
FIG. 21B shows titration curve overlays and compared to references.
Figure 21C:
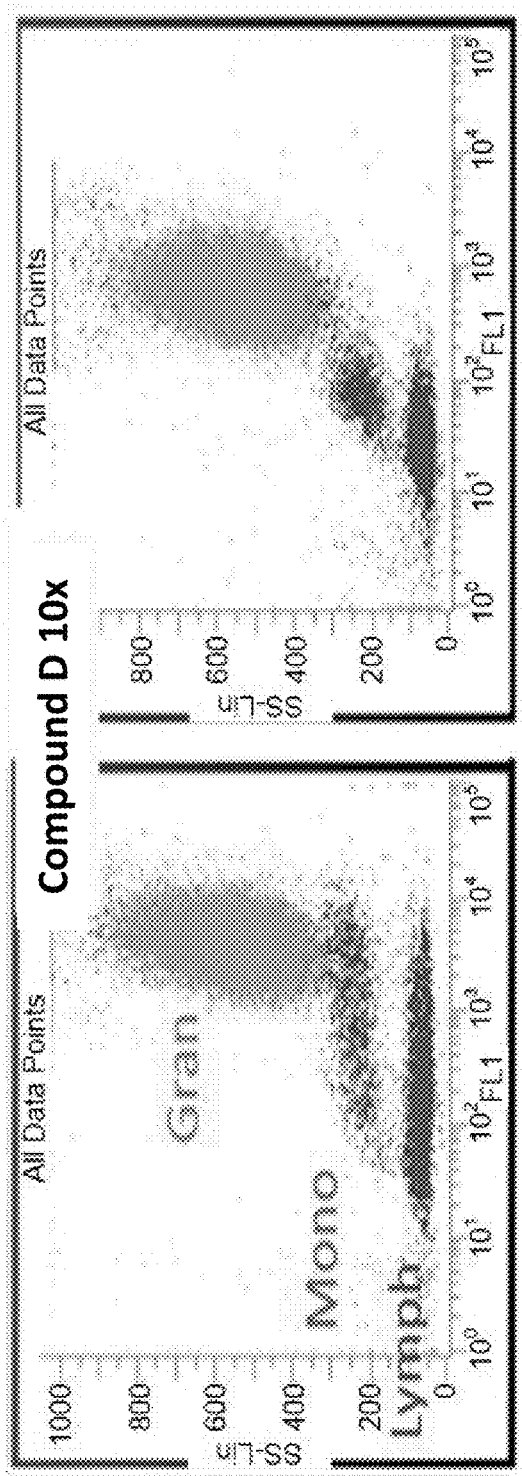
FIG. 21C shows example qualitative data showing background FL and cell morphology comparing Compound D and I-45.
Figure 21C:
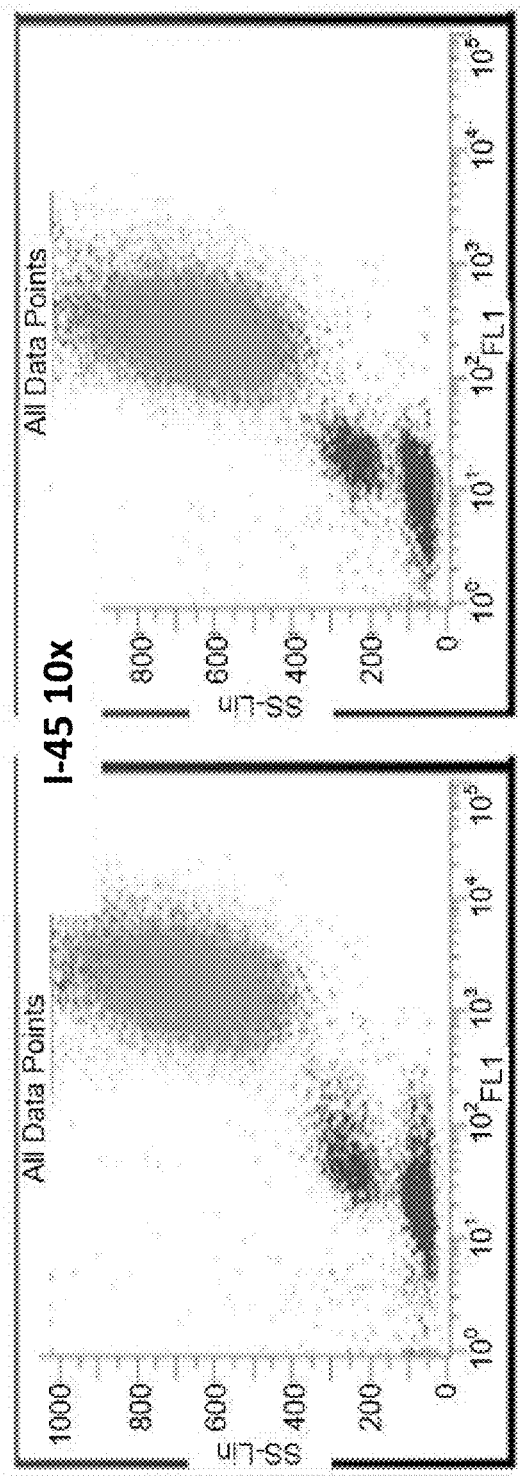

The Relative MFI data was concentration matched and compared by regression analyses to demonstrate level of agreement and or similarity between the raw I-45 and I-16. In this test, I-45 and I-16 are found to have nearly equivalent levels of background. Using the same data from dye screening, the I-45 analogues (I-49 and I-16) overlay each other when examining the entire titration curve and the controls. I-45 analogues fall in between MFIs of controls included for reference were Compound D (10×), and two analogues Compound D (analogues i and ii) having longer alkylene spacer groups. I-49 has slightly higher background than I-16 and I-16 background is very similar to I-45. The 10× fluorophore constructs are dimmer in non-specific binding than the 6×, demonstrating effectiveness of backbone modulation to accommodate additional fluorophores while reducing non-specific binding properties of the 10× molecule. The results are shown in FIGS. 21A-21C. FIG. 21A shows correlations between I-16 and I-45 FIG. 21B shows titration curve overlays and compared to references; and FIG. 21C shows example qualitative data showing background FL and cell morphology comparing Compound D and I-45.

Example 16

Comparison of UCHT1-I-21B and UCHT1-I-16 in Blood Cells that have been Fixed and Stored for 72 Hours Whole blood was drawn from a normal donor into an EDTA stabilized sample tube for transport and short term storage. The blood was treated with lysing agents, either before or after staining with antibodies. The cells were lysed with ACK, 15 mL blood to 35 mL lyse for 15 min at RT, and then washed twice with 50% HBSS and 50% 1% FBS 1×DPBS with 0.02% sodium azide. The cells were re-suspended to 100 μL/test/1×10e6 in donor plasma. Pre-diluted antibodies in 100↓, 1% BSA and 1×DPBS with 0.02% sodium azide were added to 100 μL cells, which were then added to 96 well HTS polypropylene plates (total 200 μL test size). After incubating the cells for 45 min. at RT, the cells were washed twice with 50% HBSS+50% 1% FBS 1×DPBS with 0.02% sodium azide. The cells were then re-suspended in 1% FBS 1×DPBS with 0.02% sodium azide. The cells were washed once more, fixed in 2% paraformaldehyde at 200 μL/well, washed once with 1×DPBS, stored for 72 hours 2-8° C., washed once more using 1×DPBS, and then acquired using 0.1% BSA in 1×DPBS.

Figure 22:
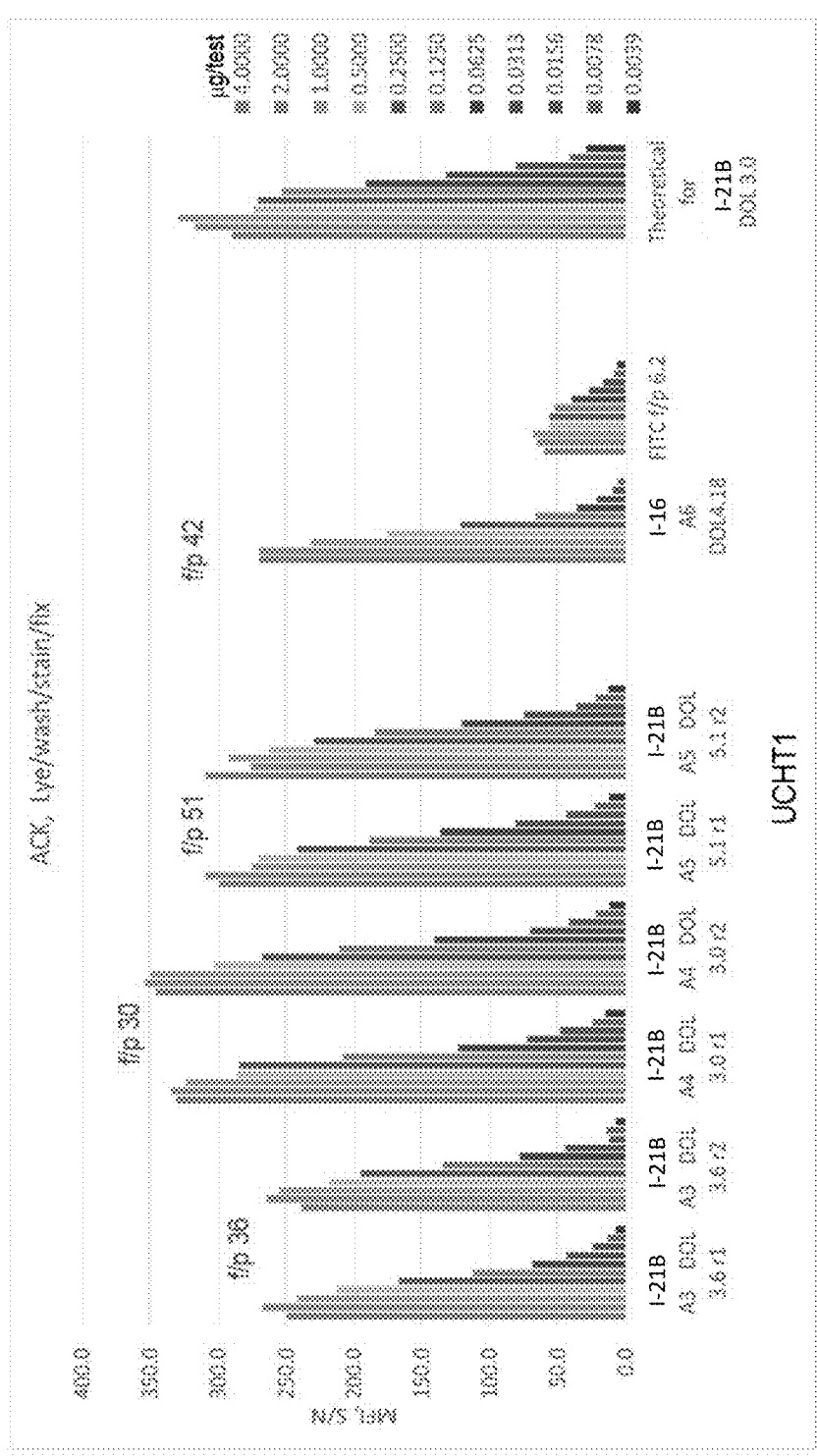
FIG. 22 shows affinity curves, as histograms, with compound emission detected in the FL1-A channel.

The resolution of the conjugates was compared to reference, UCHT1-FITC, and to theoretical brightness for a DOL of 3.0. The new construct UCHT1-I-21B best matches theoretical when DOL is 3.0 in this method, and is seven times brighter that UCHT1-FITC. As shown in FIG. 22, affinity curves, as histograms, are shown with compound emission detected in the FL1-A channel.

Figures 23A, 23B:
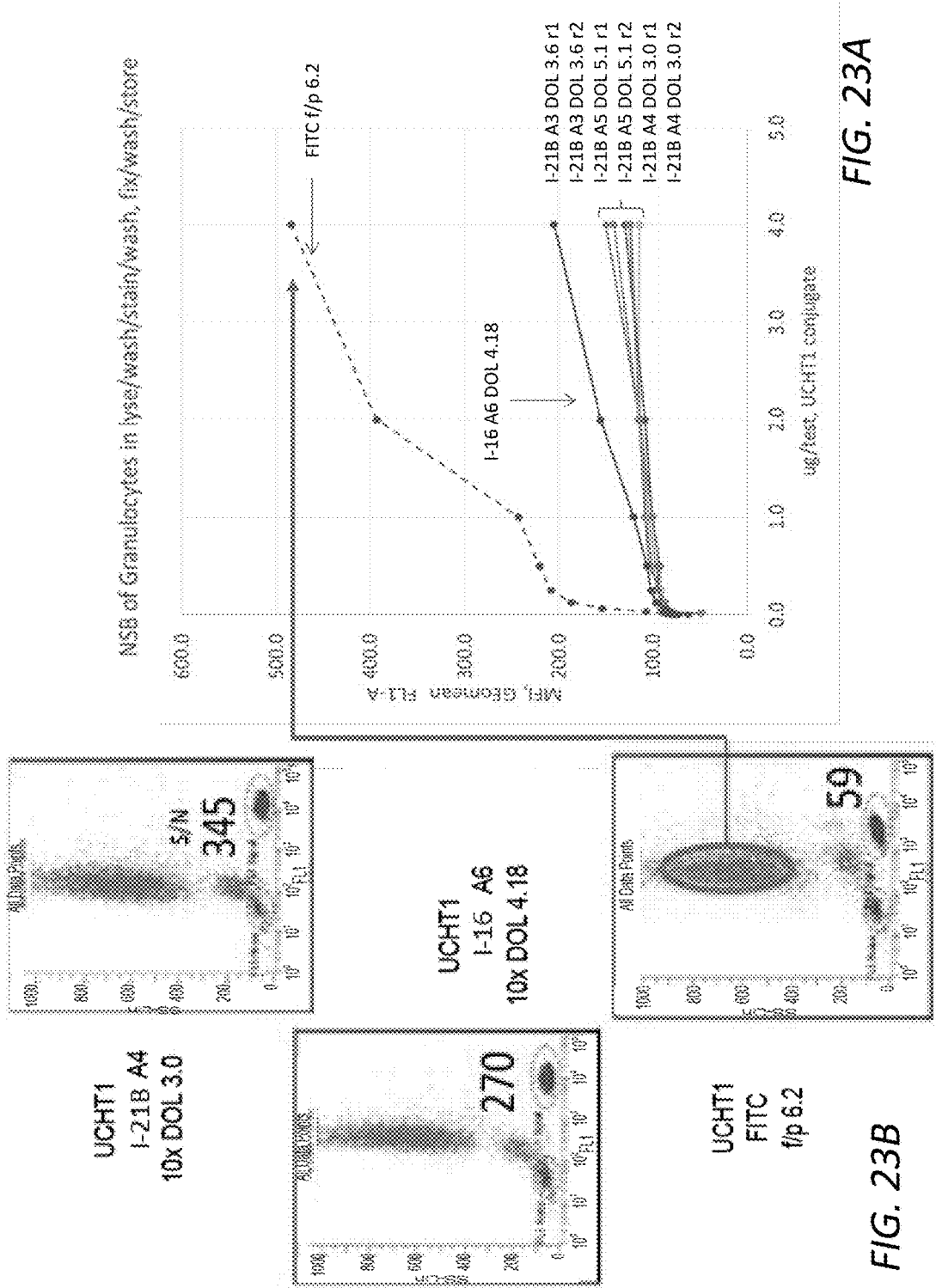
FIG. 23A shows comparisons of fluorescence intensity of off target, non-specific binding of UCHT1-I-21B, UCHT1-I-16, and reference, UCHT1-FITC.
FIG. 23B presents supporting data.
Figure 24:
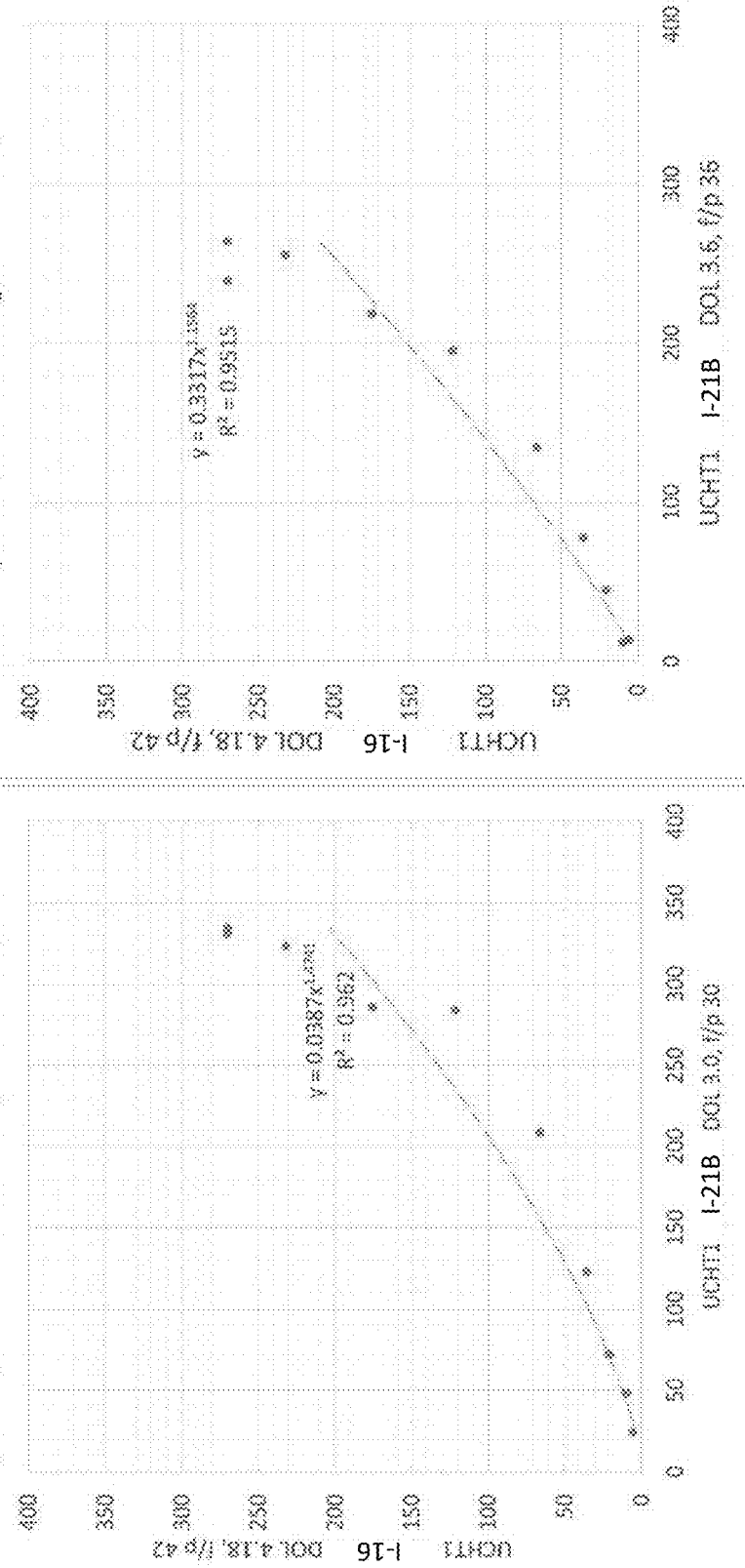
FIG. 24 presents results of a regression analysis that was applied to the data to review correlations and relative affinities.

An assessment of non-specific binding was completed by measuring the fluorescence of granulocytes. FIG. 23 shows comparisons of fluorescence intensity of off target, non-specific binding of UCHT1-I-21B, UCHT1-I-16, and reference, UCHT1-FITC. All fractions and replicates of UCHT1-I-21B show less background than other constructs and the FITC reference included in the test. Regression analysis was applied to the data to review correlations and relative affinities, as shown in FIG. 24, and it was determined that UCHT1-I-21B does not have a linear relationship with UCHT1-I-16.

Example 17

UCHT1 I-21B Using the Jurkat Cell Model and a Simple Two Point Titer

Similar to Example 16 a test of UCHT1 I-21B was performed in a simple two point titer of 2.0 and 0.125 micrograms per test of antibody. Jurkat cells were cultured according to instructions provided by ATCC, harvested live or heat stressed, washed 2-3x, and then stained with conjugate antibodies. Staining was performed when cells were applied to pre-diluted conjugated antibodies, incubated, washed, and then acquired by flow cytometry.

Figure 25:
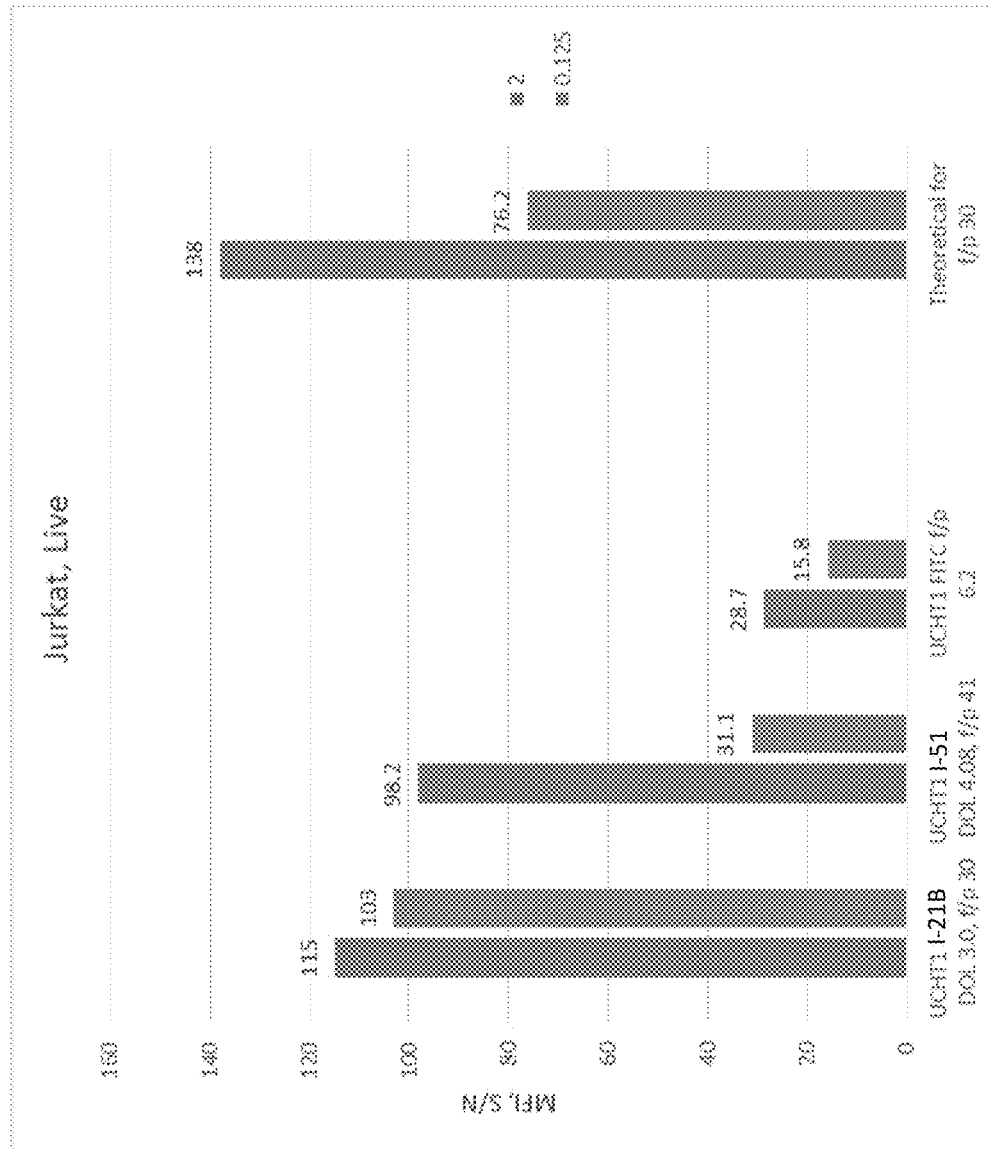
FIG. 25, shows signal to noise data for UCHT1-I-21B, UCHT1-I-51, and UCHT1-FITC.

As shown in FIG. 25, UCHT1-I-21B demonstrates higher affinity at low concentration compared to UCHT1-I-51, as expected. The actual signal to noise exceeds theoretical at a sub saturation C of 0.125 micrograms per test and out performs UCHT1-I-51.

Example 18

Comparison of UCHT1 Compound G and UCHT1 I-51 in a Plasma Interference Study Using PBMC PBMC and autologous plasma were previously isolated from peripheral whole blood, and then frozen in freezing media. Cells were thawed, briefly rested, washed two or three times, and then stained with conjugate antibodies as if freshly isolated from whole blood, with autologous plasma, or HBSS present during antibody staining.

Figure 26A:
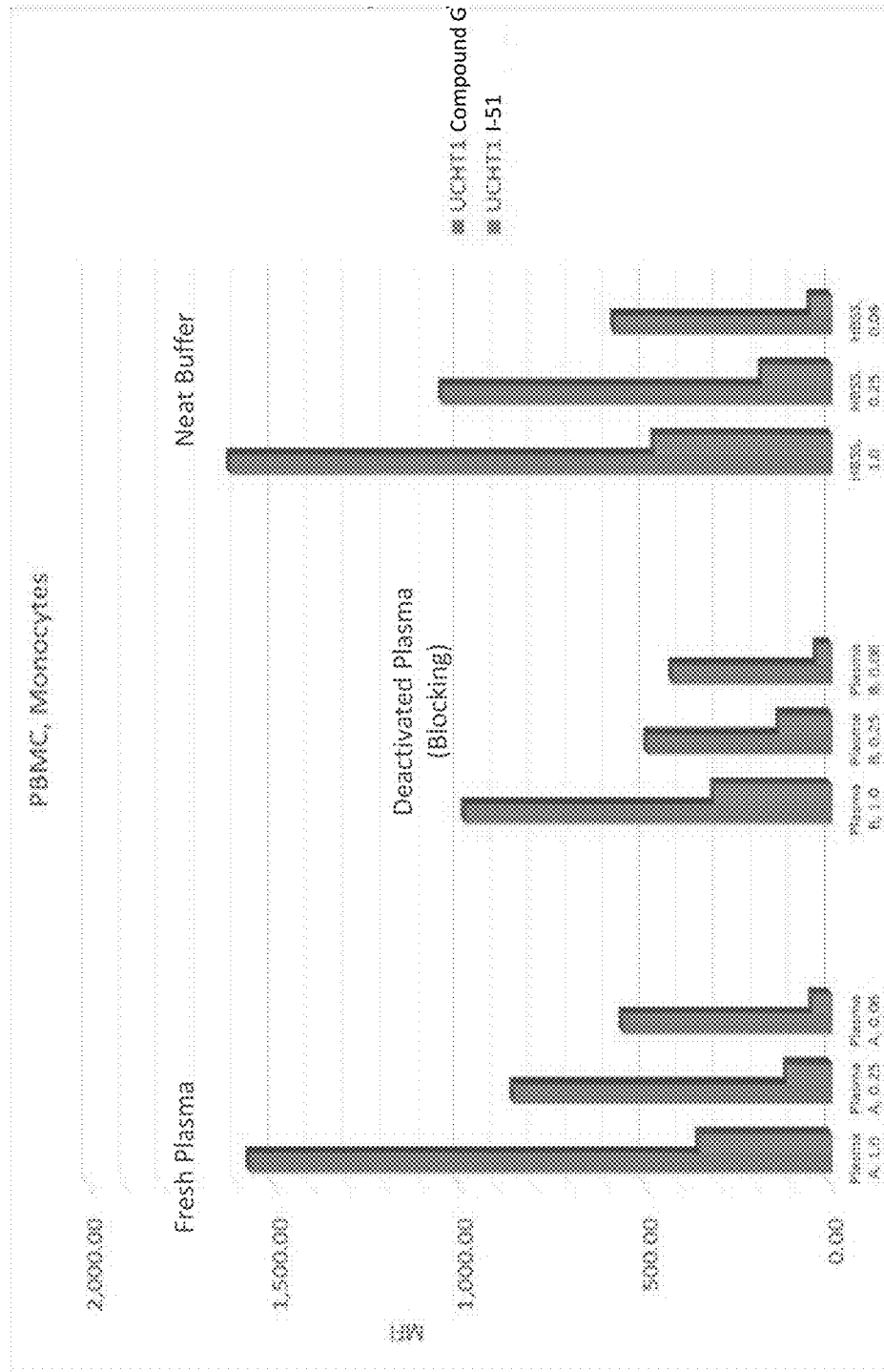
FIGS. 26A and 26B provide data comparing UCHT1 Compound G AND UCHT1 I-51 in a plasma interference study using PBMC.
Figure 26B:
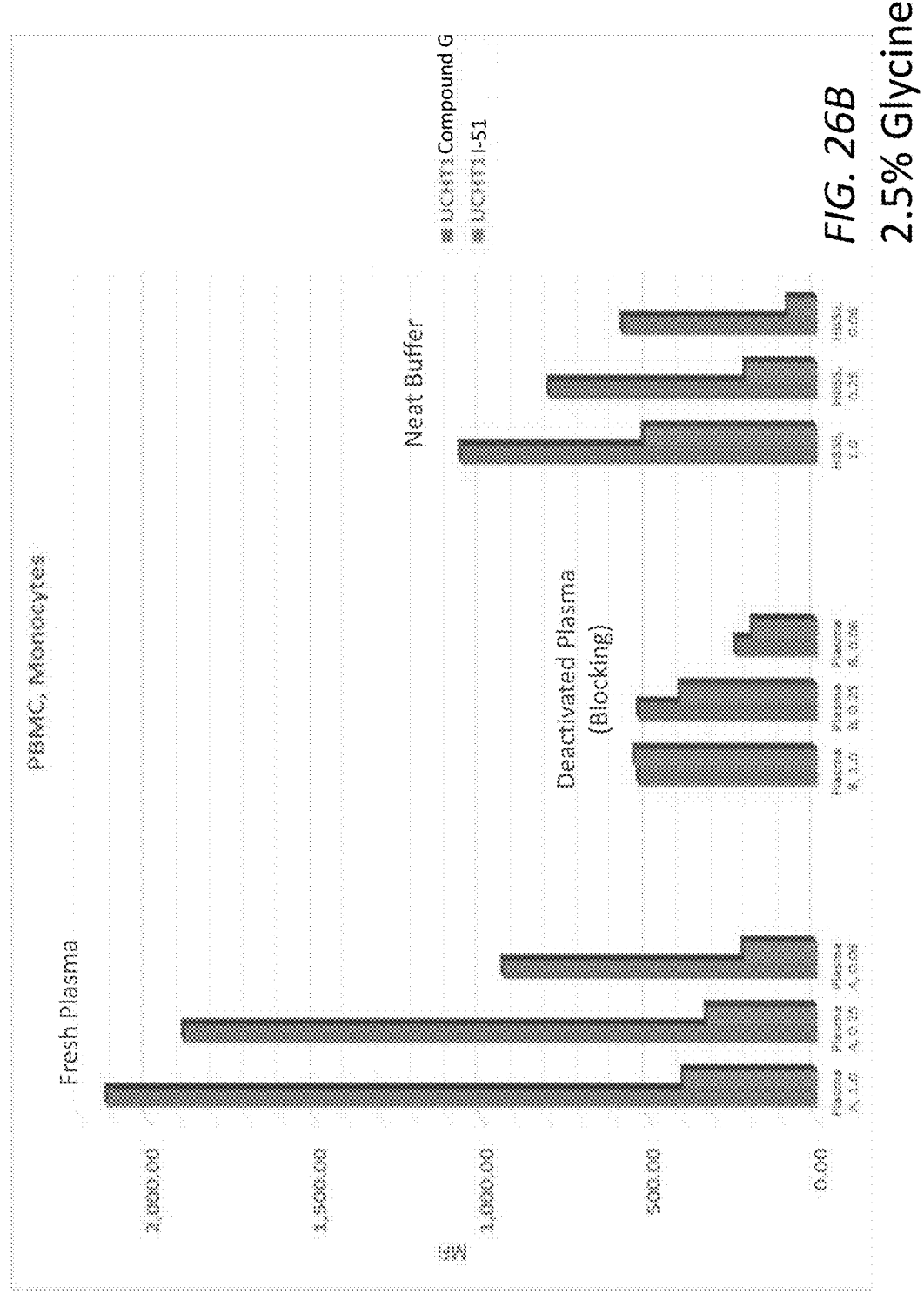

UCHT1-Compound G interacted with monocytes to form fluorescent events in the presence of activated and deactivated donor plasma, and additions of 2.5% glycine. FIG. 26A shows data resulting from the addition of 0% glycine, and FIG. 26B shows data resulting from the addition of 2.5% glycine. The Zwitterion amino acid glycine plays a role in immunoassays as surrogate affinity for, amide binding with, or blocking by, natural poly-amines, thus exaggerating or blocking the effects of other reagents in the staining system of live cells. Plasma re-introduced to PBMC is either (1) activating, with compliment, platelets present at normal levels, or (2) deactivated (both plasma compliment and other factors) by heat, filtration, and centrifugation to remove most platelets. The deactivated plasma functions more as a blocking agent, while the activating plasma is expected to have high interference.

The study mimics a range of effects possible in whole blood when blood is mobilized, plasma is present, residual, diluted, or washed away. Compound C and I-45 show distinct differences in behavior as expected, supporting a decrease in background binding and distinct improvement in activity by structural modification to I-45. Generally, it is observed that UCHT1-I-51 background is limited in comparison to Compound G, while glycine when present slightly enhances the background staining of I-51 and suppresses the background of UCHT1-Compound G, particularly in the deactivated plasma and neat control. Overall, the UCHT1-Compound G has higher monocyte background.

Example 19

Preparation of Phosphoramidites and Compounds

Exemplary compounds were prepared using standard solid-phase oligonucleotide synthesis protocols and a fluorescein-containing phosphoramidite having the following structure:

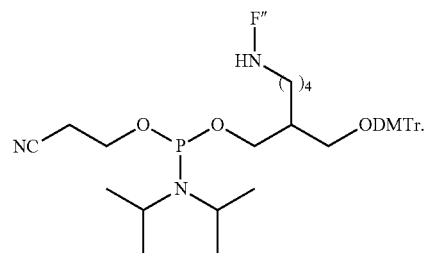

which was purchased from ChemGenes (Cat.# CLP-9780).

Exemplary linkers ($L^4$) were included in the compounds by coupling with a phosphoramidite having the following structure:

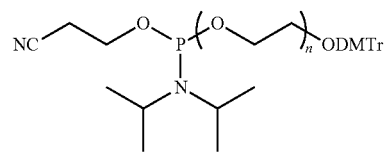

which is also commercially available.

Other exemplary compounds were prepared using a phosphoramidite prepared according to the following scheme:

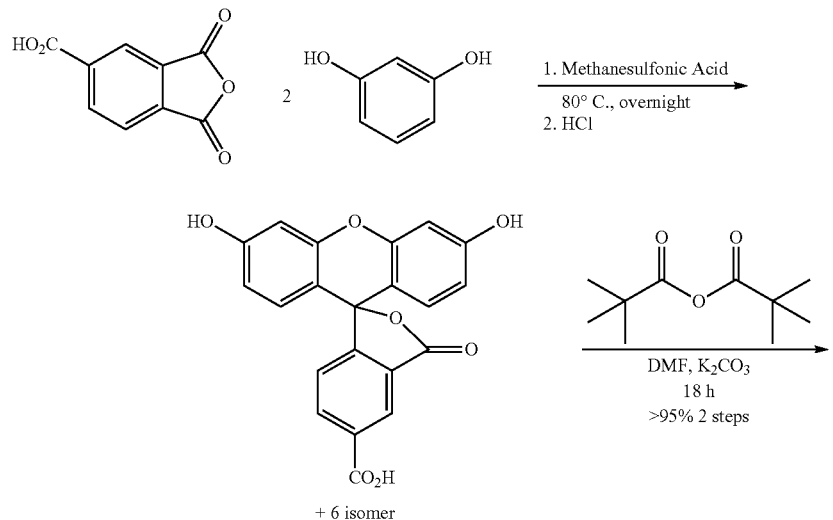

+ 6 isomer

121 122
-continued
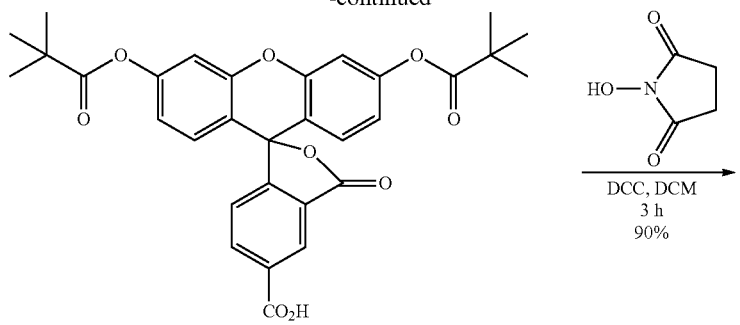
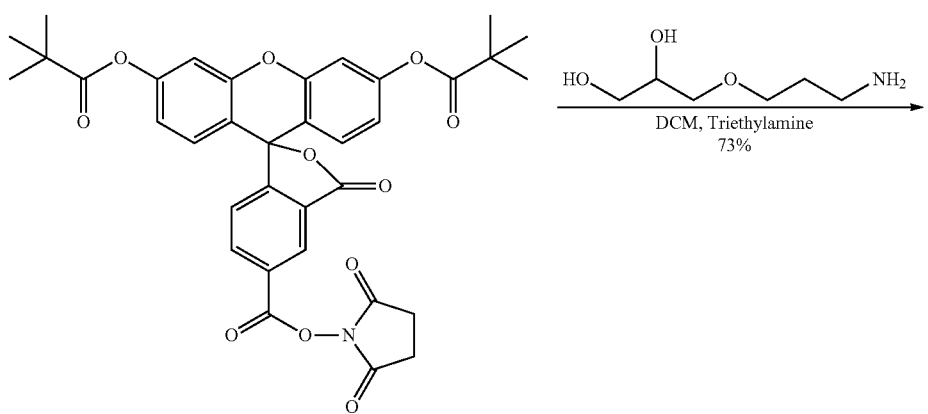
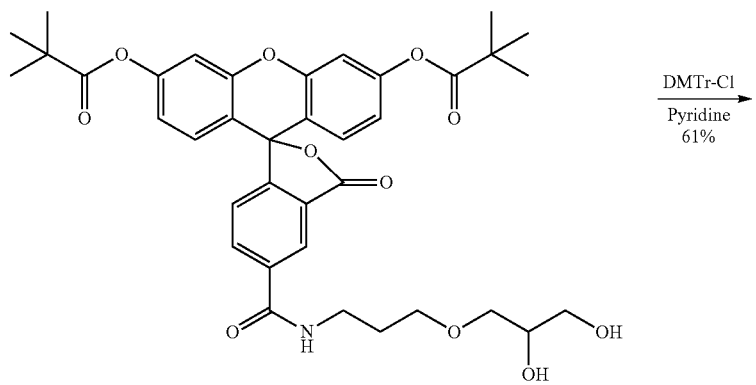
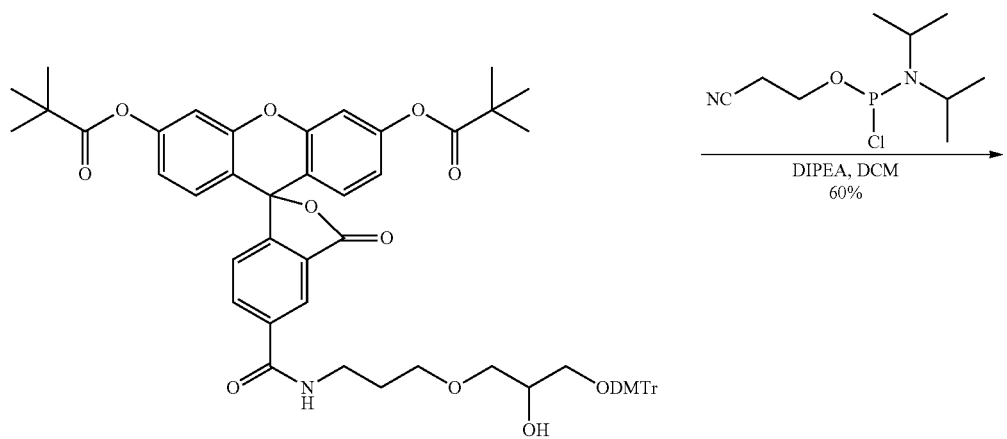

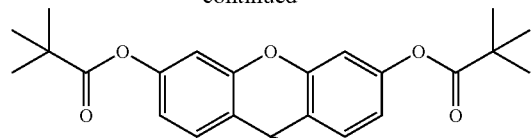

Final Deprotection produces the desired F'" moiety. Other commercially available phosphoramidite reagents were employed as appropriate to install the various portions of the compounds. Q moieties having the following structure:

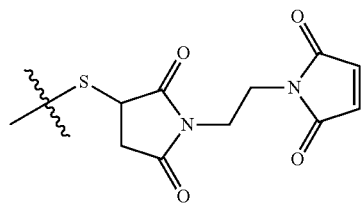 [SMILES: *SC1CC(=O)N(CCN2C(=O)C=CC2=O)C1=O]

were installed by reaction of:

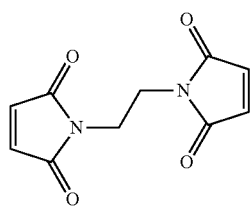 [SMILES: O=C1C=CC(=O)N1CCN1C(=O)C=CC1=O]

with a free sulfhydryl. Other Q moieties are installed in an analogous manner according to knowledge of one of ordinary skill in the art.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the following structure (I):

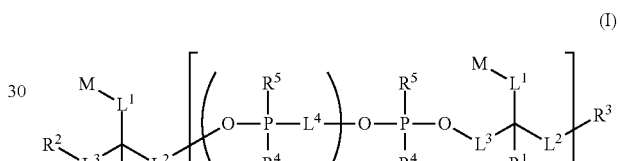

or a stereoisomer, salt or tautomer thereof, wherein:

M is, at each occurrence, independently a fluorescent dye;

$L^1$ is at each occurrence, independently either: i) an optional alkylene, alkenylene, alkynylene, heteroalkylene, heteroalkenylene, heteroalkynylene or heteroatomic linker; or ii) a linker comprising a functional group capable of formation by reaction of two complementary reactive groups;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently a polyethylene oxide linker;

$R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q, or a protected form thereof, or L';

$R^4$ is, at each occurrence, independently OH, SH, O⁻, S⁻, OR$_d$ or SR$_d$;

$R^5$ is, at each occurrence, independently oxo, thioxo or absent;

$R_a$ is O or S;

$R_b$ is OH, SH, O⁻, S⁻, OR$_d$ or SR$_d$;

$R_c$ is OH, SH, O⁻, S⁻, OR$_d$, OL', SR$_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, independently an integer of zero or greater, provided that at least one occurrence of m is an integer of one or greater, such that the compound includes at least one $L^4$; and n is an integer of one or greater.

2. The compound of claim 1, wherein the compound has the following structure (IA):

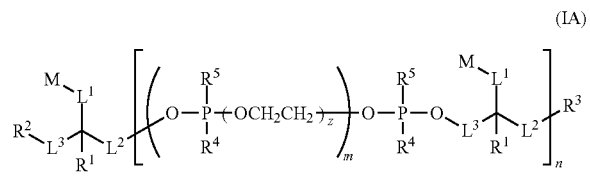
(IA)

wherein z is an integer from 2 to 100.

3. The compound of claim 2, wherein z is an integer from 3 to 6.

4. The compound of claim 1, wherein $L^1$ has one of the following structures:

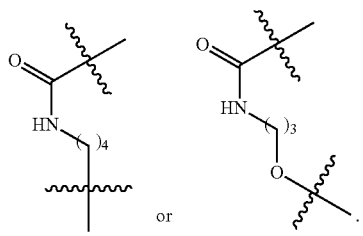

5. The compound of claim 1, wherein the compound has the following structure (IB):

wherein:

$x^1$, $x^2$, $x^3$ and $x^4$ are, at each occurrence, independently an integer from 0 to 6; and z is an integer from 2 to 100.

6. The compound of claim 5, wherein $x^1$ and $x^3$ are each 0 at each occurrence, and $x^2$ and $x^4$ are each 1 at each occurrence.

7. The compound of claim 5, wherein $x^1$, $x^2$, $x^3$ and $x^4$ are each 1 at each occurrence.

8. The compound of claim 1, wherein $R^4$ is, at each occurrence, independently OH, O⁻ or $OR_d$, and $R^5$ is, at each occurrence, oxo.

9. The compound of claim 1, wherein $R^1$ is, at each occurrence, H.

10. The compound of claim 1, wherein $R^2$ and $R^3$ are each independently —OP(=$R_a$)($R_b$)$R_c$.

11. The compound of claim 10, wherein $R_c$ is OL'.

12. The compound of claim 11, wherein L' is a heteroalkylene linker to: Q, a targeting moiety, an analyte molecule, a solid support, a solid support residue, a nucleoside or a further compound of structure (I).

13. The compound of claim 12, wherein L' comprises an alkylene oxide or phosphodiester moiety, or combinations thereof.

14. The compound of claim 13, wherein L' has the following structure:

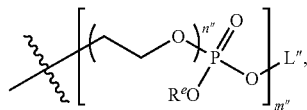

wherein:

m" and n" are independently an integer from 1 to 10;

$R^e$ is H, an electron pair or a counter ion;

L" is $R^e$ or a direct bond or linkage to: Q, a targeting moiety, an analyte molecule, a solid support, a solid support residue, a nucleoside or a further compound of structure (I).

15. The compound of claim 12, wherein the targeting moiety is an antibody or cell surface receptor antagonist.

16. The compound of claim 10, wherein $R^2$ or $R^3$ has one of the following structures:

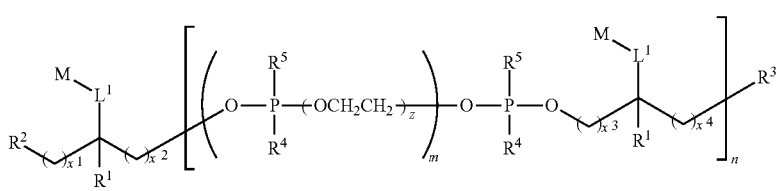
(IB)

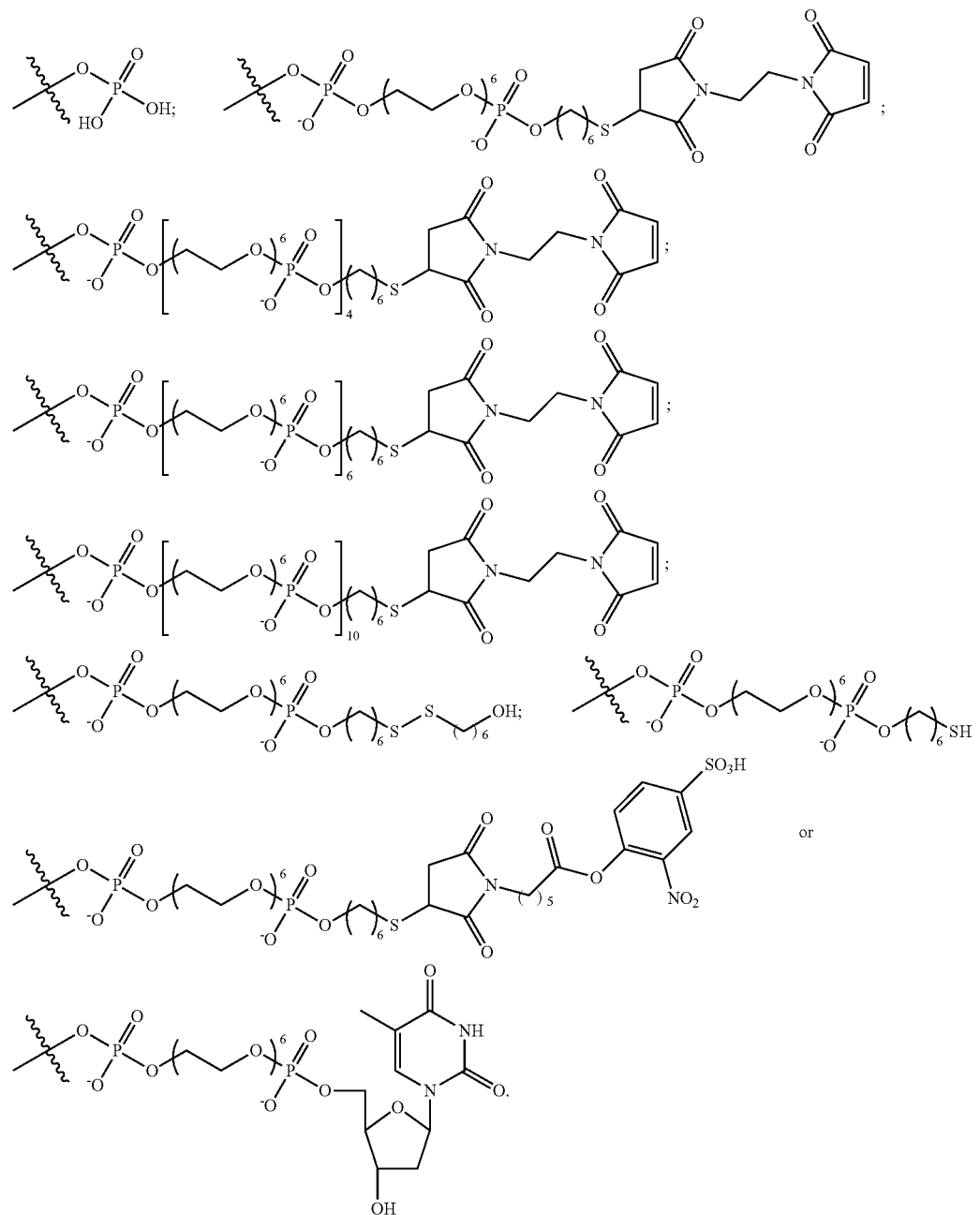

17. The compound of claim 1, wherein Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group.

18. The compound of claim 17, wherein O comprises a maleimide functional group.

19. The compound of claim 1, wherein Q has one of the following structures:

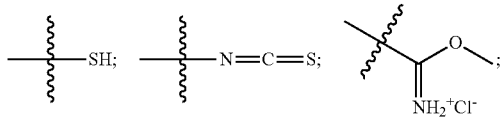

-continued

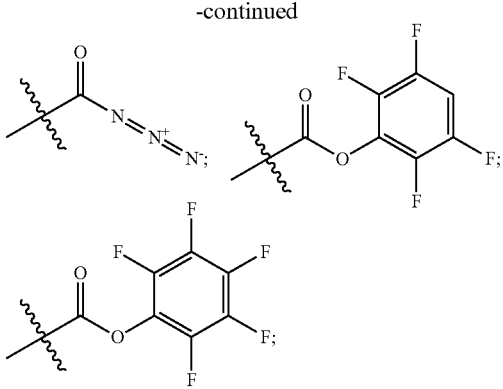

-continued

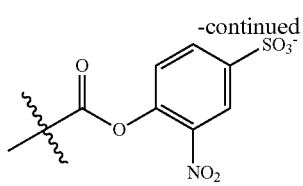

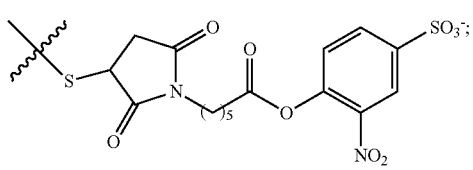

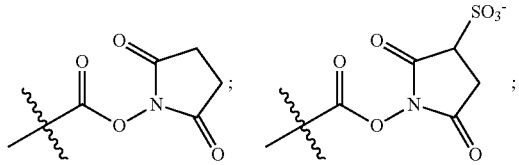

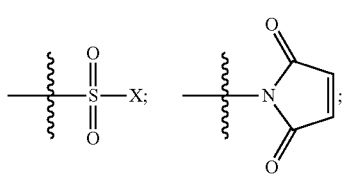

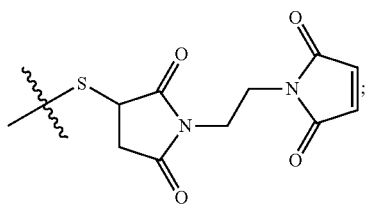

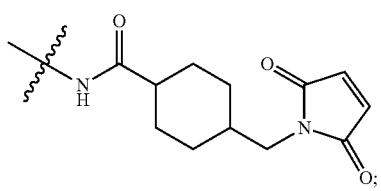

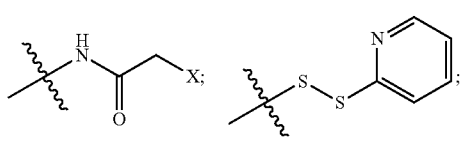

-continued

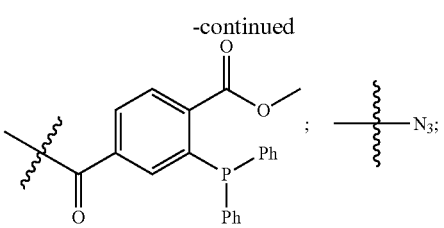

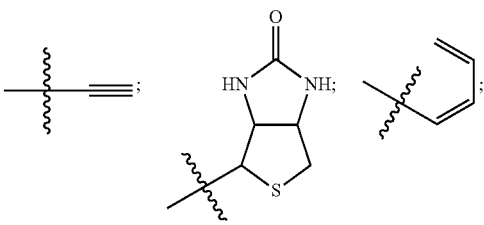

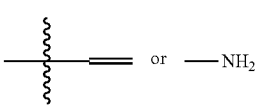

wherein each X is independently a halogen.

20. The compound of claim 1, wherein m is, at each occurrence, independently an integer from 1 to 10.

21. The compound of claim 1, wherein m is, at each occurrence, independently an integer from 1 to 5.

22. The compound of claim 1, wherein n is an integer from 1 to 10.

23. The compound of claim 1, wherein M is, at each occurrence, independently pyrene, perylene, perylene monoimide or 6-FAM or derivative thereof.

24. The compound of claim 1, wherein M, at each occurrence, independently has one of the following structures:

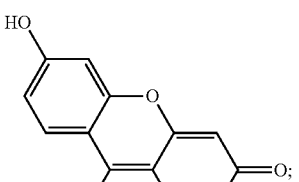

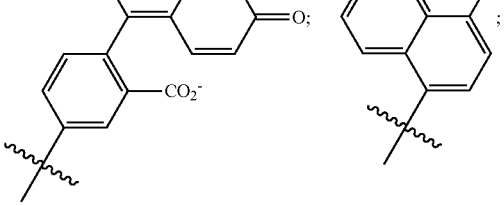

131
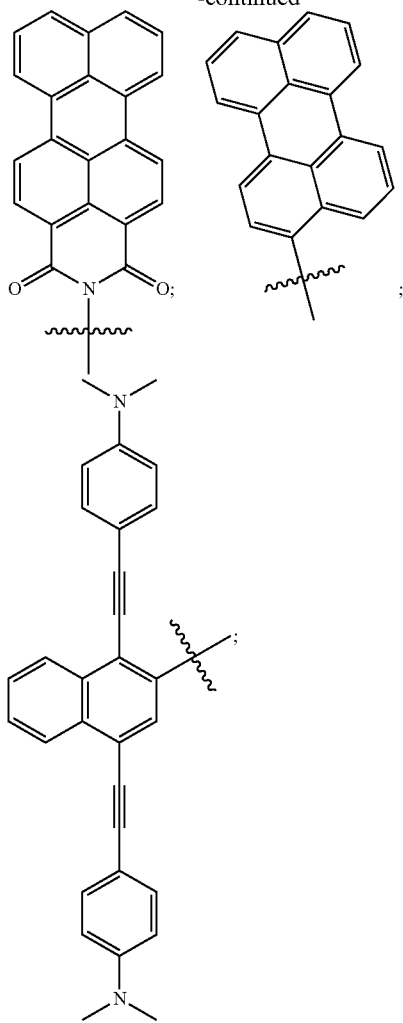
132
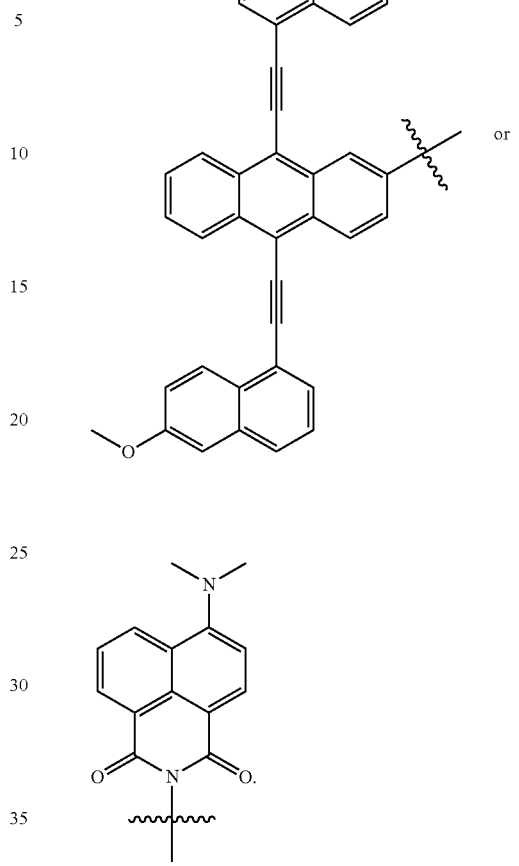
25. The compound of claim 1, wherein the compound has one of the following structures I-1 through I-60:
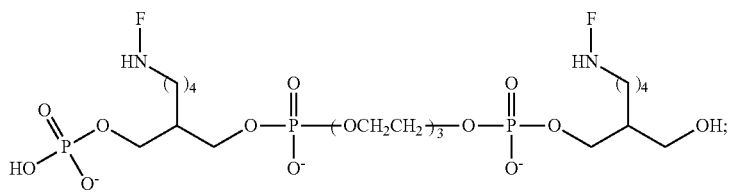
I-1
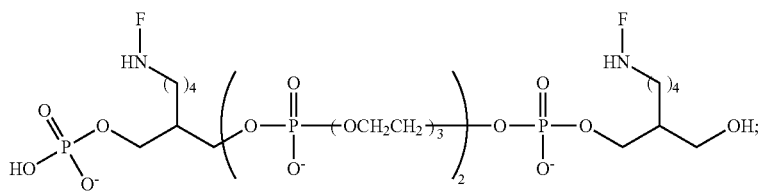
I-2
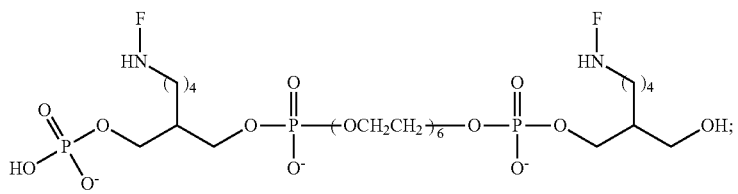
I-3

-continued
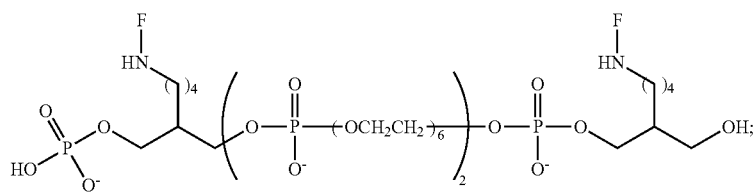
I-4
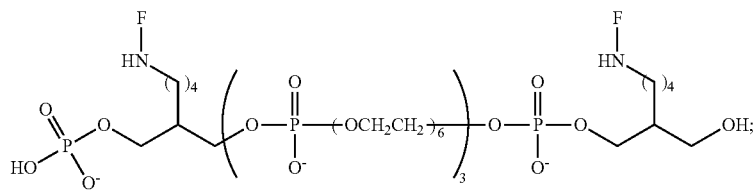
I-5
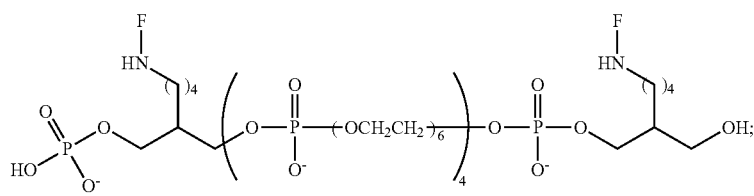
I-6
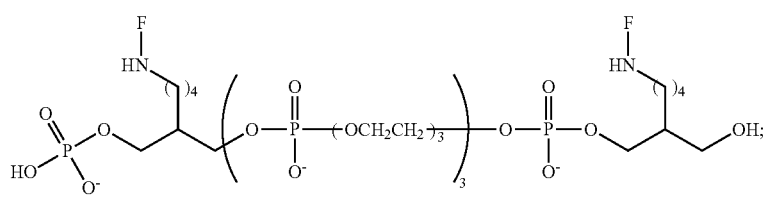
I-7
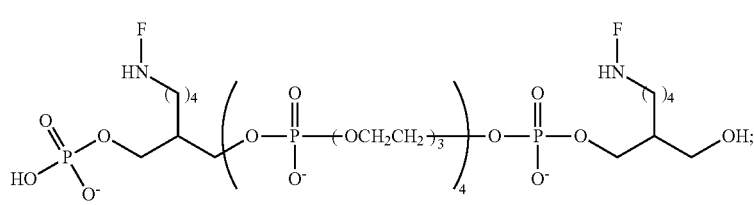
I-8
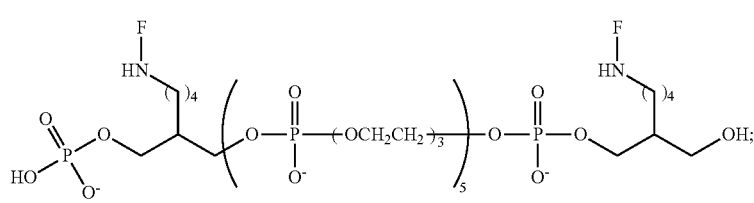
I-9
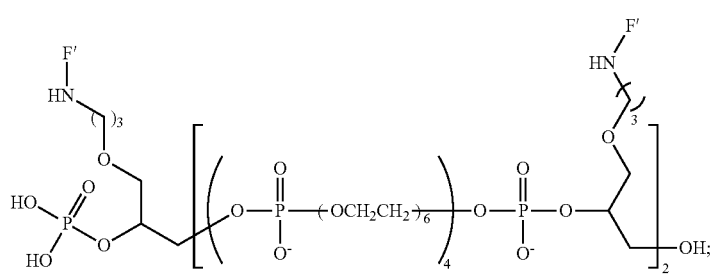
I-10

I-11
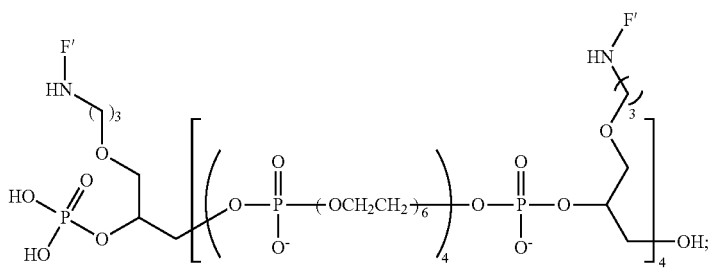
I-12
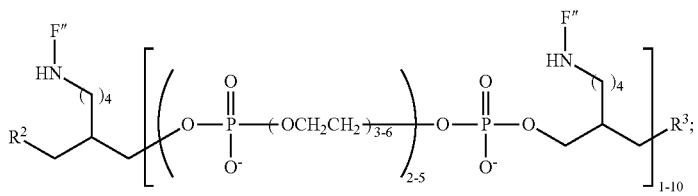
I-13
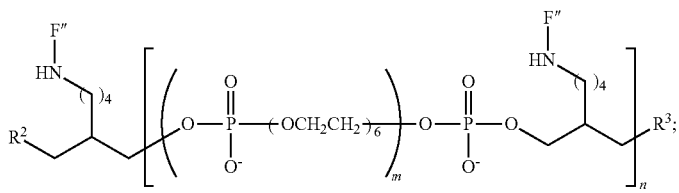
I-14
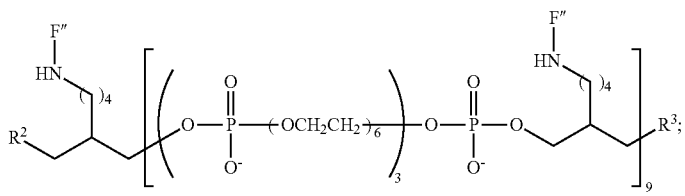
I-15
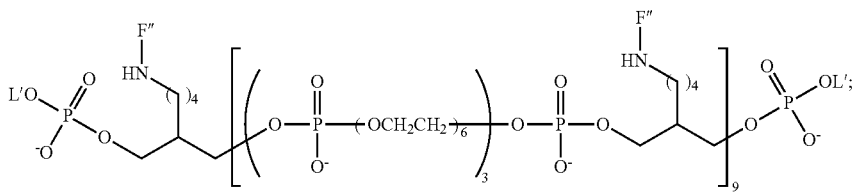
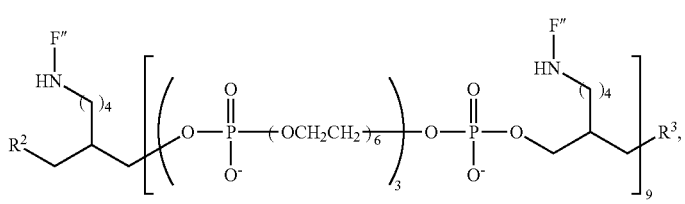
wherein:
I-16
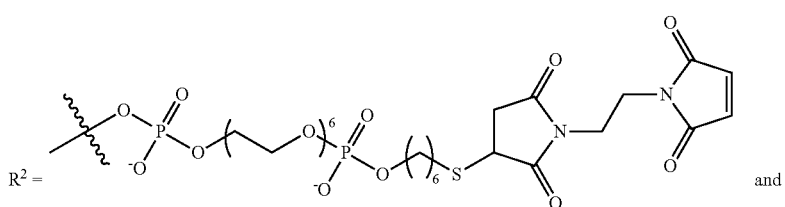 and
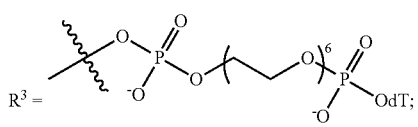

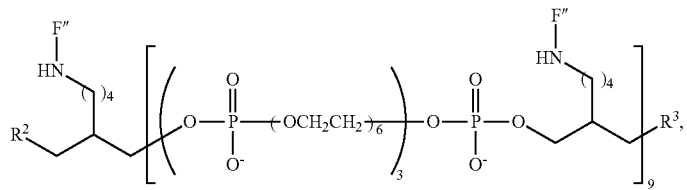
wherein:
I-17
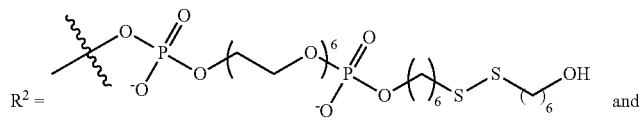
R² = 
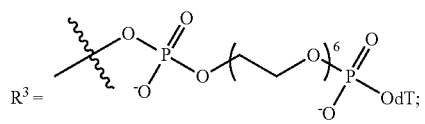
R³ = 
and
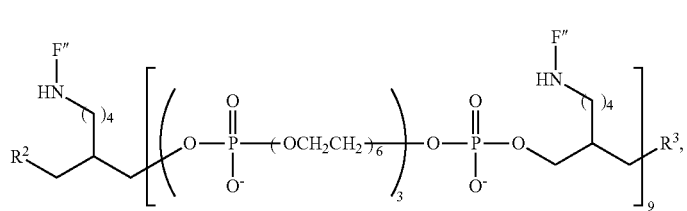
I-18
wherein:
R² = ... SH  and  R³ = ... OdT;
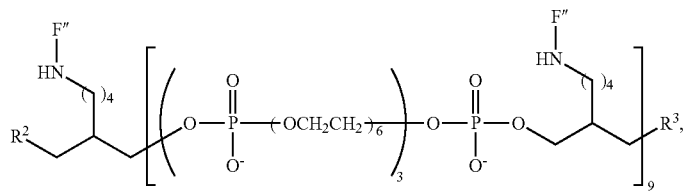
wherein:
I-19
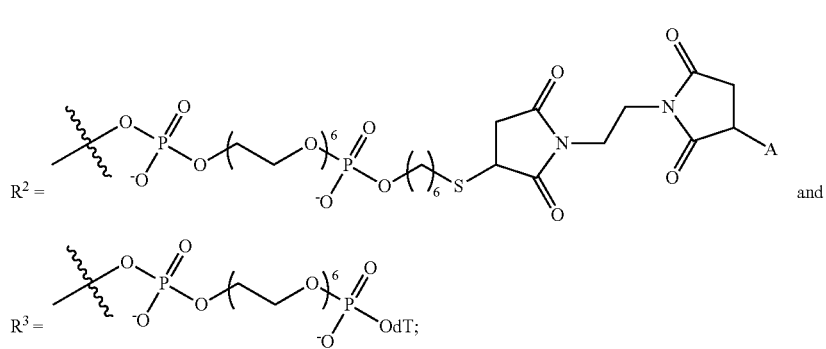
R² = ... and
R³ = ... OdT;

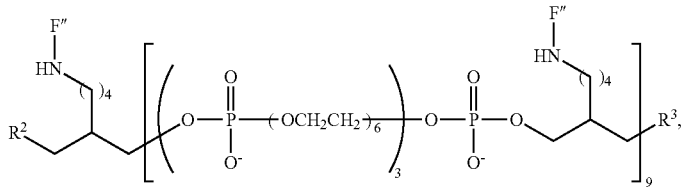
wherein:
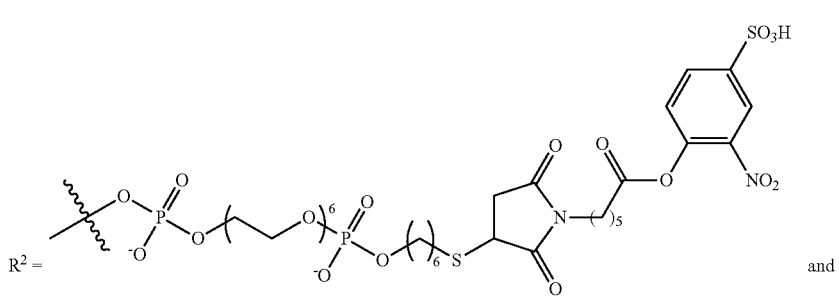
I-20
and
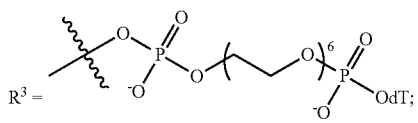
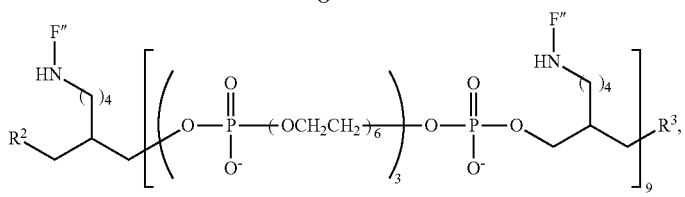
wherein:
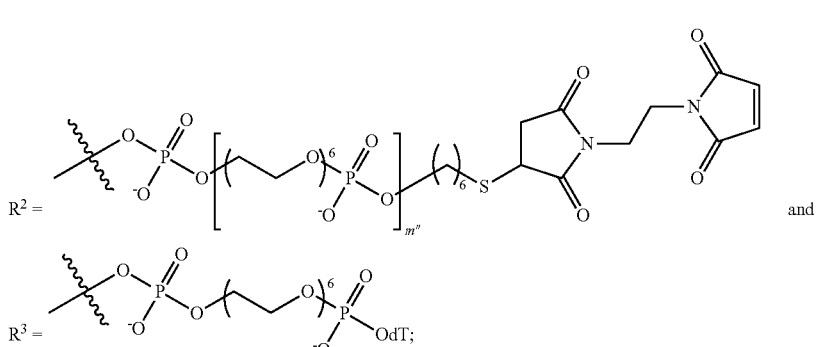
I-21
and
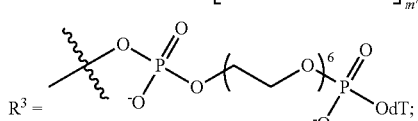
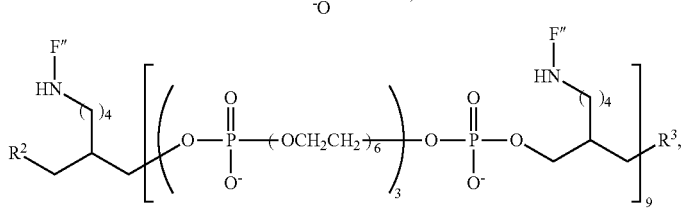
wherein:
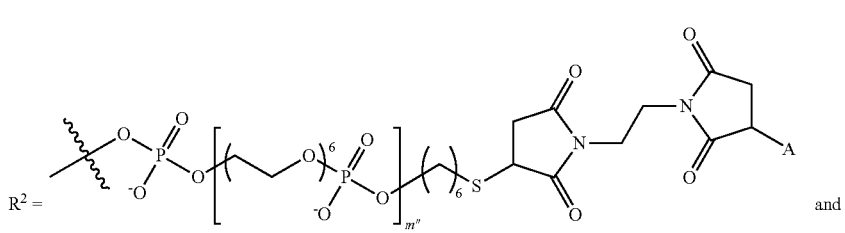
I-22
and

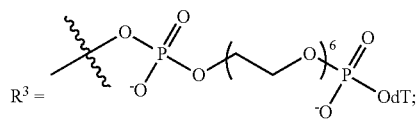
I-23
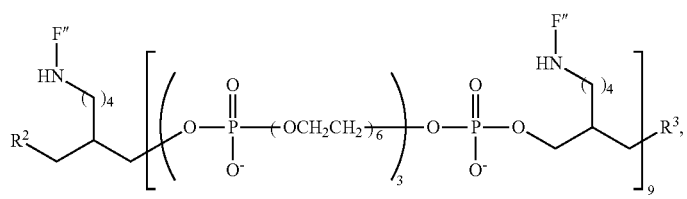
wherein:
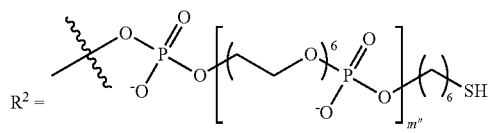
I-24
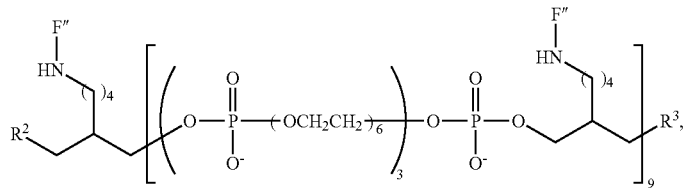
wherein:
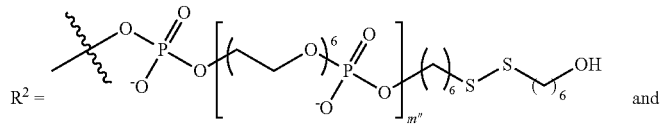
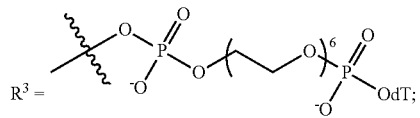
I-25
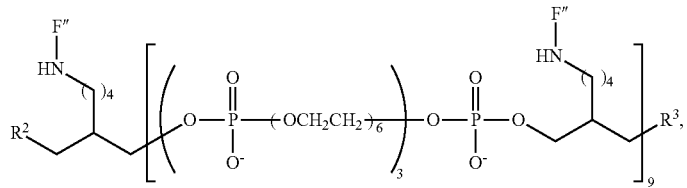
wherein:
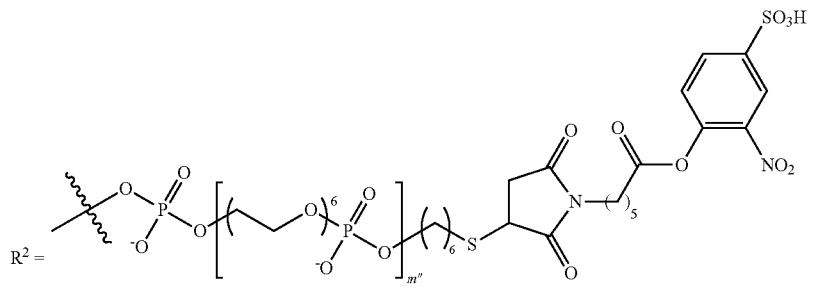
and
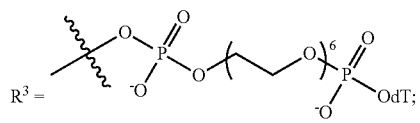

-continued
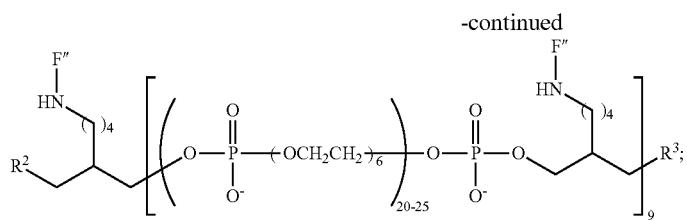
wherein:
I-26
$R^2 =$ 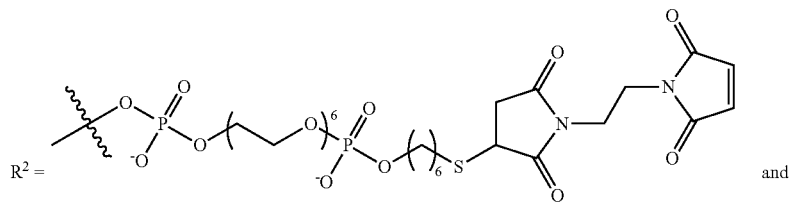 and
$R^3 =$ 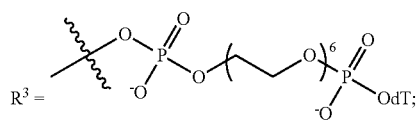
I-27
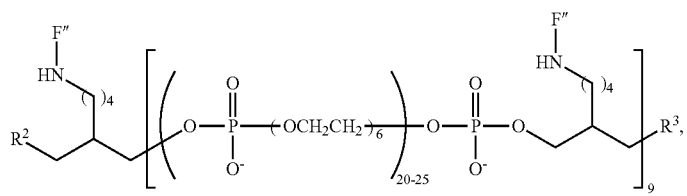
wherein:
$R^2 =$ 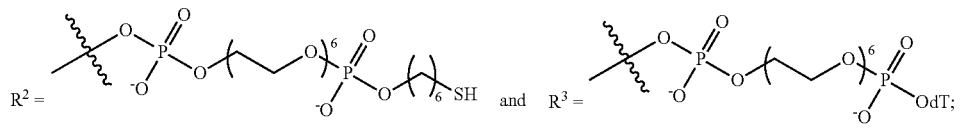 and $R^3 =$ 
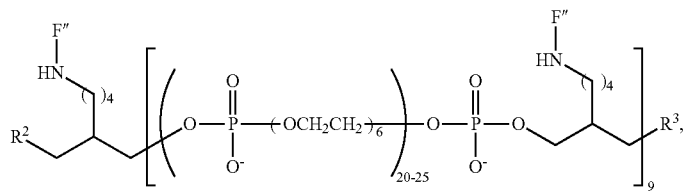
wherein:
I-28
$R^2 =$ 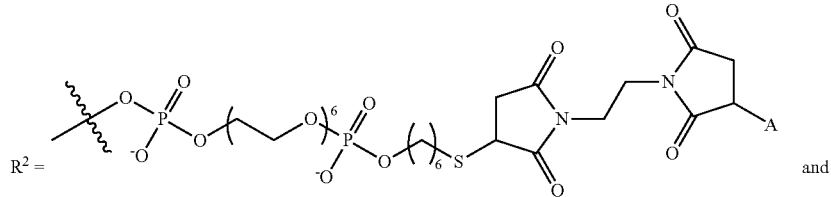 and
$R^3 =$ 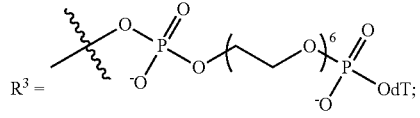

-continued
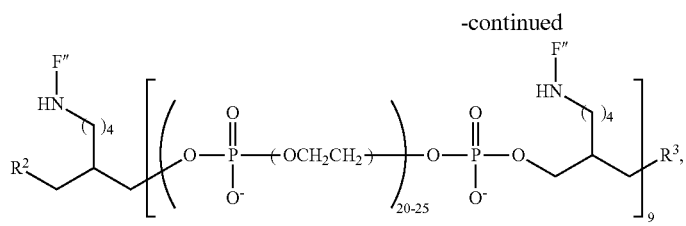
wherein:
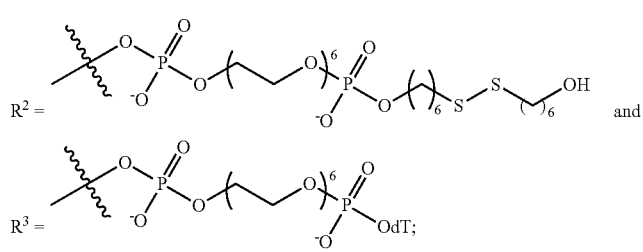
I-29
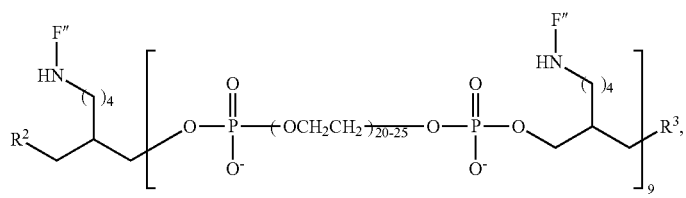
wherein:
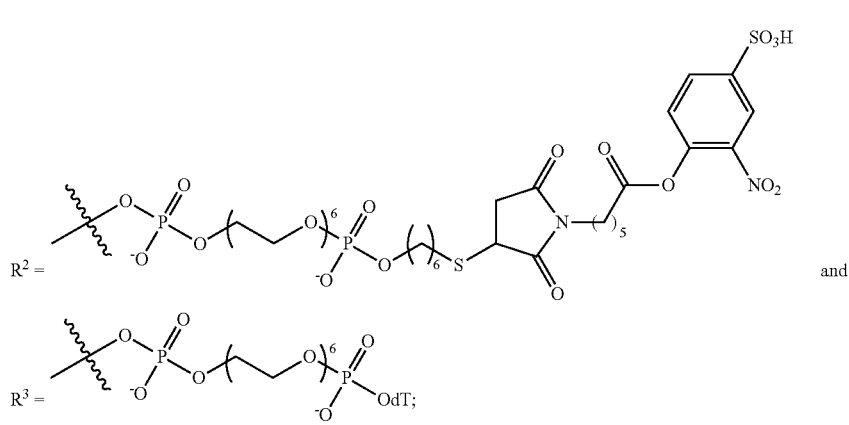
I-30
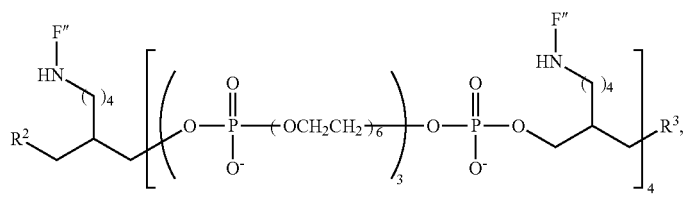
wherein:
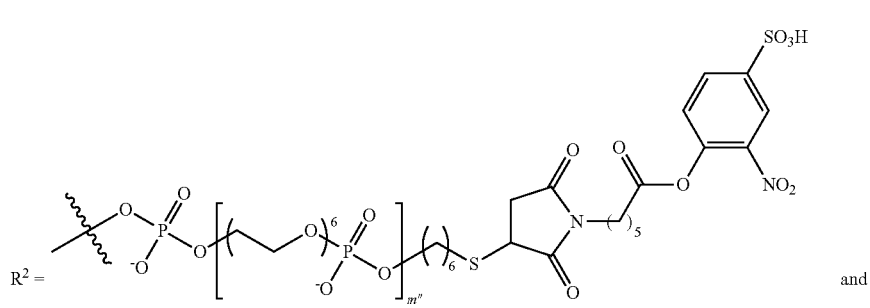
I-31

-continued
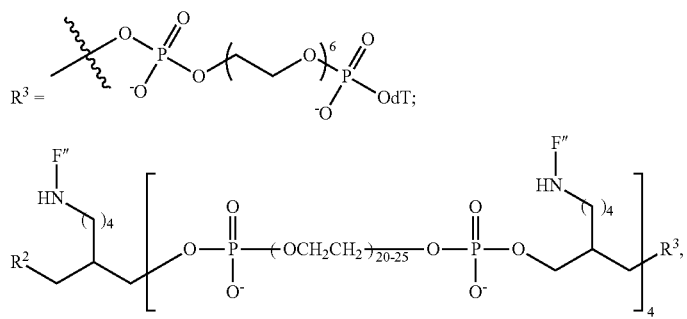
wherein:
I-32
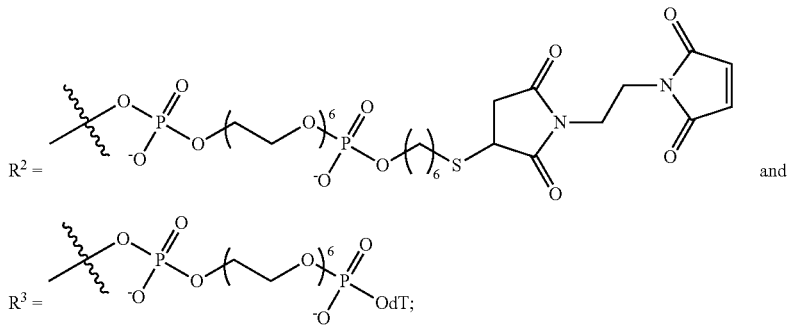
I-33
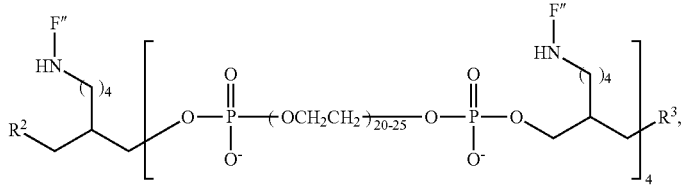
wherein:
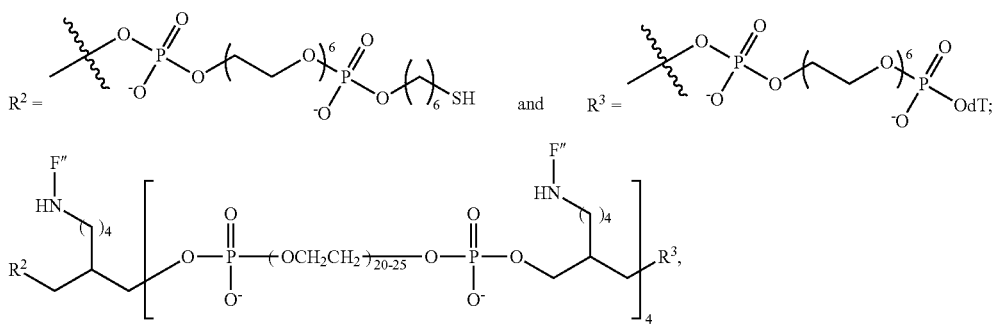
wherein:
I-34
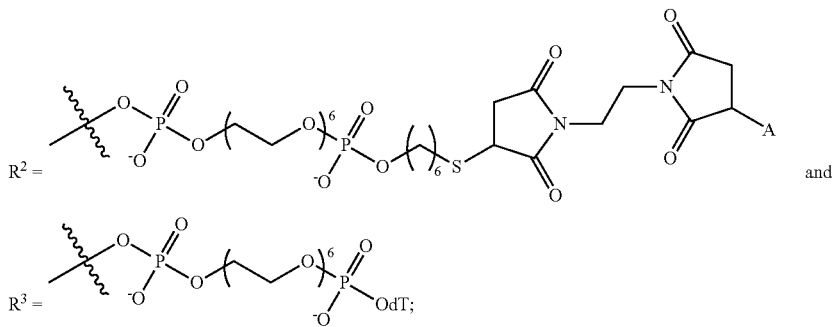

I-35
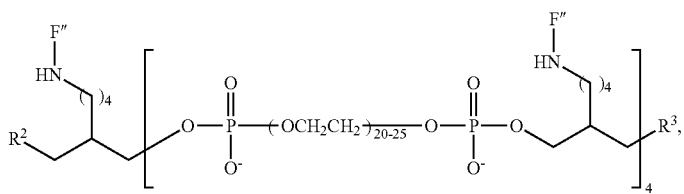
wherein:
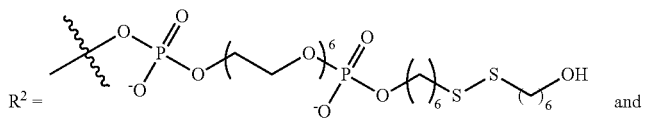
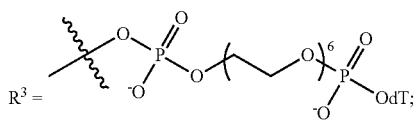
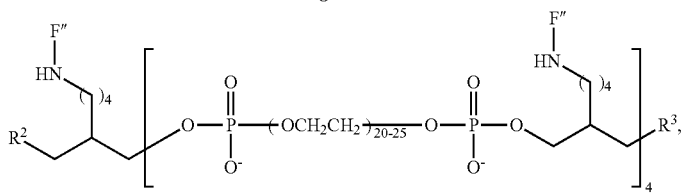
wherein:
I-36
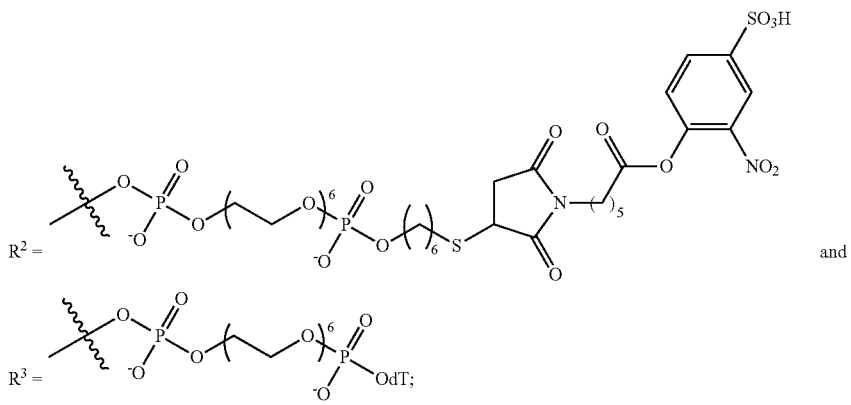
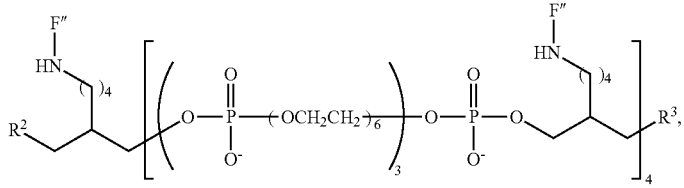
wherein:
I-37
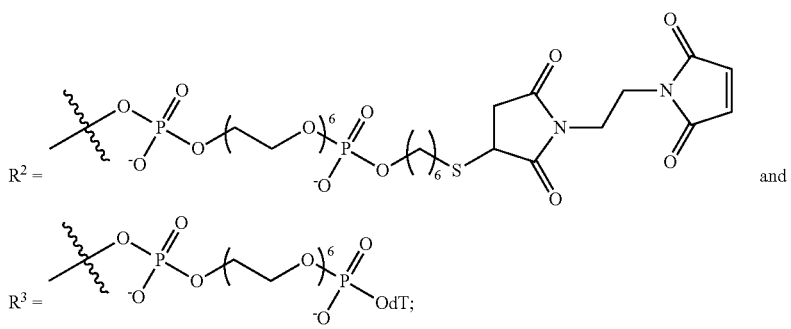

-continued
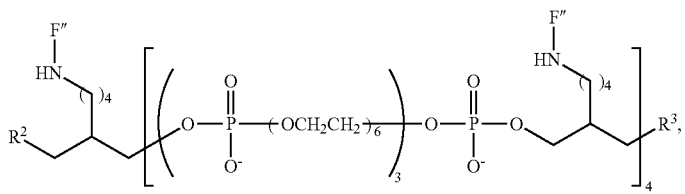
wherein:
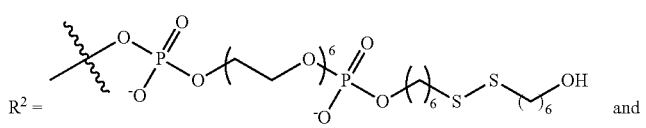
I-38
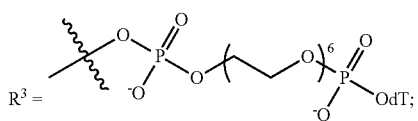
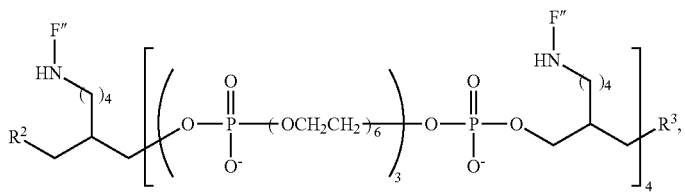
wherein:
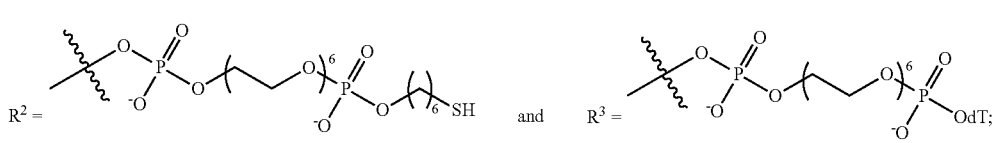
I-39
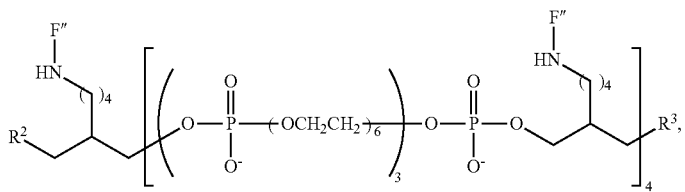
wherein:
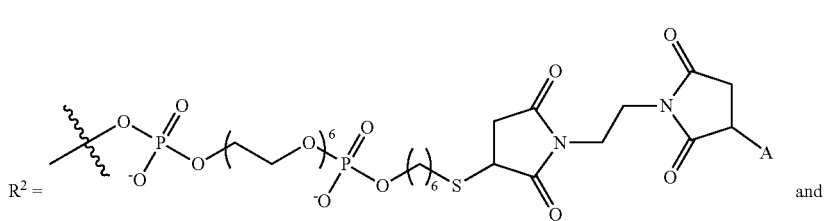
I-40
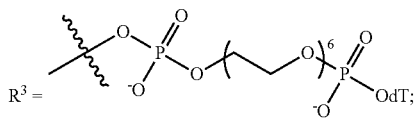

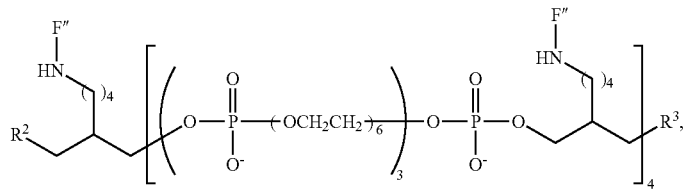
wherein:
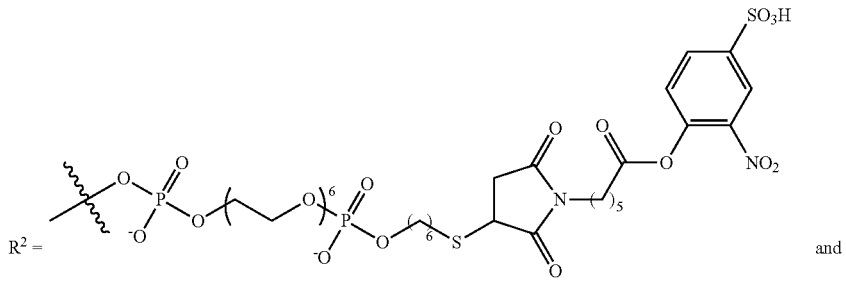
I-41
and
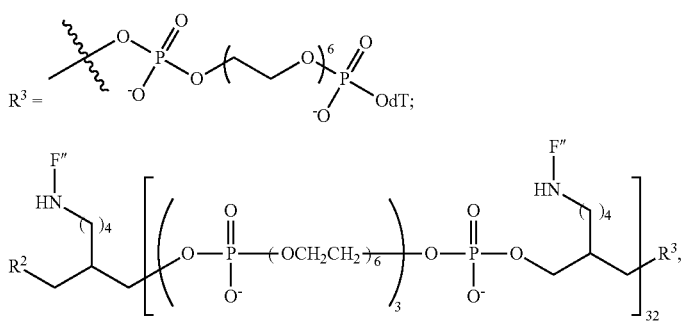
wherein:
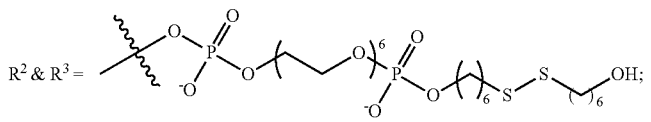
I-42
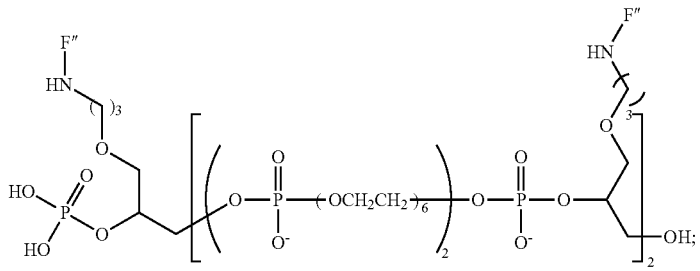
I-43
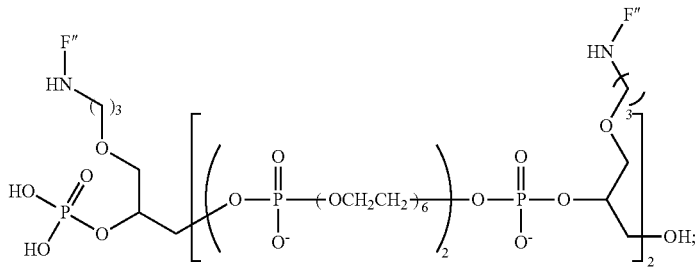
I-44

I-45
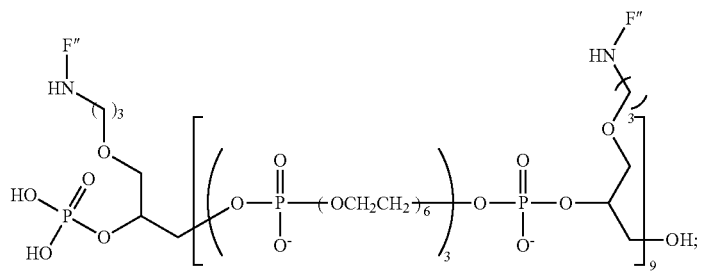
wherein:
I-46
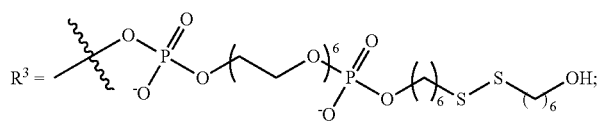
I-47
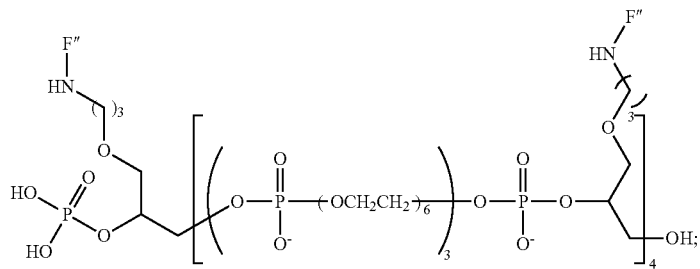
I-48
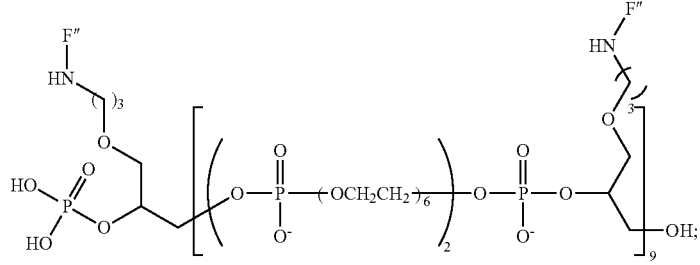
I-49
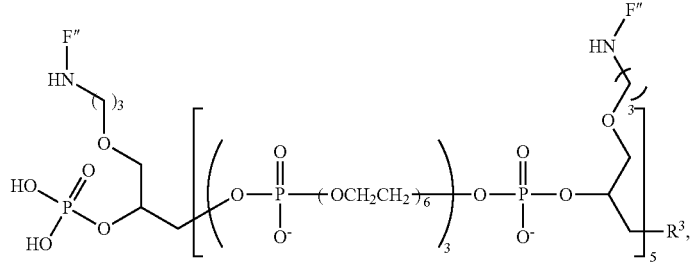
wherein:
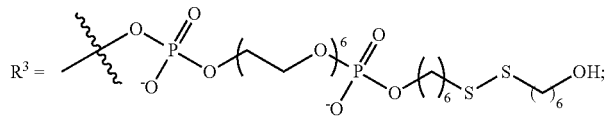

-continued
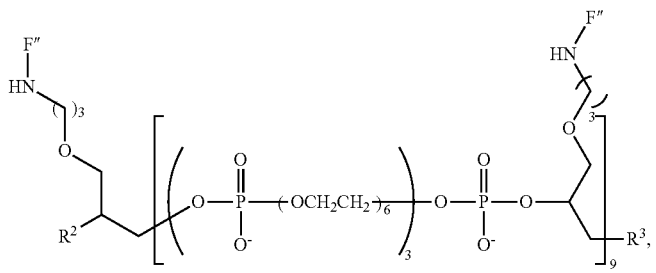
I-50
wherein:
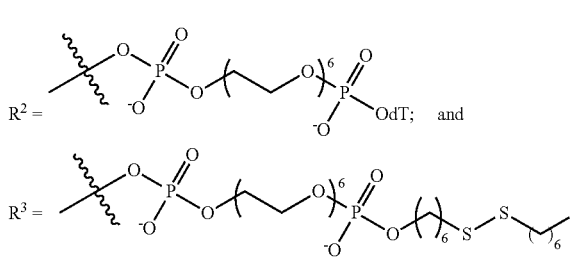
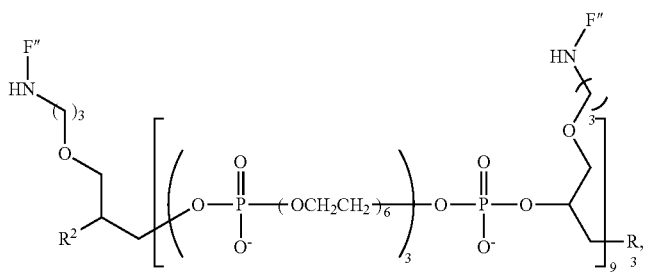
I-51
wherein:
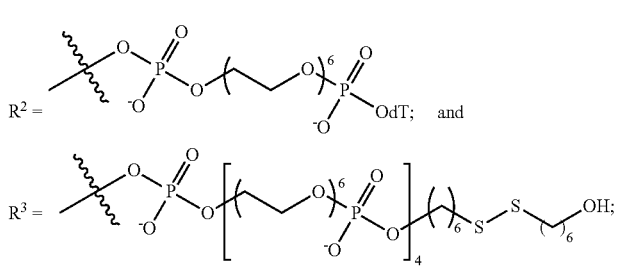
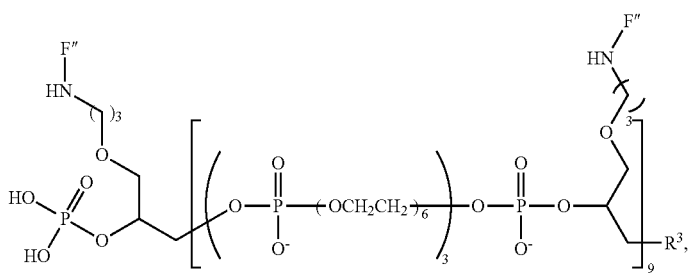
I-52
wherein:
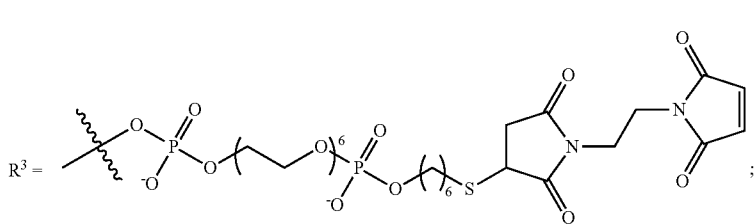

-continued
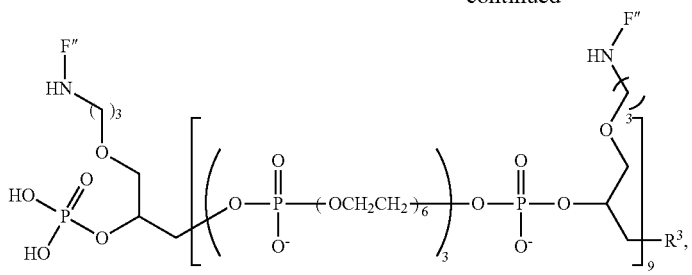
wherein:
I-53
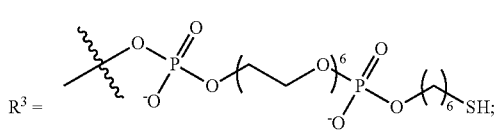
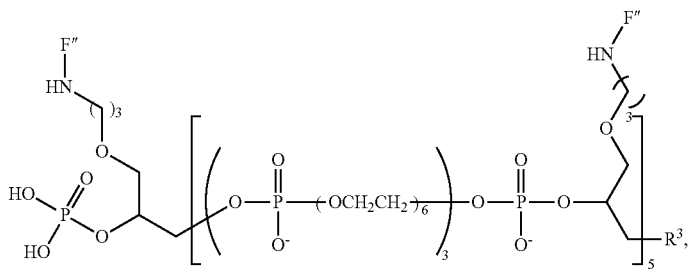
wherein:
I-54
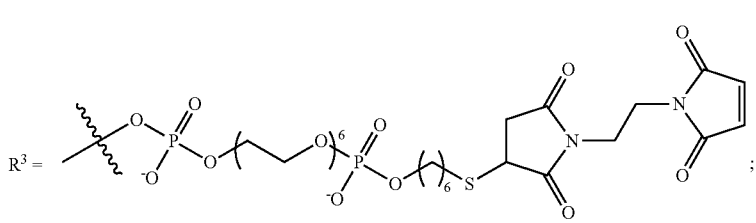
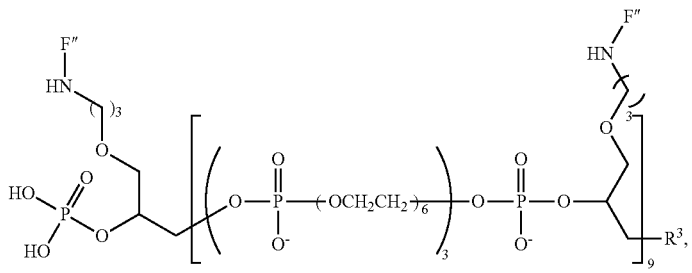
wherein:
I-55
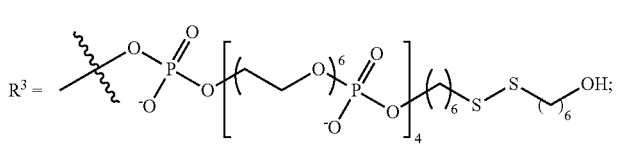

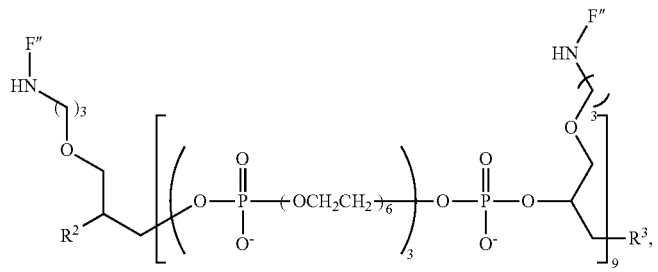
wherein:
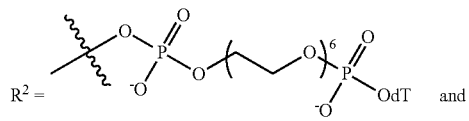
I-56
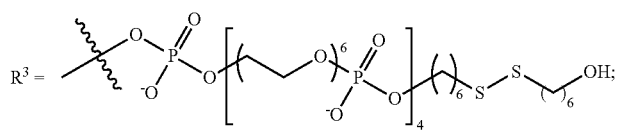
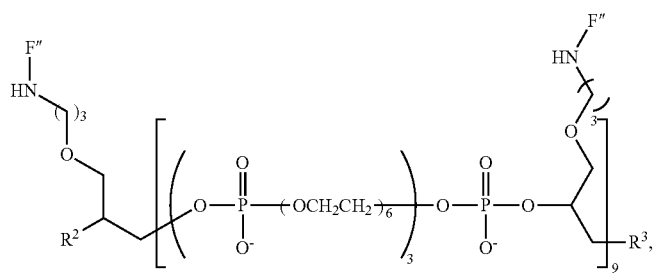
wherein:
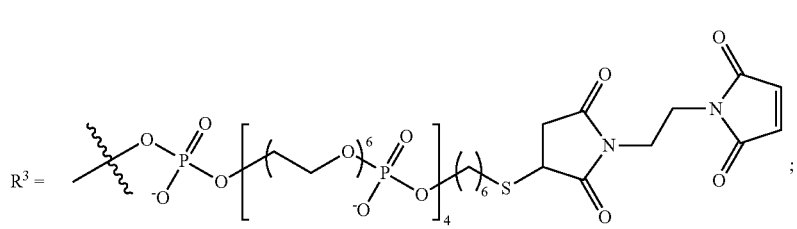
I-57
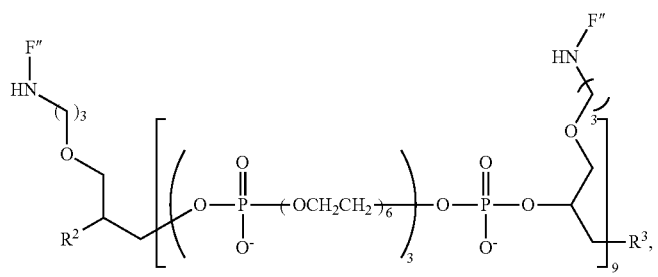
wherein:
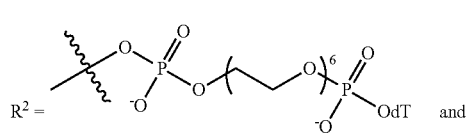
I-58

R³ = 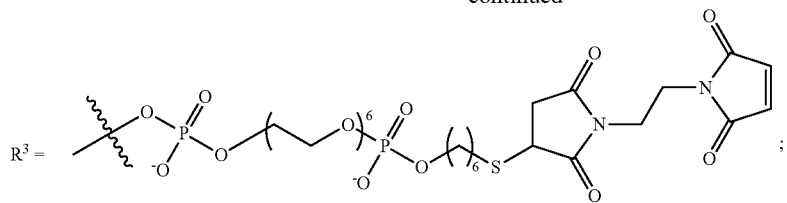
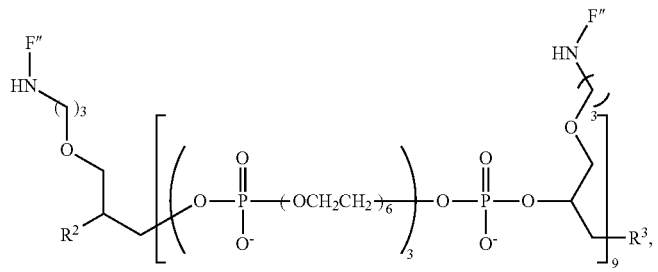
wherein:
R² = 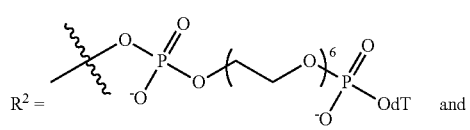 and
I-59
R³ = 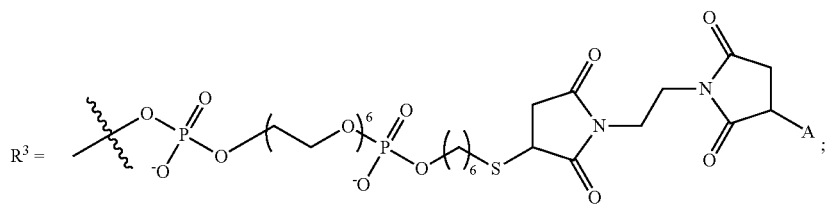
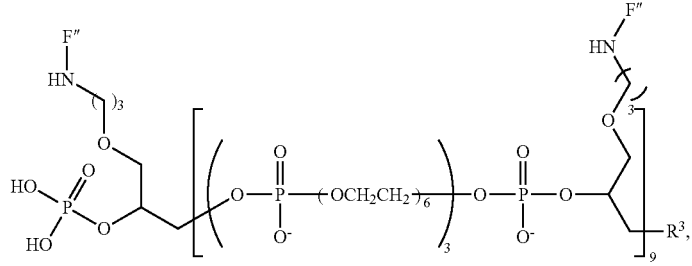
wherein:
I-60
R³ = 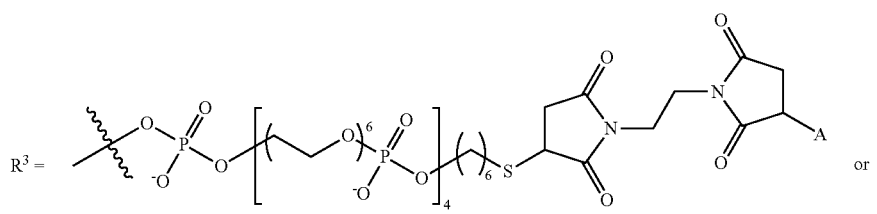 or
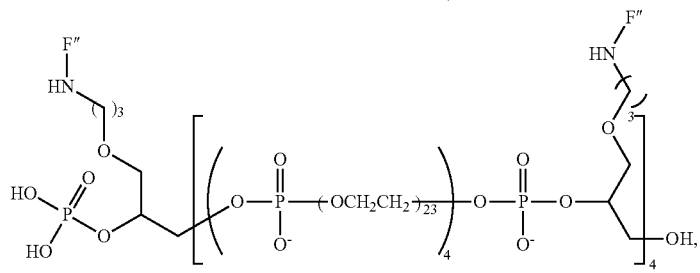

wherein:

each A is independently an antibody;

each m" is independently 4 or 10; and

F, F', F" and dT have the following structures, respectively:

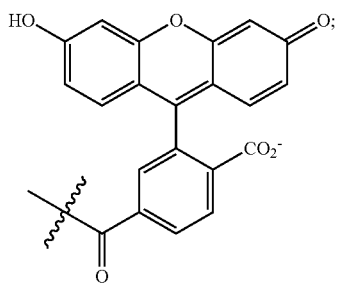

F

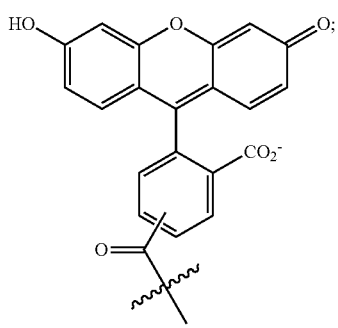

F'

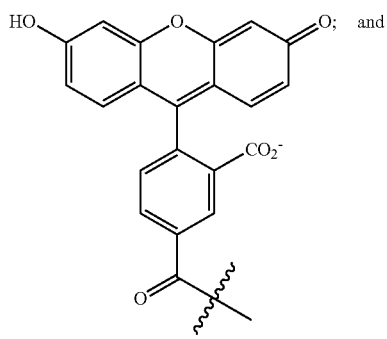

F"

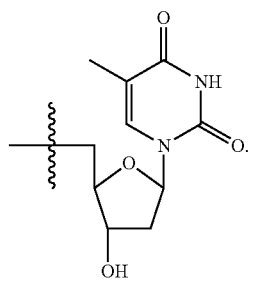

dT

26. A method for visually detecting an analyte, the method comprising:
   (a) providing the compound of claim 1, wherein $R^2$ or $R^3$ comprises a linker comprising a covalent bond to a targeting moiety having specificity for the analyte;
   (b) admixing the compound and the analyte, thereby associating the targeting moiety and the analyte; and
   (c) detecting the compound by its visible properties.

27. A composition comprising the compound of claim 1 and one or more analyte molecules.

* * * * *